US011673853B2

(12) United States Patent
Chen et al.

(10) Patent No.: US 11,673,853 B2
(45) Date of Patent: *Jun. 13, 2023

(54) SMALL MOLECULE AMPK ACTIVATORS

(71) Applicants: University of Pittsburgh—Of the Commonwealth System of Higher Education, Pittsburgh, PA (US); The United States as represented by the Department of Veterans Affairs, Washington, DC (US)

(72) Inventors: Beibei Chen, Pittsburgh, PA (US); Rama K. Mallampalli, Solon, IA (US); Yuan Liu, Pittsburgh, PA (US)

(73) Assignees: UNIVERSITY OF PITTSBURGH—OF THE COMMONWEALTH SYSTEM OF HIGHER EDUCATION, Pittsburgh, PA (US); The United States as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/313,577

(22) Filed: May 6, 2021

(65) Prior Publication Data

US 2022/0153685 A1 May 19, 2022

Related U.S. Application Data

(63) Continuation of application No. 16/339,534, filed as application No. PCT/US2017/055109 on Oct. 4, 2017, now Pat. No. 11,040,935.

(60) Provisional application No. 62/404,592, filed on Oct. 5, 2016.

(51) Int. Cl.
| | | |
|---|---|---|
| *C07C 217/34* | (2006.01) |
| *C07C 215/08* | (2006.01) |
| *C07C 215/18* | (2006.01) |
| *C07D 205/04* | (2006.01) |
| *C07D 217/04* | (2006.01) |
| *C07D 311/88* | (2006.01) |
| *A61P 29/00* | (2006.01) |

(52) U.S. Cl.
CPC ............ *C07C 217/34* (2013.01); *A61P 29/00* (2018.01); *C07C 215/08* (2013.01); *C07C 215/18* (2013.01); *C07D 205/04* (2013.01); *C07D 217/04* (2013.01); *C07D 311/88* (2013.01)

(58) Field of Classification Search
CPC ............... C07C 217/34; C07C 215/08; C07C 215/18; C07D 205/04; C07D 217/04; C07D 311/88
See application file for complete search history.

(56) References Cited

U.S. PATENT DOCUMENTS

| | | | |
|---|---|---|---|
| 4,110,472 A | 8/1978 | Hiltmann et al. |
| 4,410,472 A | 10/1983 | Grubbs et al. |
| 4,552,960 A | 11/1985 | Krumkalns et al. |
| 4,559,354 A | 12/1985 | Fuhrer et al. |
| 5,391,552 A | 2/1995 | Inazu et al. |
| 5,541,204 A | 7/1996 | Sher et al. |
| 6,326,492 B1 | 12/2001 | Wang et al. |
| 7,321,041 B2 | 1/2008 | Cywin et al. |
| 7,365,085 B2 | 4/2008 | Bhat et al. |
| 7,678,911 B2 | 3/2010 | Cywin et al. |
| 7,705,151 B2 | 4/2010 | Cywin et al. |
| 9,500,640 B2 | 11/2016 | Wang et al. |
| 11,040,935 B2 | 6/2021 | Chen et al. |
| 2010/0029689 A1 | 2/2010 | Hopper et al. |
| 2010/0279997 A1* | 11/2010 | Burns Barbier ..... C07D 265/36 564/453 |
| 2014/0018341 A1 | 1/2014 | Wang et al. |
| 2014/0350064 A1 | 11/2014 | Chen |
| 2015/0148318 A1 | 5/2015 | Wang et al. |
| 2020/0062693 A1 | 2/2020 | Chen |

FOREIGN PATENT DOCUMENTS

| | | |
|---|---|---|
| CA | 2043216 | 11/1991 |
| CA | 2078057 | 3/1993 |
| EP | 0039892 | 11/1981 |
| EP | 1426370 | 6/2004 |
| JP | S57-026653 A | 2/1982 |
| JP | 2003-501352 A | 1/2003 |
| JP | 2004-504305 A | 2/2004 |
| JP | 2004-535420 | 11/2004 |
| RU | 2416409 | 4/2011 |
| WO | WO 02/00622 | 1/2002 |
| WO | WO 02/06210 | 1/2002 |
| WO | WO 02/06248 | 1/2002 |
| WO | WO 2002/048134 | 6/2002 |
| WO | WO 2007/118041 | 10/2007 |
| WO | WO 2008/015558 | 2/2008 |
| WO | WO 2008/142454 | 11/2008 |
| WO | WO 2010/051374 | 5/2010 |
| WO | WO 2014/011917 | 1/2014 |

(Continued)

OTHER PUBLICATIONS

Registry No. 424805-21-0, File Registry on STN, Jun. 3, 2002.*
Registry No. 864350-65-2, File Registry on STN, Sep. 30, 2005.*
Registry No. 437765-31-6, File Registry on STN, Jul. 9, 2002.*
Registry No. 864234-45-7, File Registry on STN, Sep. 30, 2005.*
Registry No. 1053064-49-5, File Registry on STN, Sep. 26, 2008.*
Registry No. 424810-74-2, File Registry on STN, Jun. 3, 2002.*
Registry No. 1288379-85-0, File Registry on STN, May 1, 2011.*
Registry No. 1061046-20-5, File Registry on STN, Oct. 14, 2008.*
Registry No. 1065487-01-5, File Registry on STN, Oct. 24, 2008.*
Registry No. 1069519-97-6, File Registry on STN, Nov. 2, 2008.*
Registry No. 449783-37-3, File Registry on STN, Sep. 12, 2002.*
Registry No. 1181769-10-7, File Registry on STN, Sep. 9, 2009.*
Beasley et al. Journal of Pharmacy and Pharmacology (1958), 10, 47-59.*

(Continued)

Primary Examiner — Rebecca L Anderson
(74) Attorney, Agent, or Firm — Fish & Richardson P.C.

(57) ABSTRACT

Described herein are compounds that disrupt the interaction between Fbxo48 and phosphorylated-AMPK.

16 Claims, 22 Drawing Sheets

(56) References Cited

FOREIGN PATENT DOCUMENTS

| WO | WO 2014/012054 | 1/2014 |
|---|---|---|
| WO | WO 2015/054027 | 4/2015 |

OTHER PUBLICATIONS

Beasley et al., "Analgesics. Part I. Some Aryloxypropanolamines," Journal of Pharmacy and Pharmacology, 10(1):47-59, Sep. 1958.
Bergeron et al., "Effect of AMPK activation on muscle glucose metabolism in conscious rats," Am. J. Physiol., 276(5):E938-44, May 1999.
CAS Registry No. 102761-21-7, "2-Propanol, 1-[bis(phenylmethyl)amino]-3-(2-methylphenoxy)," dated Jan. 21, 1986, 2 pages.
CAS Registry No. 1061046-20-5, "2-Propanol, 1-[4-[[(2-methoxyethyl) (1-methylethyl)amino]methyl]phenoxy]-3-[methyl(phenylmethyl)amino]," dated Oct. 14, 2008, 1 page.
CAS Registry No. 1065487-01-5, "2-Propanol, 1-[4-[(cyclopropylamino)methyl]phenoxy]-3-[methyl(phenylmethyl)amino]," dated Oct. 24, 2008, 2 pages.
CAS Registry No. 1069519-97-6, "2-Propanol, 1-[methyl(phenylmethyl)amino]-3-[4-[[[(2-methylphenyl)methyl]amino]methyl]phenoxy]-," dated Nov. 2, 2008, 1 page.
CAS Registry No. 1181769-10-7, "2-Propanol, 1-(4-fluorophenoxy)-3-[(4-fluorophenyl)amino]," dated Sep. 9, 2009, 1 page.
CAS Registry No. 1288379-85-0, "2-Propanol, 1-[(diphenylmethyl)amino]-3-(4-fluorophenoxy)," dated May 1, 2011, 2 pages.
CAS Registry No. 1392100-59-2, "2-Propanol, 1-[(diphenylmethyl)amino]-3-phenoxy," dated Aug. 22, 2012, 1 page.
CAS Registry No. 152533-41-0, "2-Propanol, 1-[bis(phenylmethyl)amino]-3-phenoxy," dated Jan. 27, 1994, 2 pages.
CAS Registry No. 311812-45-0, "2-Propanol, 1-[bis(phenylmethyl)amino]-3-(4-methoxyphenoxy)," dated Dec. 28, 2000, 2 pages.
CAS Registry No. 332150-46-6, "2-Propanol, 1,1'-[1,4-phenylenebis(oxy)Jbis[3-[(phenylmethyl)amino]," dated Apr. 24, 2001, 1 page.
CAS Registry No. 424805-21-0, "[1, 1' 1-Biphenyl)-4-carbonitrile, 4'-[3-[bis (phenylmethyl) amino]-2-hydroxypropoxy]," dated Jun. 3, 2002, 1 page.
CAS Registry No. 424810-74-2, "2-Propanol, 1-[bis(phenylmethyl)amino]-3-(2-naphthalenyloxy," dated Jun. 3, 2002, 2 pages.
CAS Registry No. 432496-91-8, "2-Propanol, 1-[bis(phenylmethyl)amino]-3-(4-methylphenoxy)," dated Jun. 20, 2002, 2 pages.
CAS Registry No. 449783-37-3, "2-Propanol, 1,1'-[1,4-phenylenebis(oxy)]bis[3-[bis(phenylmethyl)amino]," dated Sep. 12, 2002, 2 pages.
CAS Registry No. 861092-43-5, "2-Naphthalenemethanol, a-[[bis(phenylmethyl)amino]methyl]," dated Aug. 19, 2005, 2 pages.
Cepanec et al., "Calcium trifluoromethanesulfonate-catalysed aminolysis of epoxides," Tetrahedron, 59(14):2435-2439, Mar. 2003.
Deng et al., "Deubiquitination and Activation of AMPK by USP10," Mol. Cell, 61(4):614-24, Feb. 2016.
Durante et al., "Effects of endurance training on activity and expression of AMP-activated protein kinase isoforms in rat muscles," Am. J. Physiol. Endocrinol. Metab., 283(1):E178-86, Jul. 2002.
EurekAler.org [online],"Scripps Research Institute scientists help unravel central mystery of Alzheimer's disease," Apr. 2013 retrieved from URL<https://www.eurekalert.org/pub_releases/2013-04/sri-sri040513.php>, 4 pages, retrieved on Sep. 5, 2019.
Florant, et al., "To eat or not to eat: the effect of AICAR on food intake regulation in yellow-bellied marmots (Marmota flaviventris)," J. Exp. Biol., 213:2031-7, Feb. 2010.
Gârea et al., "Synthesis and characterization of new nanocomposites based on epoxy resins and organophilic clays," Polymer international, 56(9):1106-14, Sep. 2007.
Immediata et al., "β-Naphthyl derivatives of ethanolamine and n-substituted ethanolamines," The Journal of Organic Chemistry, 5(5):512-27, 1940.
Khalil et al., "Synthesis of Certain (Heterocyclic Substituted Aryloxy) Propanolamines as Potential Adrenoceptor Antagonists," Bull. Fac. Pharm. Cario University, 2002, 40(1):23-29.
Khalil et al., "Synthesis of Certain Propanolamines as Potential Adrenoceptor Antagonists," Bull. Fac. Pharm. Cario University, 2002, 40(2):23-29.
Musi et al., "Metformin increases AMP-activated protein kinase activity in skeletal muscle of subjects with type 2 diabetes," Diabetes, 51(7):2074-81, Jul. 2002.
Notari, "Theory and Practice of Prodrug Kinetics," Methods Enzymol., 112(24):309-23, 1985.
Ojuka, "Role of calcium and AMP kinase in the regulation of mitochondrial biogenesis and GLUT4 levels in muscle," Proc. Nutr. Soc., 63(2): 275-8, May 2004.
PCT International Preliminary Report on Patentability in International Appln. No. PCT/US2017/055109 dated Apr. 9, 2019, 7 pages.
PCT International Search Report and Written Opinion in International Appln. Np. PCT/US2017/055109 dated Jan. 18, 2018, 9 pages.
Perrone et al., "Stereospecific synthesis and bio-activity of novel β3-adrenoceptor agonists and inverse agonists," Bioorganic & medicinal chemistry, 16(5):2473-88, Mar. 2008.
Pineda et al., "Degradation of AMPK by a Cancer-Specific Ubiquitin Ligase," Cell, 160(4): 715-28, Feb. 2015.
Pubchem.ncbi.nlm.nih.gov [online], "Substance record for 1-Benzylamino-2-propanol," Dec. 3, 2015, retrieved from URL<https://pubchem.ncbi.nlm.nih.gov/substance/255445051>, 4 pages, retrieved on Sep. 5, 2019.
Reddy et al., "Lewis Acid Mediated Nucleophilic Ring-Opening of 1-Benzhydryl Azetidine-3-ol with Aryl Alcohols: A Formal Synthesis of Carvedilol," Asian Journal of Chemistry 24(8), Aug. 2012.
Ronnett., "AMPK in the brain: its roles in energy balance and neuroprotection," J. Neurochem., 109(Suppl. 1):17-23, May 2009.
Tanaka et al., "Potent Plasmodium falciparum Gametocytocidal Activity of Diaminonaphthoquinones, Lead Antimalarial Chemotypes Identified in an Antimalarial Compound Screen," Antimicrob. Agents Chemotherapy, Mar. 2015, 59(3):1389-1397.
Thomson et al., "Skeletal muscle and heart LKB1 deficiency causes decreased voluntary running and reduced muscle mitochondrial marker enzyme expression in mice," Am. J. Physiol. Endocrinol. Metab., 292(1): E196-202, Jan. 2007.
Wang et al., "Ghrelin inhibits insulin secretion through the AMPK-UCP2 pathway in β cells," FEBS lett., 584(8):1503-8, Apr. 2010.
Winder and Hardie, "AMP-activated protein kinase, a metabolic master switch: possible roles in Type 2 diabetes," Am. J. Physiol., 277(1):E1-10, Jul. 1999.
Winder, "Energy-sensing and signaling by AMP-activated protein kinase in skeletal muscle," J. Appl. Physiol., 91(3):1017-28, Sep. 2001.
Yamamoto et al., "Regio-and stereo-selective ring opening of epoxides with amide cuprate reagents," Journal of the Chemical Society, Chemical Communications, 1993(15):1201-3, 1993.
Zhou et al., "Role of AMP-activated protein kinase in mechanism of metformin action," J. Clin. Invest., 108(8):1167-74, Oct. 2001.
Zindell et al., "Morpholine containing CB2 selective agonists," Bioorganic & medicinal chemistry letters, 19(6):1604-9, Mar. 2009.
Lizza et al., "Solvent-Directed Epoxide Opening with Primary Amines for the Synthesis of β-Amino Alcohols," Synthesis, Nov. 19, 2016, 49(6):1231-1242.
Zhang et al., "Discovery of Novel Antimalarial Compounds Enabled by QSAR-Based Virtual Screening," J. Chem. Inf. Modeling, Dec. 19, 2012, 53(2):475-492.

* cited by examiner

SMALL MOLECULE AMPK ACTIVATORS

CROSS-REFERENCE TO RELATED APPLICATIONS

This application is a continuation application of allowed national stage application Ser. No. 16/339,534, filed Apr. 4, 2019, under 35 U.S.C. § 371 of International Application No. PCT/US2017/055109, having an International Filing Date of Oct. 4, 2017, which claims the benefit of priority to U.S. Provisional Application No. 62/404,592, filed on Oct. 5, 2016, all of which are incorporated herein by reference their entirety. The disclosures of the prior applications are considered part of (and are incorporated by reference in) the disclosure of this application.

GOVERNMENT LICENSE RIGHTS

This invention was made with government support under grant nos. HL096376; HL097376; HL098174; HL081784; HL114453; HL116472; and HL132862 awarded by the NIH. The government has certain rights in the invention.

FIELD

The present subject matter relates generally to compounds that prevent the ubiquination and subsequent degradation of AMP-activated protein kinase (AMPK). AMPK, also known as 5' AMP-activated protein kinase or 5' adenosine monophosphate-activated protein kinase, is an enzyme that plays a role in cellular energy homeostasis. AMPK functions as a metabolic fuel gauge and master metabolic regulator that is activated in response to environmental stressors to restore cellular energy balance. Upon metabolic stress, AMPK suppresses anabolic and promotes catabolic processes to regain energy homeostasis. In the heart, AMPK coordinates the activation of glucose and fatty acid metabolic pathways to ensure increased production of myocardial ATP when required, such as during cardiac ischemia/reperfusion and hypertrophy, causing an increase in AMPK activity that can be viewed as both protective and maladaptive.

AMPK exists as an obligate heterotrimer, composed of three subunits: catalytic kinase α subunit and two associated regulatory subunits, β and γ (subunits), that together make a functional enzyme. It is expressed in a number of tissues, including the liver, brain, and skeletal muscle. Winder W W, Hardie D G, *Am. J. Physiol.*, 277 (1 Pt 1): E1-10 (1999).

AMPK acts as a metabolic master switch regulating several intracellular systems including the cellular uptake of glucose, the (3-oxidation of fatty acids and the biogenesis of glucose transporter 4 (GLUT4) and mitochondria. Thomson et al., *Am. J. Physiol. Endocrinol. Metab.*, 292(1): E196-202 (2007); Ojuka E O, *Proc. Nutr. Soc.*, 63(2): 275-8 (2004); Durante et al., *Am. J. Physiol. Endocrinol. Metab.*, 283(1): E178-86 (2002); Bergeron et al., *Am. J. Physiol.*, 276 (5 Pt 1): E938-44 (1999); Winder W W, *J. Appl. Physiol.*, 91(3): 1017-28 (2001). A recent paper on mice at Johns Hopkins has shown that when the activity of brain AMPK was pharmacologically inhibited, the mice ate less and lost weight. When AMPK activity was pharmacologically raised the mice ate more and gained weight. Gabriele et al., *J. Neurochem.*, 109 Suppl 1: 17-23 (2009). Research in hibernators has also shown that activation of AMPK induces arousal from hibernation and stimulates food intake. Florant, et al., *JEB*, 213: 2031-2037 (2010). Research in Britain has shown that the appetite-stimulating hormone ghrelin also affects AMPK levels. Wang et al., *FEBS letters*, 584:1503-8 (2010). The antidiabetic drug metformin (Glucophage) acts by stimulating AMPK (Zhou et al., *J. Clin. Invest.*, 108 (8): 1167-74 (2001); Musi et al., *Diabetes*, 51(7):2074-81 (2002)), leading to reduced glucose production in the liver and reduced insulin resistance in the muscle. (Metformin usually causes weight loss and reduced appetite, not weight gain and increased appetite, which is opposite of what might be expected given the Johns Hopkins mouse study results.) Recent research has implicated overproduction of AMPK in the genesis of Alzheimer's disease. Polleux, F., "Scripps Research Institute scientists help unravel central mystery of Alzheimer's disease," Press Release dated 10 Apr. 2013, from www.eurekalert.org (EurekAlert!). This has raised theoretical concern over the safety of Metformin.

AMPK is the master regulator of metabolic homeostasis by sensing cellular energy status. When intracellular ATP levels decrease during energy stress, AMPK is initially activated through AMP or ADP binding and phosphorylation of a threonine residue (Thr-172) within the activation loop of its kinase domain. It has recently been reported that ubiquitination on AMPKα blocks AMPKα phosphorylation by LKB1. The deubiquitinase USP10 specifically removes ubiquitination on AMPKα to facilitate AMPKα phosphorylation by LKB1. Under energy stress, USP10 activity in turn is enhanced through AMPK-mediated phosphorylation of Ser76 of USP10. Thus, USP10 and AMPK form a key feedforward loop ensuring amplification of AMPK activation in response to fluctuation of cellular energy status. Disruption of this feedforward loop leads to improper AMPK activation and multiple metabolic defects. Deng et al., *Mol. Cell*, 67:614-624 (2016).

Degradation of AMPK by a cancer-specific ubiquitin ligase has been reported in the literature. Cancer cells can occasionally suppress the growth-restrictive AMPK pathway by mutation of an upstream regulatory kinase. A mechanism to suppress AMPK through its ubiquitination and degradation by the cancer-specific MAGE-A3/6-TRIM28 ubiquitin ligase is described in Pineda et al., *Cell*, 160(4):715-728 (2015). Pineda et al. report that MAGE-A3/6 are necessary for cancer cell viability and are sufficient to drive tumorigenic properties of non-cancerous cells. Screening for targets of MAGE-A3/6-TRIM28 revealed that it ubiquitinates and degrades AMPKα1.

There is a need in the art for compounds that prevent the ubiquination and subsequent degradation of AMPK. The present subject matter satisfies this need.

SUMMARY

In one aspect, provided herein are compounds of Formula I:

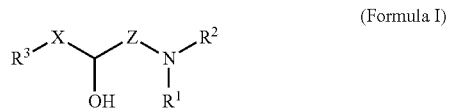

(Formula I)

wherein:
X is $C_{0-3}$ alkyl, —$(CH_2)_2$—NH—$(CH_2)_2$—, —NH—$CH_2$—, —O—$CH_2$—, —O—$(CH_2)_2$—, —$(CH_2)_2$—O—$(CH_2)_2$—, or —$(CH_2)$—C$(NH_2)$—$(CH_2)_a$—;
Z is $C_{1-2}$ alkyl, —$(CH_2)$—NH—$(CH_2)$—, —$(CH_2)$—O—$(CH_2)$—, or —$(CH_2)_a$—C$(NH_2)$—$(CH_2)$—;
a is 0 or 1;

at least one of $R^1$ and $R^2$ is —$(CHR^A)_b$—Y, wherein each $R^A$ is independently H, or a substituted or unsubstituted aryl; and b is 0 or an integer of 1-3;

the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl; or $R^1$ and $R^2$, together with the nitrogen to which they are attached, form a substituted or unsubstituted heterocyclic ring;

$R^3$ is an alkyl, carbocyclyl, aryl, or heteroaryl group, wherein each alkyl, carbocyclyl, aryl, or heteroaryl group is optionally substituted by one or more

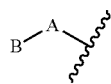

wherein:

A is C=O, SO, $SO_2$, or —$(C(R^B)_2)_d$—, wherein each $R^B$ is independently selected from H, D, halogen, OH, substituted or unsubstituted alkyl, and substituted or unsubstituted alkoxy;

d is 0 or an integer of 1-3; and

B is selected from the group consisting of substituted or unsubstituted alkyl, substituted or unsubstituted alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof. In some embodiments, $R^3$ is an alkyl group optionally substituted by one or more

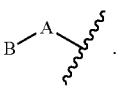.

In some embodiments, $R^3$ is an carbocyclyl group optionally substituted by one or more

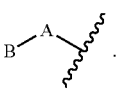.

In some embodiments, $R^3$ is an aryl group optionally substituted by one or more

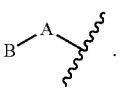.

In some embodiments, $R^3$ is an heteroaryl group optionally substituted by one or more

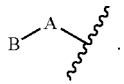.

In another aspect, provided herein are compounds of Formula II:

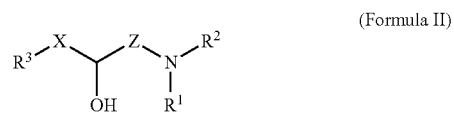

(Formula II)

wherein:

X is $C_{0-3}$ alkyl, —$(CH_2)_2$—NH—$(CH_2)_2$—, —NH—$CH_2$—, —O—$CH_2$—, —O—$(CH_2)_2$—, —$(CH_2)_2$—O—$(CH_2)_2$—, or —$(CH_2)$—$C(NH_2)$—$(CH_2)_a$—;

Z is $C_{1-2}$ alkyl, —$(CH_2)$—NH—$(CH_2)$—, —$(CH_2)$—O—$(CH_2)$—, or —$(CH_2)_a$—$C(NH_2)$—$(CH_2)$—;

a is 0 or 1;

at least one of $R^1$ and $R^2$ is —$(CHR^A)_b$—Y, wherein each $R^A$ is independently H, or a substituted or unsubstituted aryl; and b is 0 or an integer of 1-3;

the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl; or $R^1$ and $R^2$, together with the nitrogen to which they are attached, form a substituted or unsubstituted heterocyclic ring;

$R^3$ is an aryl or heteroaryl group optionally substituted by one or more

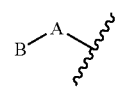

wherein:

A is C=O, SO, $SO_2$, or —$(C(R^B)_2)_d$—, wherein each $R^B$ is independently selected from H, D, halogen, OH, substituted or unsubstituted alkyl, and substituted or unsubstituted alkoxy;

d is 0 or an integer of 1-3; and

B is selected from the group consisting of $C_{1-6}$ alkyl, haloalkyl, $C_{1-6}$ alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof.

In some embodiments of Formula I or Formula II, $R^3$ is unsubstituted phenyl, unsubstituted naphthyl, or phenyl substituted with one or two

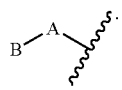.

In some embodiments of Formula I or Formula II, $R^3$ is unsubstituted phenyl or phenyl substituted with one

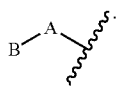

In some embodiments of Formula I or Formula II, $R^3$ is phenyl substituted with one

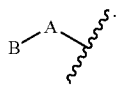

In some embodiments of Formula I or Formula II, A is —$C(R^B)_2)_d$—. In some embodiments of Formula I or Formula II, $R^B$ is H, or substituted or unsubstituted alkyl. In some embodiments of Formula I or Formula II, d is 0. In some embodiments of Formula I or Formula II, d is an integer of 1-3. In some embodiments of Formula I or Formula II, A is C=O. In some embodiments of Formula I or Formula II, A is SO or $SO_2$. In some embodiments of Formula I or Formula II, B is selected from the group consisting of $C_{2-6}$ alkyl, haloalkyl, $C_{2-6}$ alkoxy, substituted or unsubstituted aryl, substituted or unsubstituted carbocyclyl, substituted or unsubstituted heterocyclyl, and substituted or unsubstituted heteroaryl. In some embodiments of Formula I or Formula II, B is selected from the group consisting of $C_{2-6}$ alkyl, haloalkyl, $C_{2-6}$ alkoxy, substituted or unsubstituted phenyl, substituted or unsubstituted $C_{3-8}$ carbocyclyl, and substituted or unsubstituted six-membered heteroaryl. In some embodiments of Formula I or Formula II, B is selected from the group consisting of haloalkyl, $C_{2-6}$ alkoxy, substituted or unsubstituted phenyl, $C_{3-8}$ carbocyclyl, and substituted or unsubstituted six-membered heteroaryl. In some embodiments of Formula I or Formula II, the substituted or unsubstituted six-membered heteroaryl is a substituted or unsubstituted pyridine. In some embodiments of Formula I or Formula II, $R^3$ is unsubstituted phenyl. In some embodiments of Formula I or Formula II, X is $C_{0-3}$ alkyl, —NH—$CH_2$—, or —O—$CH_2$—. In some embodiments of Formula I or Formula II, X is $C_{0-3}$ alkyl. In some embodiments of Formula I or Formula II, X is $C_0$ alkyl. In some embodiments of Formula I or Formula II, X is $C_{1-3}$ alkyl. In some embodiments of Formula I or Formula II, X is $C_2$ alkyl. In some embodiments of Formula I or Formula II, X is $CH_2CH_2$. In some embodiments of Formula I or Formula II, X is —NH—$CH_2$—. In some embodiments of Formula I or Formula II, X is —O—$CH_2$—. In some embodiments of Formula I or Formula II, Z is $C_{1-2}$ alkyl. In some embodiments of Formula I or Formula II, Z is $C_1$ alkyl. In some embodiments of Formula I or Formula II, Z is $CH_2$. In some embodiments of Formula I or Formula II, at least one of $R^1$ and $R^2$ is —$(CHR^A)_b$—Y, wherein each $R^A$ is independently H, or a substituted or unsubstituted aryl; and b is 0 or an integer of 1-3; the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl. In some embodiments of Formula I or Formula II, the remaining one of $R^1$ and $R^2$ is —$(CH_2)_c$—Y or selected from the group consisting of H, substituted or unsubstituted alkyl, substituted or unsubstituted aryl, and substituted or unsubstituted carbocyclyl; and c is 0 or an integer of 1-3. In some embodiments of Formula I or Formula II, the remaining one of $R^1$ and $R^2$ is —$(CH_2)_c$—Y or H; and c is 0 or an integer of 1-3. In some embodiments of Formula I or Formula II, b is 0 or 1; and the remaining one of $R^1$ and $R^2$ is —$(CH_2)$—Y or H. In some embodiments of Formula I or Formula II, each $R^A$ is independently H, or a substituted or unsubstituted phenyl; b is 0 or 1; the remaining one of $R^1$ and $R^2$ is —$(CH_2)$—Y or H; and each Y is a substituted or unsubstituted phenyl. In some embodiments of Formula I or Formula II, $R^A$ is H. In some embodiments of Formula I or Formula II, $R^A$ is phenyl. In some embodiments of Formula I or Formula II, b is 1. In some embodiments of Formula I or Formula II, b is 0. In some embodiments of Formula I or Formula II, the remaining one of $R^1$ and $R^2$ is —$(CH_2)$—Y. In some embodiments of Formula I or Formula II, the remaining one of $R^1$ and $R^2$ is H. In some embodiments of Formula I or Formula II, $R^1$ and $R^2$, together with the nitrogen to which they are attached, form a substituted or unsubstituted heterocyclic ring. In some embodiments of Formula I or Formula II, $R^1$ and $R^2$, together with the nitrogen to which they are attached, form a substituted or unsubstituted tetrahydroisoquinoline.

In another aspect, provided herein are compounds selected from the group consisting of:

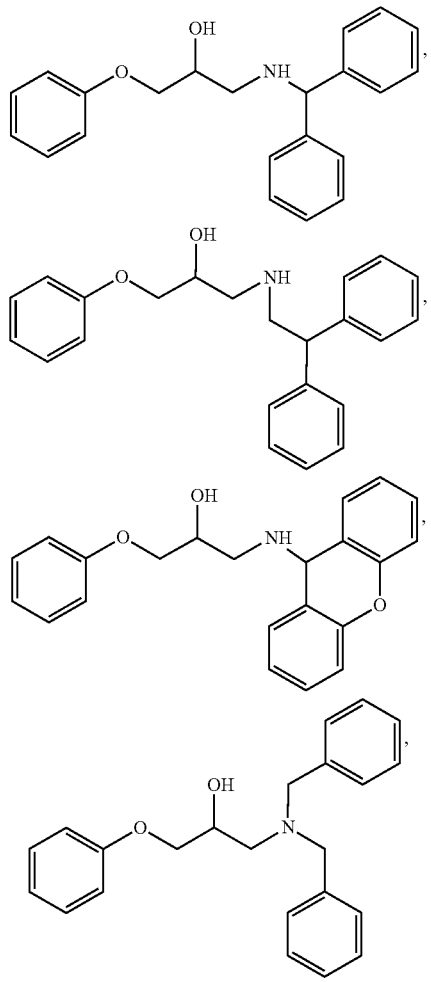

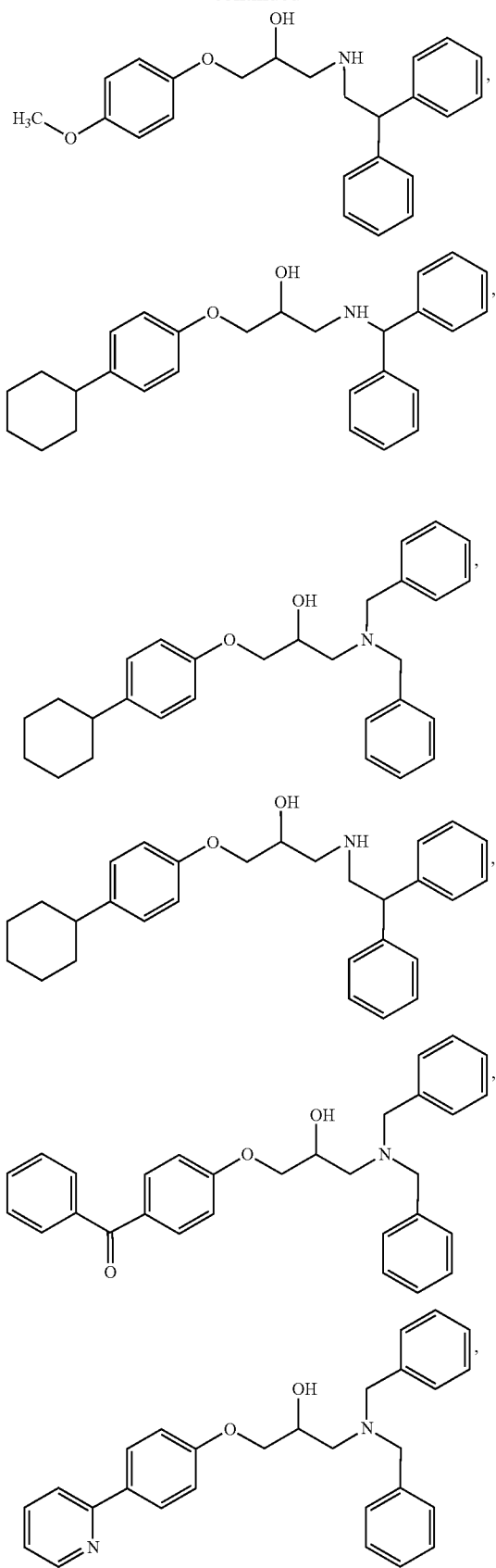
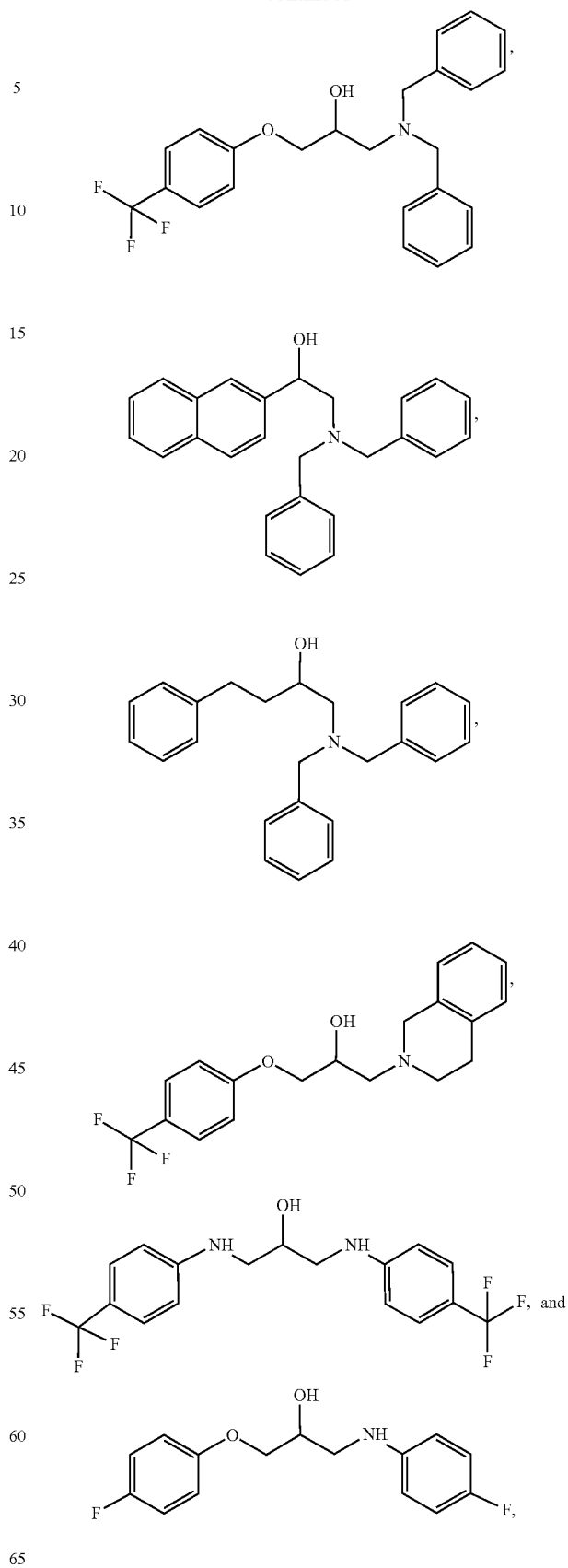
or a stereoisomer thereof, or a pharmaceutically acceptable salt or ester thereof.

In another aspect, provided herein are compounds selected from the group consisting of:
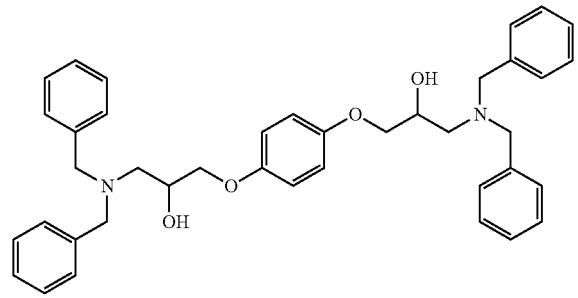 [SMILES: OC(COc1ccc(OCC(O)CN(Cc2ccccc2)Cc2ccccc2)cc1)CN(Cc1ccccc1)Cc1ccccc1]
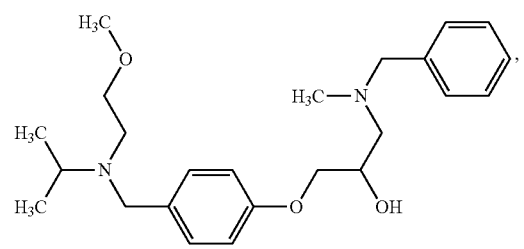
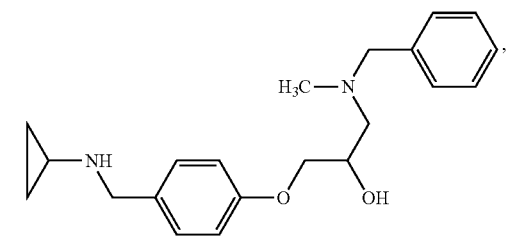
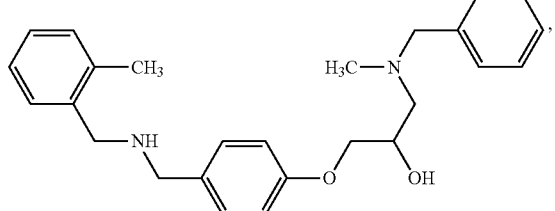
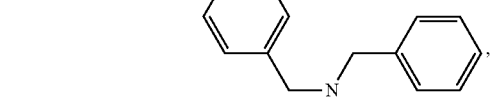
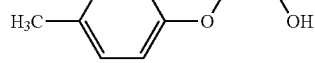
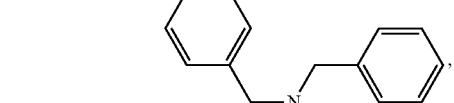
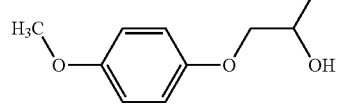
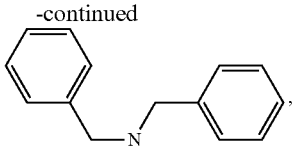
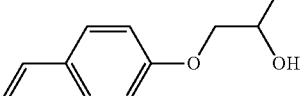
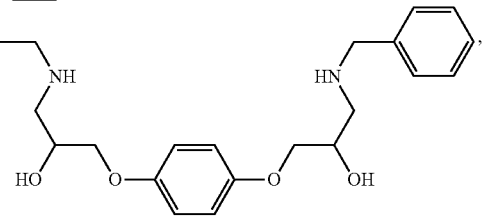
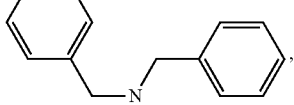
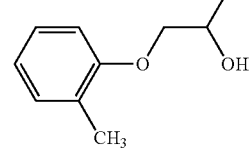
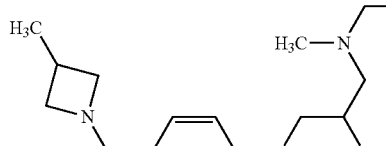
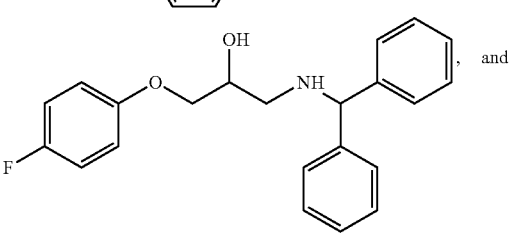
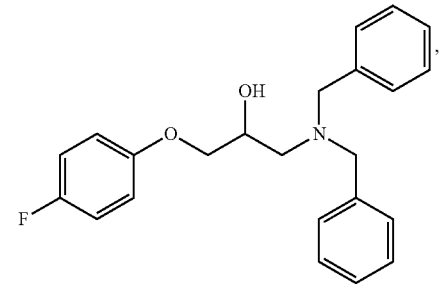
or a stereoisomer thereof, or a pharmaceutically acceptable salt or ester thereof.
In another aspect, provided herein are methods to bind a ubiquitin E3 ligase, the method comprising contacting the ubiquitin E3 ligase with a compound described herein, or a stereoisomer thereof, or a pharmaceutically acceptable salt or ester thereof.

In another aspect, provided herein are methods to treat inflammation in a subject in need thereof, the method comprising administering to the subject a therapeutically effective amount of a compound described herein, or a stereoisomer thereof, or a pharmaceutically acceptable salt or ester thereof.

In another aspect, provided herein are methods to treat cytokine-driven inflammation in a subject in need thereof, the method comprising administering to the subject a therapeutically effective amount of a compound described herein, or a stereoisomer thereof, or a pharmaceutically acceptable salt or ester thereof.

In another aspect, provided herein are methods to treat sepsis in a subject in need thereof, the method comprising administering to the subject a therapeutically effective amount of a compound described herein, or a stereoisomer thereof, or a pharmaceutically acceptable salt or ester thereof.

In another aspect, provided herein are methods to treat acute lung injury in a subject in need thereof, the method comprising administering to the subject a therapeutically effective amount of a compound described herein, or a stereoisomer thereof, or a pharmaceutically acceptable salt or ester thereof.

In another aspect, provided herein are methods to treat metabolic syndrome in a subject in need thereof, the method comprising administering to the subject a therapeutically effective amount of a compound described herein, or a stereoisomer thereof, or a pharmaceutically acceptable salt or ester thereof.

In another aspect, provided herein are methods to increase the level of phosphorylated-AMPK in a subject in need thereof, the method comprising administering to the subject a therapeutically effective amount of a compound described herein, or a stereoisomer thereof, or a pharmaceutically acceptable salt or ester thereof.

In another aspect, provided herein are methods to disrupt interaction between Fbxo48 and phosphorylated-AMPK in a cell, the method comprising contacting the cell with a compound described herein, or a stereoisomer thereof, or a pharmaceutically acceptable salt or ester thereof.

In another aspect, provided herein are methods to disrupt interaction between Fbxo48 and phosphorylated-AMPK in a subject in need thereof, the method comprising administering to the subject a therapeutically effective amount of a compound described herein, or a stereoisomer thereof, or a pharmaceutically acceptable salt or ester thereof.

The foregoing general description and following brief description of the drawings and detailed description are exemplary and explanatory and are intended to provide further explanation of the subject matter as claimed. Other objects, advantages, and novel features will be readily apparent to those skilled in the art from the following brief description of the drawings and detailed description of the subject matter.

DETAILED DESCRIPTION

Figure 1:
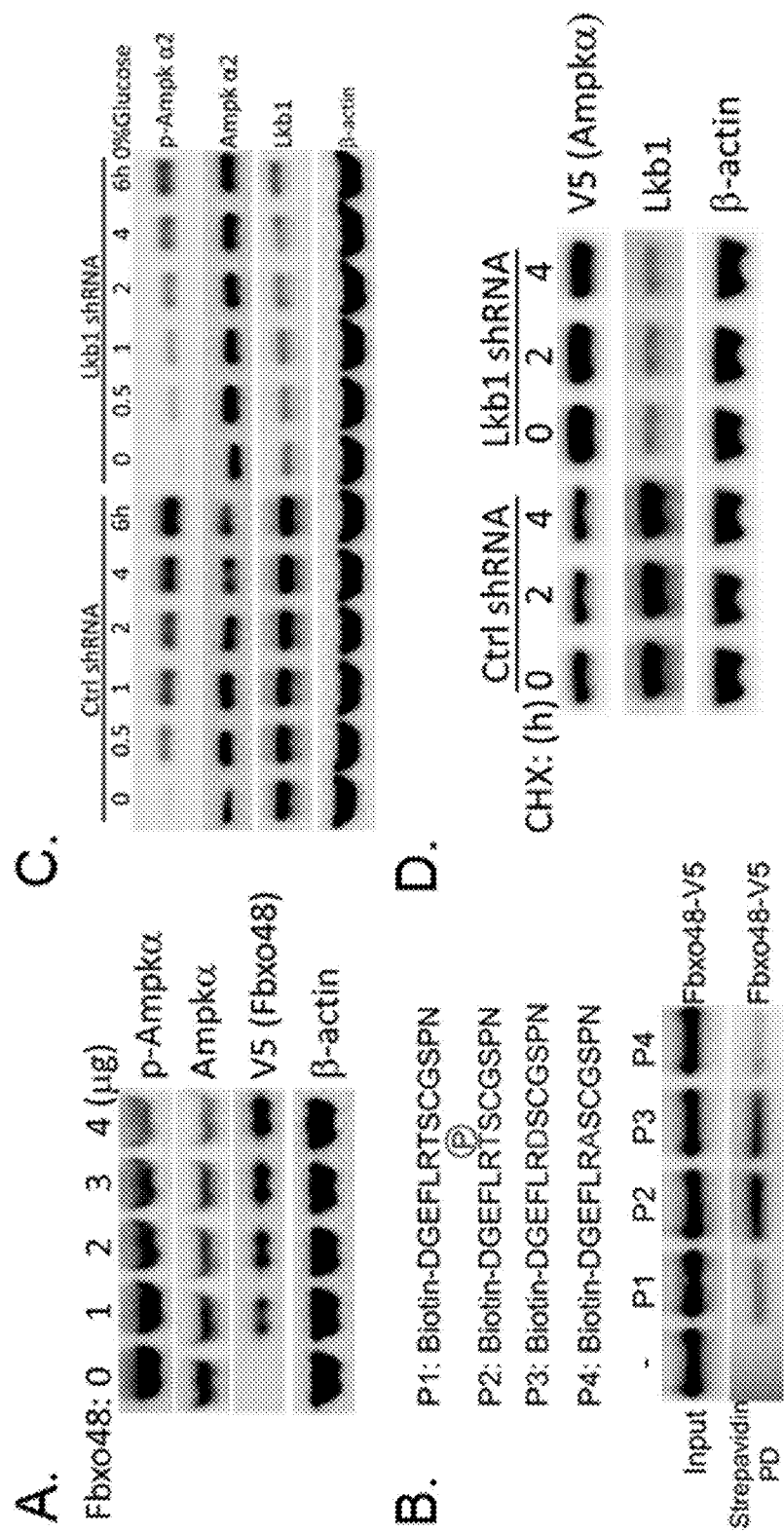
FIG. 1. (A) Human bronchial epithelial cells (Beas2b) were transfected with increasing amount of Fbxo48 plasmid. 24 h later, cells were collected for immunoblotting. (B) Biotin labeled AMPK peptides were first bound to streptavidin beads. AMPK beads were then incubated with in vitro synthesized Fbxo48 protein for 2 h. Beads were then washed, and protein was eluted before being assayed by immunoblotting. (C) Beas2B cells were transfected with either control shRNA or Lkb1 shRNA for 48 h. Cells were then exposed to 2% DMEM media without glucose before being collected for immunoblotting. (D) Beas2B cells were transfected with either control shRNA or Lkb1 shRNA for 48 h. Cells were then exposed to CHX before being assayed by immunoblotting.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

I. Compounds

Provided herein, in one aspect, are compounds of Formula I:

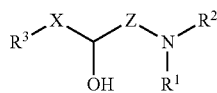

(Formula I)

wherein:

X is $C_{0-3}$ alkyl, —$(CH_2)_2$—NH—$(CH_2)_2$—, —NH—$CH_2$—, —O—$CH_2$—, —O—$(CH_2)_2$—, —$(CH_2)_2$—O—$(CH_2)_2$—, or —$(CH_2)$—$C(NH_2)$—$(CH_2)_a$—;

Z is $C_{1-2}$ alkyl, —$(CH_2)$—NH—$(CH_2)$—, —$(CH_2)$—O—$(CH_2)$—, or —$(CH_2)_a$—$C(NH_2)$—$(CH_2)$—;

a is 0 or 1;

at least one of $R^1$ and $R^2$ is —$(CHR^A)_b$—Y, wherein each $R^A$ is independently H, or a substituted or unsubstituted aryl; and b is 0 or an integer of 1-3;

the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl; or $R^1$ and $R^2$, together with the nitrogen to which they are attached, form a substituted or unsubstituted heterocyclic ring;

$R^3$ is an alkyl, carbocyclyl, aryl, or heteroaryl group, wherein each alkyl, carbocyclyl, aryl, or heteroaryl group is optionally substituted by one or more

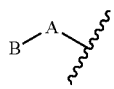

wherein:

A is C=O, SO, $SO_2$, or —$(C(R^B)_2)_d$—, wherein each $R^B$ is independently selected from H, D, halogen, OH, substituted or unsubstituted alkyl, and substituted or unsubstituted alkoxy;

d is 0 or an integer of 1-3; and

B is selected from the group consisting of substituted or unsubstituted alkyl, substituted or unsubstituted alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof.

In some embodiments of Formula I, $R^3$ is an alkyl group optionally substituted by one or more

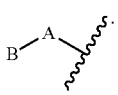

In some embodiments of Formula I, $R^3$ is an carbocyclyl group optionally substituted by one or more

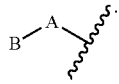

In some embodiments of Formula I, $R^3$ is an aryl group optionally substituted by one or more

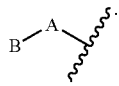

In some embodiments of Formula I, $R^3$ is an heteroaryl group optionally substituted by one or more

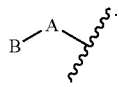

Provided herein, in another aspect, are compounds of Formula II:

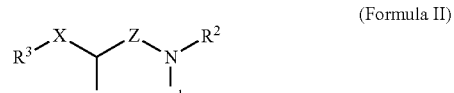

wherein:

X is $C_{0-3}$ alkyl, —$(CH_2)_2$—NH—$(CH_2)_2$—, —NH—$CH_2$—, —O—$CH_2$—, —O—$(CH_2)_2$—, —$(CH_2)_2$—O—$(CH_2)_2$—, or —$(CH_2)$—$C(NH_2)$—$(CH_2)_a$—;

Z is $C_{1-2}$ alkyl, —$(CH_2)$—NH—$(CH_2)$—, —$(CH_2)$—O—$(CH_2)$—, or —$(CH_2)_a$—$C(NH_2)$—$(CH_2)$—;

a is 0 or 1;

at least one of $R^1$ and $R^2$ is —$(CHR^A)_b$—Y, wherein each $R^A$ is independently H, or a substituted or unsubstituted aryl; and b is 0 or an integer of 1-3;

the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl; or $R^1$ and $R^2$, together with the nitrogen to which they are attached, form a substituted or unsubstituted heterocyclic ring;

$R^3$ is an aryl or heteroaryl group optionally substituted by one or more

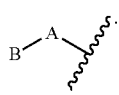

wherein:

A is C=O, SO, SO$_2$, or —(C(R$^B$)$_2$)$_d$—, wherein each R$^B$ is independently selected from H, D, halogen, OH, substituted or unsubstituted alkyl, and substituted or unsubstituted alkoxy;

d is 0 or an integer of 1-3; and

B is selected from the group consisting of C$_{1-6}$ alkyl, haloalkyl, C$_{1-6}$ alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof.

In some embodiments of Formula I or Formula II, R$^3$ is unsubstituted phenyl, unsubstituted naphthyl, or phenyl substituted with one or two

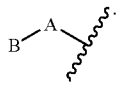

In some embodiments of Formula I or Formula II, R$^3$ is unsubstituted phenyl or phenyl substituted with one

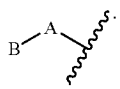

In some embodiments of Formula I or Formula II, R$^3$ is phenyl substituted with one

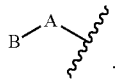

In some embodiments of Formula I or Formula II, R$^3$ is phenyl substituted with two

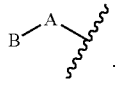

In some embodiments of Formula I or Formula II, R$^3$ is unsubstituted phenyl. In some embodiments of Formula I or Formula II, R$^3$ is unsubstituted naphthyl.

In some embodiments of Formula I or Formula II, A is —(C(R$^B$)$_2$)$_d$—. In some embodiments of Formula I or Formula II, R$^B$ is H, or substituted or unsubstituted alkyl. In some embodiments of Formula I or Formula II, R$^B$ is H. In some embodiments of Formula I or Formula II, R$^B$ is substituted or unsubstituted alkyl. In some embodiments of Formula I or Formula II, R$^B$ is substituted alkyl. In some embodiments of Formula I or Formula II, R$^B$ is alkyl. In some embodiments of Formula I or Formula II, d is 0. In some embodiments of Formula I or Formula II, d is an integer of 1-3. In some embodiments of Formula I or Formula II, d is 1. In some embodiments of Formula I or Formula II, d is 2. In some embodiments of Formula I or Formula II, d is 3.

In some embodiments of Formula I or Formula II, A is C=O. In some embodiments of Formula I or Formula II, A is SO or SO$_2$. In some embodiments of Formula I or Formula II, A is SO. In some embodiments of Formula I or Formula II, A is SO$_2$.

In some embodiments of Formula I or Formula II, B is selected from the group consisting of C$_{2-6}$ alkyl, haloalkyl, C$_{2-6}$ alkoxy, substituted or unsubstituted aryl, substituted or unsubstituted carbocyclyl, substituted or unsubstituted heterocyclyl, and substituted or unsubstituted heteroaryl.

In some embodiments of Formula I or Formula II, B is selected from the group consisting of C$_{2-6}$ alkyl, haloalkyl, C$_{2-6}$ alkoxy, substituted or unsubstituted phenyl, substituted or unsubstituted C$_{3-8}$ carbocyclyl, and substituted or unsubstituted six-membered heteroaryl. In further embodiments of Formula I or Formula II, the substituted or unsubstituted six-membered heteroaryl is a substituted or unsubstituted pyridine In some embodiments of Formula I or Formula II, B is selected from the group consisting of haloalkyl, C$_{2-6}$ alkoxy, substituted or unsubstituted phenyl, C$_{3-8}$ carbocyclyl, and substituted or unsubstituted six-membered heteroaryl. In further embodiments of Formula I or Formula II, the substituted or unsubstituted six-membered heteroaryl is a substituted or unsubstituted pyridine.

In some embodiments of Formula I or Formula II, X is C$_{0-3}$ alkyl, —NH—CH$_2$—, or —O—CH$_2$—. In some embodiments of Formula I or Formula II, X is C$_{0-3}$ alkyl. In some embodiments of Formula I or Formula II, X is C$_0$ alkyl. In some embodiments of Formula I or Formula II, X is C$_{1-3}$ alkyl. In some embodiments of Formula I or Formula II, X is C$_1$ alkyl.

In some embodiments of Formula I or Formula II, X is C$_2$ alkyl. In some embodiments of Formula I or Formula II, X is C$_3$ alkyl. In some embodiments of Formula I or Formula II, X is CH$_2$CH$_2$. In some embodiments of Formula I or Formula II, X is —NH—CH$_2$—. In some embodiments of Formula I or Formula II, X is —O—CH$_2$—.

In some embodiments of Formula I or Formula II, Z is C$_{1-2}$ alkyl. In some embodiments of Formula I or Formula II, Z is C$_1$ alkyl. In some embodiments of Formula I or Formula II, Z is CH$_2$. In some embodiments of Formula I or Formula II, Z is C$_2$ alkyl.

In some embodiments of Formula I or Formula II, at least one of R$^1$ and R$^2$ is —(CHR$^A$)$_b$—Y, wherein each R$^A$ is independently H, or a substituted or unsubstituted aryl; and b is 0 or an integer of 1-3; the remaining one of R$^1$ and R$^2$ is —(CH$_2$)$_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl. In further embodiments of Formula I or Formula II, the remaining one of R$^1$ and R$^2$ is —(CH$_2$)$_c$—Y or selected from the group consisting of H, substituted or unsubstituted alkyl, substituted or unsubstituted aryl, and substituted or unsubstituted carbocyclyl; and c is 0 or an integer of 1-3. In still further embodiments of Formula I or Formula II, the remaining one of R$^1$ and R$^2$ is —(CH$_2$)$_c$—Y or H; and c is 0 or an integer of 1-3. In still further embodiments of Formula I or Formula II, the remaining one of R$^1$ and R$^2$ is —(CH$_2$)$_c$—Y or H; and c is 0 or 1. In still further embodiments of Formula I or Formula II, b is 0 or 1; and the remaining one of R$^1$ and R$^2$ is —(CH$_2$)—Y or H. In some embodiments of Formula I or Formula II, each R$^A$ is independently H, or a substituted or unsubstituted phenyl; b is 0 or 1; the remaining one of $R^1$ and $R^2$ is —(CH$_2$)—Y or H; and each Y is a substituted or unsubstituted phenyl.

In some embodiments of Formula I or Formula II, at least one of $R^1$ and $R^2$ is —(CHR$^4$)—Y, wherein $R^4$ is a substituted or unsubstituted phenyl; the remaining one of $R^1$ and $R^2$ is H; and each Y is independently a substituted or unsubstituted phenyl.

In some embodiments of Formula I or Formula II, at least one of $R^1$ and $R^2$ is —(CH$_2$)—Y; the remaining one of $R^1$ and $R^2$ is —(CH$_2$)—Y; and each Y is independently a substituted or unsubstituted aryl. In some embodiments of Formula I or Formula II, at least one of $R^1$ and $R^2$ is —(CH$_2$)—Y; the remaining one of $R^1$ and $R^2$ is —(CH$_2$)—Y; and each Y is independently a substituted or unsubstituted phenyl.

In some embodiments of Formula I or Formula II, at least one of $R^1$ and $R^2$ is —(CH$_2$CHR$^4$)—Y, wherein $R^4$ is H, or a substituted or unsubstituted aryl; the remaining one of $R^1$ and $R^2$ is H; and Y is a substituted or unsubstituted aryl. In some embodiments of Formula I or Formula II, at least one of $R^1$ and $R^2$ is —(CH$_2$CHR$^4$)—Y, wherein $R^4$ is H, or a substituted or unsubstituted aryl; the remaining one of $R^1$ and $R^2$ is H; and Y is a substituted or unsubstituted phenyl.

In some embodiments of Formula I or Formula II, $R^4$ is H. In some embodiments of Formula I or Formula II, $R^4$ is phenyl. In some embodiments of Formula I or Formula II, $R^4$ is substituted phenyl.

In some embodiments of Formula I or Formula II, b is 3. In some embodiments of Formula I or Formula II, b is 2. In some embodiments of Formula I or Formula II, b is 1. In some embodiments of Formula I or Formula II, b is 0.

In some embodiments of Formula I or Formula II, the remaining one of $R^1$ and $R^2$ is —(CH$_2$)—Y. In some embodiments of Formula I or Formula II, the remaining one of $R^1$ and $R^2$ is H.

In some embodiments of Formula I or Formula II, $R^1$ and $R^2$, together with the nitrogen to which they are attached, form a substituted or unsubstituted heterocyclic ring. In further embodiments of Formula I or Formula II, $R^1$ and $R^2$, together with the nitrogen to which they are attached, form a substituted or unsubstituted tetrahydroisoquinoline.

Provided herein, in another aspect, are compounds selected from the group consisting of:

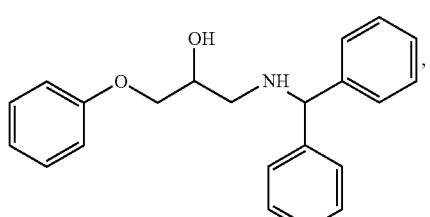

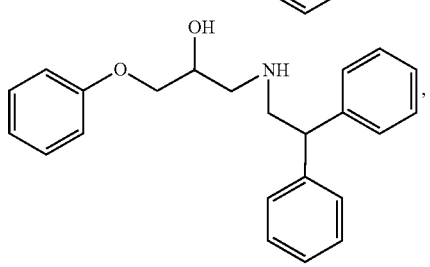

-continued

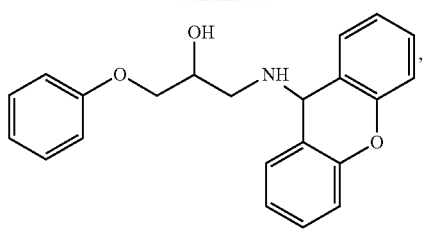

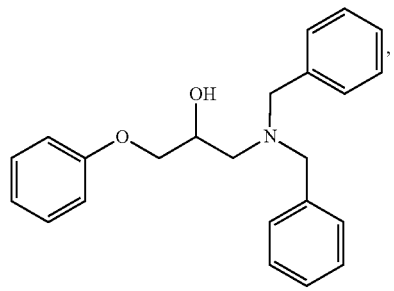

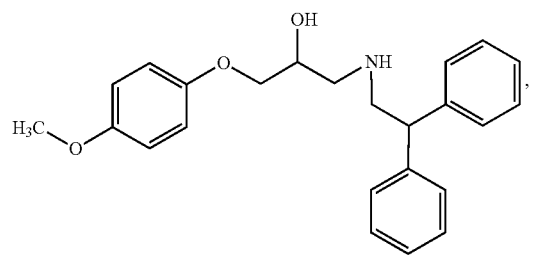

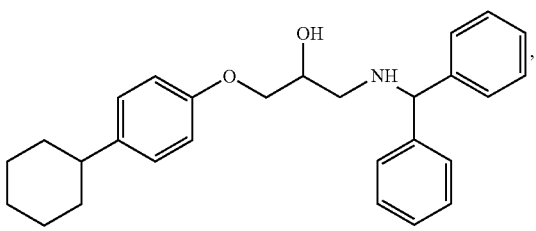

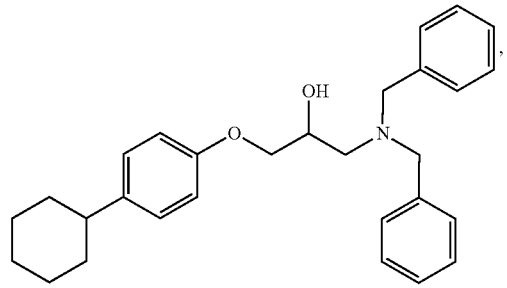

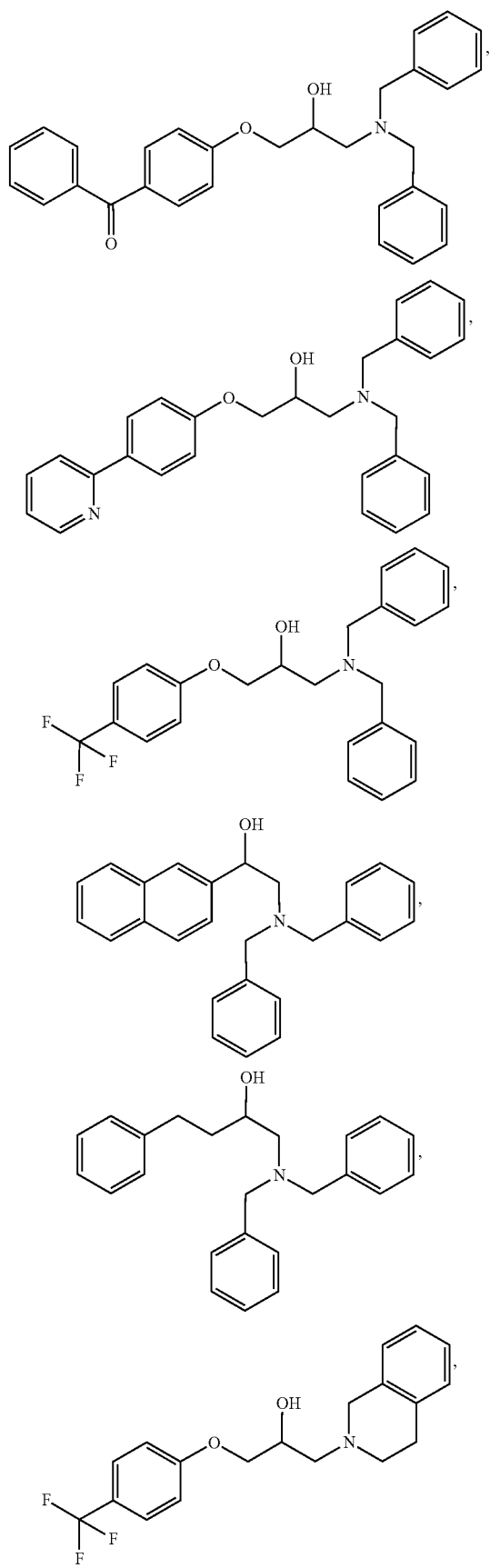
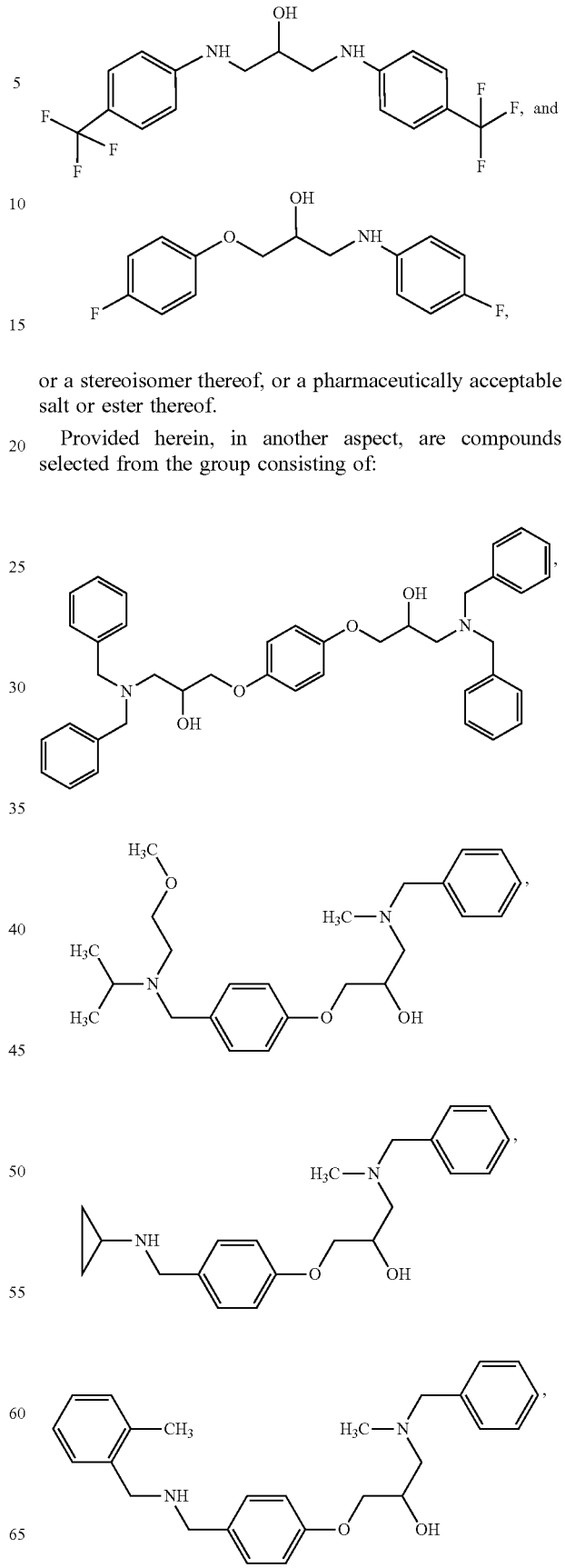
or a stereoisomer thereof, or a pharmaceutically acceptable salt or ester thereof.
Provided herein, in another aspect, are compounds selected from the group consisting of:

or a stereoisomer thereof, or a pharmaceutically acceptable salt or ester thereof.

II. Methods of Use

Provided herein, in another aspect, are methods to bind a ubiquitin E3 ligase, the method comprising contacting the ubiquitin E3 ligase with a compound of Formula I or II, or a stereoisomer thereof, or a pharmaceutically acceptable salt or ester thereof.

Provided herein, in another aspect, are methods to treat inflammation in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to treat cytokine-driven inflammation in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to treat inflammatory disorders in a subject in need thereof, the method comprising administering to the subject a therapeutically effective amount of a compound of Formula I or II, or a stereoisomer thereof, or a pharmaceutically acceptable salt or ester thereof. Inflammatory disorders that may be treated by the compounds disclosed herein include any disorder possessing an inflammatory component. Illustrative inflammatory disorders include acute and chronic inflammation disorders such as asthma, chronic obstructive lung disease, pulmonary fibrosis, pneumonitis (including hypersensitivity pneumonitis and radiation pneumonitis), pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (Crohn's disease, ulcerative colitis)/colitis, sepsis, vasculitis, bursitis, connective tissue disease, autoimmune diseases such as systemic lupus erythematosis (SLE), polymyalgia rheumatica, scleroderma, Wegener's granulomatosis, temporal arteritis, vasculitis, cryoglobulinemia, and multiple sclerosis, viral or influenza-induced inflammation, or edema. The compounds disclosed herein may be particularly effective for treating sepsis, pneumonia, influenza-induced inflammation, edema, neuropathy, colitis, arthritis, Crohn's disease, diabetes, skin, eye and ear inflammation (e.g., psoriasis, uveitis/opthalmitis, external otitis), systemic lupus erythematosis (SLE), and systemic lupus erythematosis (SLE). The compounds disclosed herein may be useful for treating neurological diseases such as Alzheimer, Parkinson, and neuropathy pain. The compounds disclosed herein may also be useful for treating inflammation and tissue damage induced by pathogenic infection with, for example, *Pseudomonas aeruginosa, Staphylococcus aureus, Streptococcus pneumoniae, Haemophilus influenza,* or *Escherichia coli*. The compounds disclosed herein may be especially effective for treating sepsis or pneumonia.

Provided herein, in another aspect, are methods to treat sepsis in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to treat pneumonia in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to treat acute lung injury in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to treat metabolic syndrome in a subject in need thereof, the method comprising administering to the subject a therapeutically effective amount of a compound of Formula I or II, or a stereoisomer thereof, or a pharmaceutically acceptable salt or ester thereof.

Provided herein, in another aspect, are methods to increase the level of phosphorylated-AMPK in a subject in need thereof, the method comprising administering to the subject a therapeutically effective amount of a compound of Formula I or II, or a stereoisomer thereof, or a pharmaceutically acceptable salt or ester thereof 6.

Provided herein, in another aspect, are methods to disrupt interaction between Fbxo48 and phosphorylated-AMPK in a cell, the method comprising contacting the cell with a compound of Formula I or II, or a stereoisomer thereof, or a pharmaceutically acceptable salt or ester thereof.

Provided herein, in another aspect, are methods to disrupt interaction between Fbxo48 and phosphorylated-AMPK in a subject in need thereof, the method comprising administering to the subject a therapeutically effective amount of a compound of Formula I or II, or a stereoisomer thereof, or a pharmaceutically acceptable salt or ester thereof.

Compounds represented by Formula I or Formula II, or pharmaceutically acceptable salts or solvates thereof, or a composition comprising such a compound or a pharmaceutically acceptable salt or solvate thereof, can be administered to a patient or subject in need of treatment either individually, or in combination with other therapeutic agents that have similar or synergistic biological activities. Additionally, the compounds and compositions described herein can be administered as a single dose or as multiple daily doses by a practicing medical practitioner.

A composition comprising a compound of the present disclosure may be administered to individuals in a formulation with one or more pharmaceutically acceptable excipient(s). Wide varieties of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In the subject methods, the active agent(s) may be administered to the patient or subject using any convenient means capable of resulting in the desired therapeutic effect. Thus, the agent can be incorporated into a variety of formulations for therapeutic administration. More particularly, the agents of the present subject matter can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including but not limited to oral, buccal, rectal, parenteral, intraperitoneal, intradermal, topical, pulmonary, nasal, inhalation, transdermal, intracheal, etc., administration.

The dosage administered will be dependent upon multiple factors, such as the age, health, weight, and/or disease state of the recipient, kind of concurrent treatment, if any, frequency of treatment, and/or the nature and magnitude of the biological effect desired. An exemplary dosage may be about 0.1-about 20 mg/kg/d, or any amount in between these two amounts. Other exemplary dosages include, but are not limited to, about 0.1 to about 10 mg/kg/d or about 0.5 to about 10 mg/kg/d. Still other exemplary dosages include, but are not limited to, about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, or about 20 mg/kg/d. When combination therapy is used, the compound and the other therapeutic agent can be administered separately at different time intervals, or simultaneously.

III. Pharmaceutical Formulations

Pharmaceutical compositions and medicaments may be prepared by mixing one or more compounds described herein, prodrugs thereof, pharmaceutically acceptable salts or solvates thereof, stereoisomers thereof, tautomers thereof, or solvates thereof, with pharmaceutically acceptable carriers, excipients, binders, diluents or the like.

In the subject methods, the active agent(s) may be administered to the host using any convenient means capable of resulting in the desired therapeutic effect Thus, the agent can be incorporated into a variety of formulations for therapeutic administration. More particularly, the agents of the present subject matter can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The compounds and compositions disclosed herein may be used to prepare formulations and medicaments that prevent or treat cytokine-driven inflammation, as described herein. In some embodiments, the compounds and compositions disclosed herein may be used to prepare formulations and medicaments that prevent or treat inflammatory disorders described herein. In some embodiments, the compounds and compositions disclosed herein may be used to prepare formulations and medicaments that prevent or treat sepsis. In some embodiments, the compounds and compositions disclosed herein may be used to prepare formulations and medicaments that prevent or treat pneumonia. In some embodiments, the compounds and compositions disclosed herein may be used to prepare formulations and medicaments that prevent or treat acute lung injury.

Such compositions can be in any pharmaceutically acceptable form, such as but not limited to in the form of, for example, granules, powders, tablets, capsules, syrup, suppositories, injections, emulsions, elixirs, suspensions or solutions. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The following dosage forms are given by way of example and should not be construed as limiting the present subject matter.

Pharmaceutically acceptable salts of the compounds disclosed herein are considered within the scope of the present technology. The compounds disclosed herein have a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds disclosed herein may have acidic substituent groups, and in such cases, it can form salts with metals, such as alkali and earth alkali metals (e.g., $Na^+$, $Li^+$, $K^+$, $Ca^{2+}$, $Mg^{2+}$, $Zn^{2+}$), organic amines (e.g., ammonia, trimethylamine, triethylamine, pyridine, picoline, ethanolamine, diethanolamine, triethanolamine) or basic amino acids (e.g., arginine, lysine and omithine).

Certain compounds within the scope of the technology disclosed herein are derivatives referred to as prodrugs. The expression "prodrug" denotes a derivative of a known direct acting drug, e.g., esters and amides, which derivative has enhanced delivery characteristics and therapeutic value as compared to the drug, and is transformed into the active drug by an enzymatic or chemical process; see Notari, R. E., "Meory and Practice of Prodrug Kinetics," *Methods in Enzymology*, 112: 309-23 (1985); Bodor, N., "Novel Approaches in Prodrug Design," *Drugs of the Future*, 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), and Goodman and Gilmans, *The Pharmacological Basis Of Therapeutics*, 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds described herein, or pharmaceutically acceptable salts or tautomers thereof, with at least one additive such as a starch or other additive. Suitable additives include any pharmaceutically acceptable excipient, including but not limited to sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can comprise other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

The present subject matter, thus generally described, will be understood more readily by reference to the following examples, which are provided by way of illustration and are not intended to be limiting of the present subject matter.

IV. Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In certain embodiments, an alkyl comprises two to eight carbon atoms (e.g., $C_2$-$C_8$ alkyl). In certain embodiments, an alkyl comprises two to six carbon atoms (e.g., $C_2$-$C_6$ alkyl). In certain embodiments, an alkyl comprises one to three carbon atoms (e.g., $C_1$-$C_3$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. In some embodiments, a substituted alkyl group is substituted by one or more of the following substituents: halo, cyano, nitro, oxo, thioxo, —$OR^a$, —$SR^a$, —OC(O)—$R^b$, —$N(R^a)_2$, —$C(O)R^a$, —$C(O)OR^a$, —$C(O)N(R^a)_2$, —$N(R^a)C(O)OR^a$, —$N(R^a)C(O)R^a$, $N(R^a)S(O)_2R^b$, —$S(O)_2OR^a$ and —$S(O)_2N(R^8)_2$ where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each $R^b$ is independently alkyl, fluoroalkyl, carbocyclyl, carbocyclylalkyl, aryl, aralkyl, heterocyclyl, heterocyclylalkyl, heteroaryl or heteroarylalkyl.

The term "alkoxy," as used herein, refers to an alkyl ether radical, wherein the term alkyl is as defined herein. Non-limiting examples of suitable alkyl ether radicals include methoxy, ethoxy, n-propoxy, isopropoxy, n-butoxy, iso-butoxy, sec-butoxy, tert-butoxy, cyclopentoxy, and the like.

The term "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. In some embodiments, aryl group has 6- to 10-carbon atoms. Aryl groups include, but are not limited to, groups such as phenyl, fluorenyl, and naphthyl. In some embodiments, the term "substituted aryl" is meant to include aryl radicals substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—OC(O)—$R^b$, —$R^c$—$N(R^a)_2$, —$R^c$—$C(O)R^a$, —$R^c$—$C(O)OR^a$, —$R^c$—$C(O)N(R^a)_2$, —$R^c$—O—$R^d$—$C(O)N(R^a)_2$, —$R^c$—$N(R^8)C(O)OR^a$, —$R^c$—$N(R^a)C(O)R^a$, —$R^c$—$N(R^a)S(O)_2R^b$, —$R^c$—$S(O)_2OR^a$ and —$R^c$—$S(O)_2N(R^a)_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, each $R^c$ is independently a direct bond or a straight or branched alkylene, alkenylene, or alkynylene chain, and $R^d$ is a straight or branched alkylene, alkenylene, or alkynylene chain, and where each of the above substituents is unsubstituted unless otherwise indicated.

The term "carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In some embodiments, a carbocyclyl comprises five to seven carbon atoms. In some embodiments, a carbocyclyl comprises four to seven carbon atoms. In some embodiments, a carbocyclyl comprises five to six carbon atoms. The carbocyclyl is attached to the rest of the molecule by a single bond. Carbocyclyl may be saturated, (i.e., containing single C—C bonds only) or unsaturated (i.e., containing one or more double bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl,7,7-dimethyl-bicyclo[2.2.1]heptanyl, and the like. In some embodiments, the term "substituted carbocyclyl" is meant to include carbocyclyl radicals that are substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—$N(R^a)_2$, —$R^c$—$C(O)R^a$, —$R^c$—$C(O)OR^a$, —$R^c$—$C(O)N(R^a)_2$, —$R^c$—O—$R^d$—$C(O)N(R^a)_2$, —$R^c$—$N(R^a)C(O)OR^a$, —$R^c$—$N(R^a)C(O)R^a$, —$R^c$—$N(R^a)S(O)_2R^b$, —$R^c$—$S(O)_2OR^a$ and —$R^c$—$S(O)_2N(R^a)_2$ where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The term "halo," or "halogen," as used herein, refers to fluorine, chlorine, bromine, or iodine. In some embodiments, the halogen may be selected from fluorine, chlorine, or bromine, individually fluorine or chlorine or bromine.

The term "haloalkyl," as used herein, refers to an alkyl radical substituted with one or more halo radicals, as defined above, wherein the term alkyl is as defined herein. Non-limiting examples of haloalkyl include trifluoromethyl, difluoromethyl, 2,2,2-trifluoroethyl, 1-fluoromethyl-2-fluoroethyl, and the like.

The term "heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In some embodiments, the heteroatom(s) in the heteroaryl radical is optionally oxidized. In some embodiments, one or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). In some embodiments, the term "substituted heteroaryl" is meant to include heteroaryl radicals as defined above which are substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—N($R^a$)$_2$, —$R^c$—C(O)$R^a$, —$R^c$—C(O)O$R^a$, —$R^c$—C(O)N($R^a$)$_2$, —$R^c$—O—$R^d$—C(O)N($R^a$)$_2$, —$R^c$—N(R)C(O)O$R^a$, —$R^c$—N($R^a$)C(O)$R^a$, —$R^c$—N($R^a$)S(O)$_2R^b$, —$R^c$—S(O)$_2$O$R^a$ and —$R^c$—S(O)$_2$N($R^a$)$_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The term "heterocyclyl" refers to a stable 4- to 18-membered non-aromatic ring radical that comprises three to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. In some embodiments, one or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the term "substituted heterocyclyl" is meant to include heterocyclyl radicals as defined above that are substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—N($R^a$)$_2$, —$R^c$—C(O)$R^a$, —$R^c$—C(O)O$R^a$, —$R^c$—C(O)N($R^a$)$_2$, —$R^c$—O—$R^d$—C(O)N($R^a$)$_2$, —$R^c$—N($R^a$)C(O)O$R^a$, —$R^c$—N($R^a$)C(O)$R^a$, —$R^c$—N($R^a$)S(O)$_2R^b$, —$R^c$—S(O)$_2$O$R^a$ and —$R^c$—S(O)$_2$N($R^8$)$_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each Rb is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The terms "optional" or "optionally" mean that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "stereoisomers" is a general term for all isomers of individual molecules that differ only in the orientation of their atoms in space. It includes enantiomers and isomers of compounds with more than one chiral center that are not mirror images of one another (diastereomers).

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

As used herein, the term "tautomers" refers to particular isomers of a compound in which a hydrogen and double bond have changed position with respect to the other atoms of the molecule. Examples of tautomers include keto-enol forms, imine-enamine forms, amide-imino alcohol forms, amidine-aminidine forms, nitroso-oxime forms, thio ketoneenethiol forms, N-nitroso-hydroxyazo forms, nitro-aci-nitro forms, and pyridione-hydroxypyridine forms.

The term "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

The term "patient" refers to any animal for which treatment is desirable. Patients may be mammals, and typically, as used herein, a patient is a human individual.

The term "pharmaceutically acceptable salt," as used herein, represents salts or zwitterionic forms of the compounds of the present subject matter which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present subject matter can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present subject matter contemplates sodium, potassium, magnesium, and calcium salts of the compounds of the present subject matter and the like.

An "effective" amount of an agent is meant to mean an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "solvates" is used in its broadest sense. For example, the term solvates includes hydrates formed when a compound of the present subject matter contains one or more bound water molecules.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

The following examples are given to illustrate the present subject matter. It should be understood, however, that the subject matter is not to be limited to the specific conditions or details described in these examples.

EXAMPLES

Example 1. Initial Experiments

Through screening, it was determined that SCF subunit Fbxo48 expression regulates AMPK protein stability (data not shown). Specifically, Fbxo48 ectopic expression dose dependently decreased AMPK and phospho-AMPK levels (FIG. 1A). Further, the specific binding region between Fbxo48 and AMPK, which contains the key residue T172 that is required for AMPK phosphorylation and activation, was identified. A peptide binding experiment was performed in which the biotin-labeled peptide derived from AMPK was used as the bait to pull-down Fbxo48. Interestingly, Fbxo48 showed drastically more interaction with peptide 2 in which the T172 residue is phosphorylated. A similar binding pattern was observed with peptide 3 in which T172 was mutated to glutamic acid as a phospho-mimic (FIG. 1B). These experiments suggested that Fbxo48 targets phospho-AMPK at the T172 site. Further, the upstream molecular pathway was investigated by knocking down Lkb1 using shRNA. As shown in FIG. 1C, cell starvation promotes AMPK phosphorylation, which in turn decreases AMPK total protein. However, Lkb1 knockdown drastically reduced the AMPK phosphorylation level and stabilized AMPK total protein. Further, it was showed that Lkb1 shRNA stabilized AMPK protein using CHX chase (FIG. 1D).

Example 2. In Silico Screening

Figure 2:
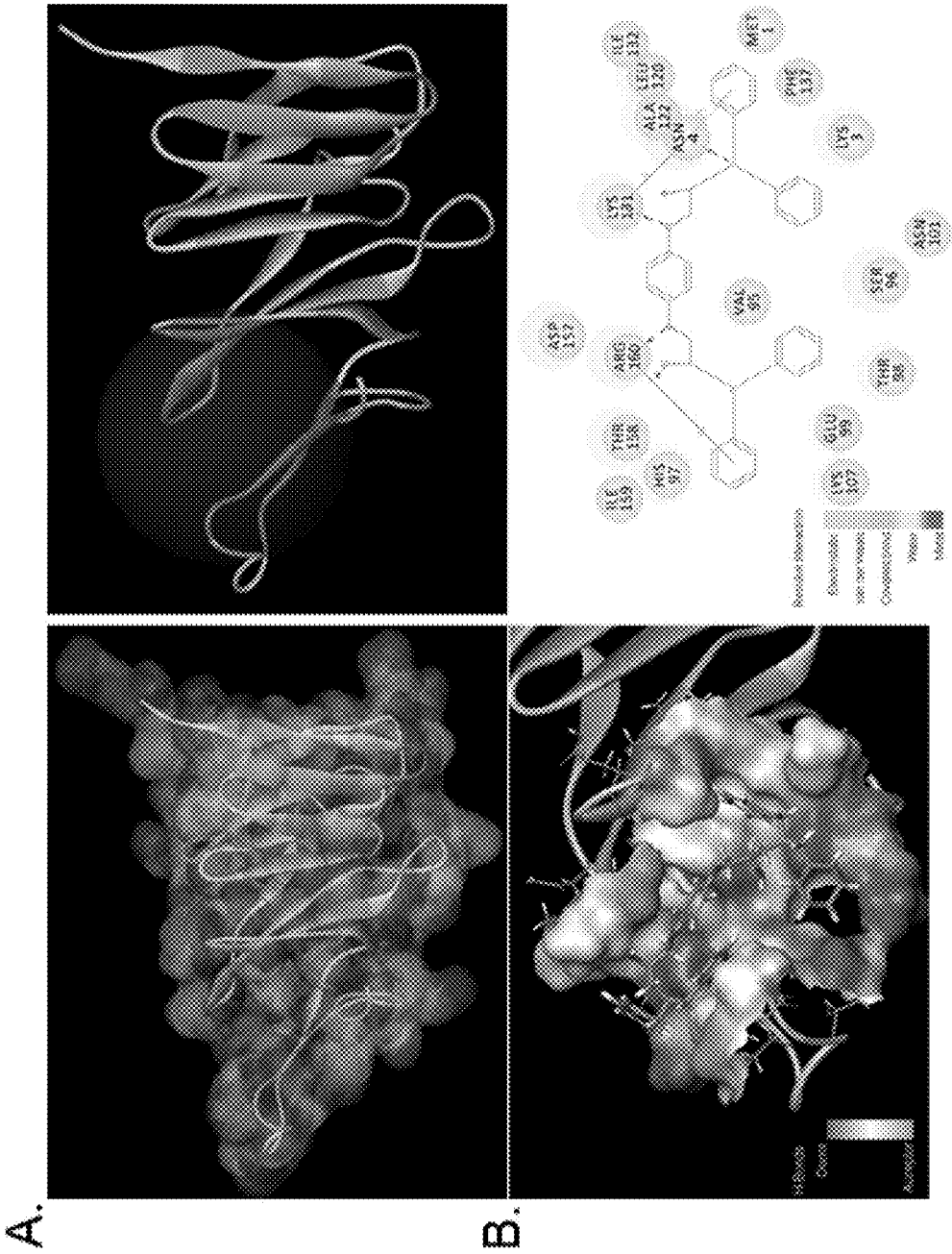
FIG. 2. (A) Fbxo48 protein homology model. Large sphere indicates a potential drug binding cavity within Fbxo48. (B) Docking study of candidate inhibitor Compound 1 with the Fbxo48 cavity.

Using molecular docking analysis and score-ranking operations, potential ligands were assessed that might fit the Fbxo48 domain cavities (FIG. 2A). Through the LibDock program from Discovery Studio 3.5, 3 million potential ligands were virtually screened for the Fbxo48 pocket. After this initial round of screening, Compound 1 (Table 1) was identified. FIG. 2B shows the in silico docking model of Compound 1 bound to Fbxo48.

Example 3. In Vitro Studies of Compound 1 (BC1583)

Figure 3:
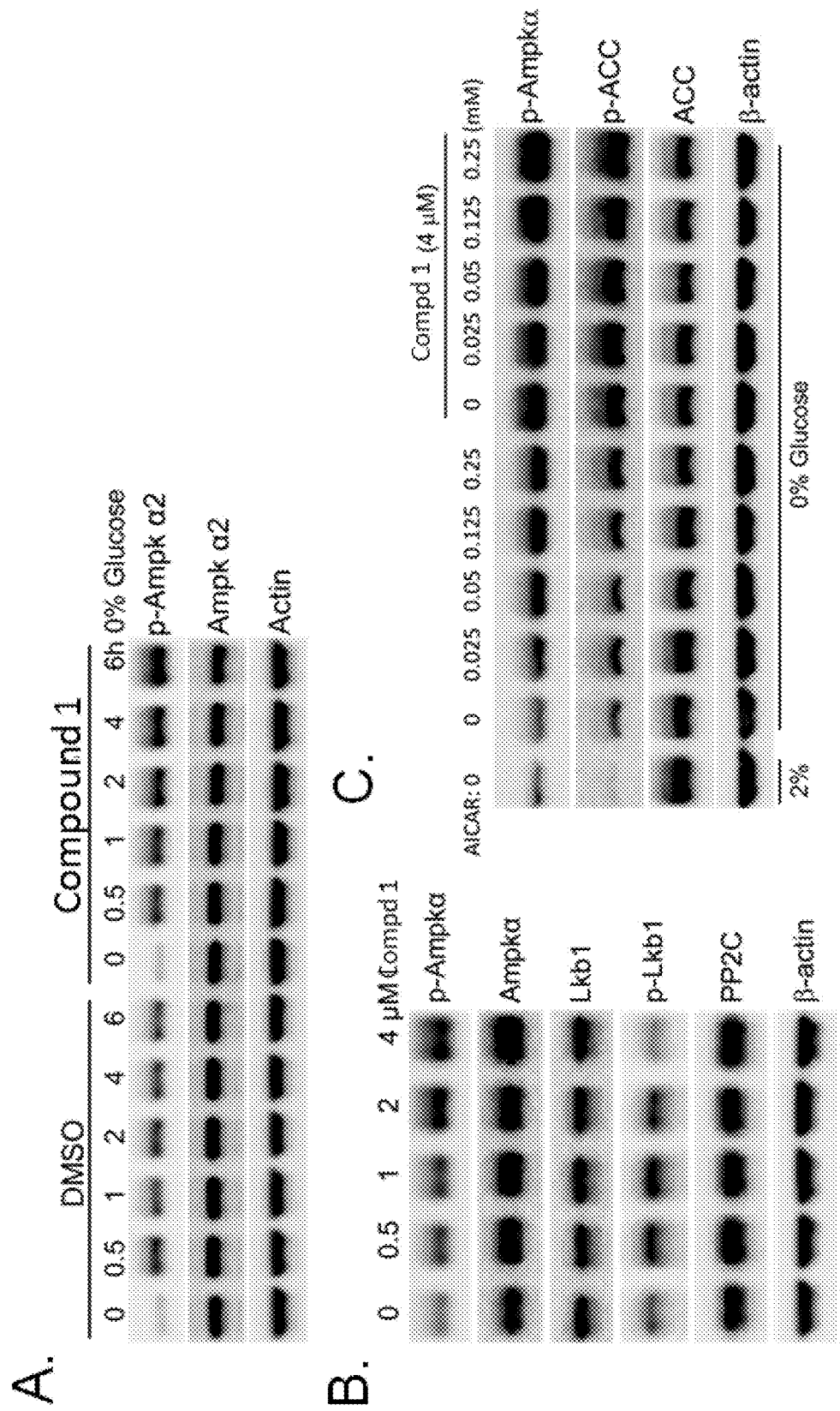
FIG. 3. (A) Beas2b cells were cultured in DMEM 2% media with glucose for 24 h before switching to glucose-free media. Cells were then exposed to either DMSO or Compound 1 (2 µM) in a time course before being collected for immunoblotting. (B) Beas2B cells were exposed to Compound 1 for 18 h at various doses before being collected for immunoblotting. (C) Beas2b cells were cultured in DMEM 2% media with glucose for 24 h before switching to glucose-free media. Cells were then exposed to AICAR at various doses with or without Compound 1 co-treatment. After 18 h, cells were collected before being assayed by immunoblotting.

Compound 1 was studied in in vitro assays using Beas2B cells. Compound 1 drastically increased phospho-AMPK levels within 2 h compared to vehicle control (FIG. 3A). Next, Compound 1 was tested in Beas2B cells in a dose-dependent manner, leading to a drastic increase in phospho-AMPK levels at 2 µM (FIG. 3B). Further, the synergistic effect of Compound 1 with known AMPK activator AICAR was examined. As shown in FIG. 3C, AICAR increased phospho-AMPK levels in a dose dependent manner, but at very high concentration ~0.05 mM. However, when co-treating cells with both AICAR and Compound 1, Compound 1 at 4 µM completely saturated AICAR effects. Compound 1 alone at 4 µM increased phospho-AMPK and downstream p-ACC levels, well exceeding AICAR treatment at 0.25 mM (FIG. 3C).

Example 4. Hit to Lead Identification and In Vitro Characterization

Figure 4:
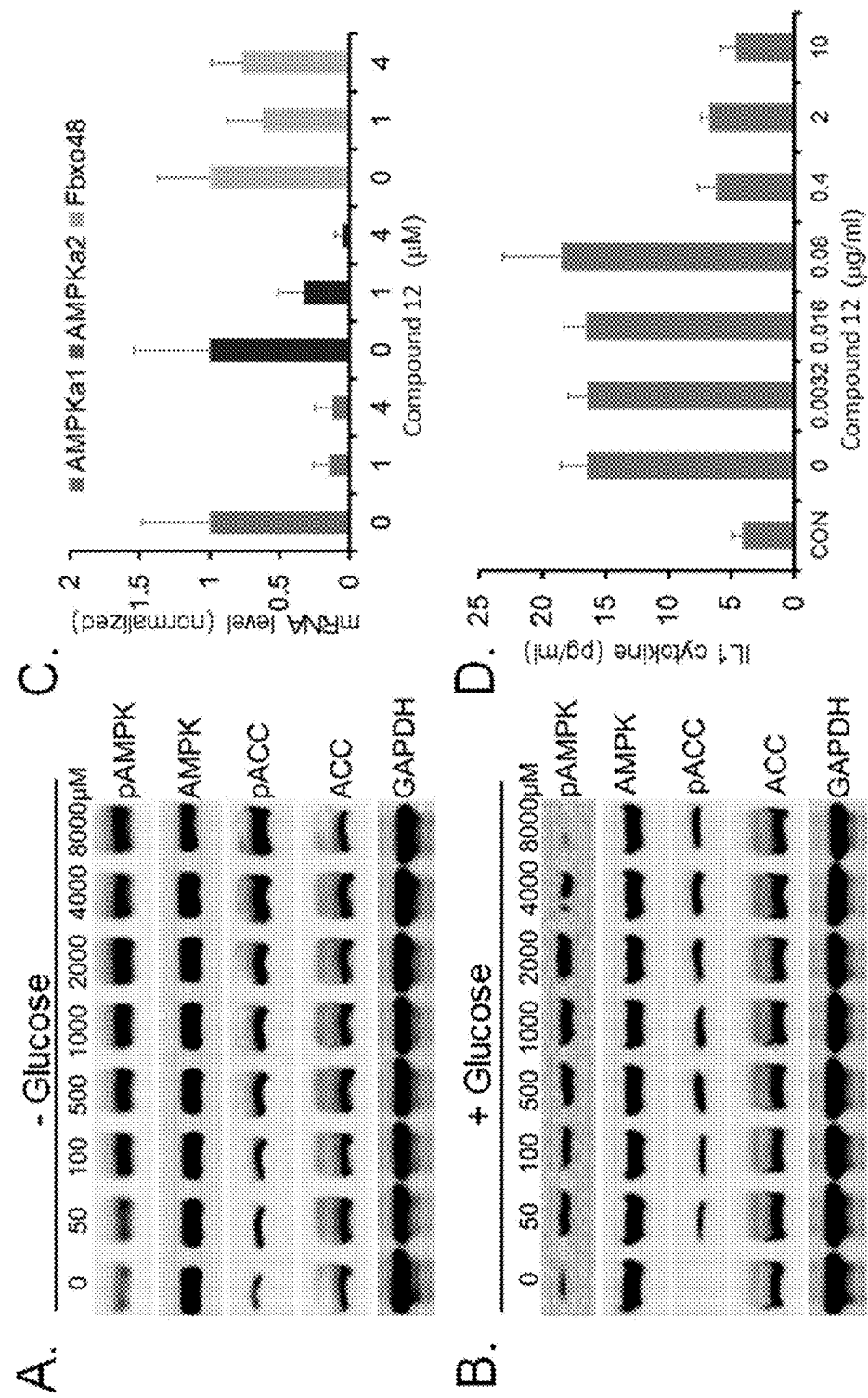
FIG. 4. (A) Beas2b cells were cultured in DMEM 2% media with glucose for 24 h before switching to glucose-free media. Cells were then exposed to Compound 12 in a dose dependent manner for 18 h before being collected for immunoblotting. (B) Beas2b cells were cultured in DMEM 2% media with glucose for 24 h before Compound 12 treatment in a dose dependent manner. After 18 h, cells were then collected for immunoblotting. (C) Beas2b cells were cultured in DMEM 2% media with glucose for 24 h before switching to glucose-free media. Cells were then exposed to Compound 12 for 18 h before being collected for mRNA analysis. (D) 50K PBMC cells were cultured in 96 well plates before being exposed to Compound 12 for 4 h. Cells were then treated with LPS (10 ng/ml) for additional 2 h. Media were then collected and IL-1b concentration was determined by ELISA.

A SAR study was performed by constructing analogs of Compound 1. One of these compounds, Compound 12 (BC1609), showed an even more improved activity towards AMPK phosphorylation. At 100-500 nM, Compound 12 effectively increased both phospho-AMPK and downstream p-ACC levels with or without glucose (FIGS. 4A-B). Compound 12 effectively decreased mRNA levels of both AMPKα1 and AMPKα2, suggesting a cellular compensation mechanism due to high level of active AMPK (FIG. 4C). This also suggests that Compound 12 is an authentic activator of AMPK. Compound 12 was further tested in PBMCs. Briefly, PBMCs were treated with Compound 12 at various concentrations for 4 h before exposure to LPS (10 ng/ml) for 2 h. Compound 12 was observed to potently inhibit LPS induced IL-1 release from PBMCs (FIG. 4D).

Example 5. Compound 12 (BC1609) in LPS-Induced Sepsis Model

Figure 5:
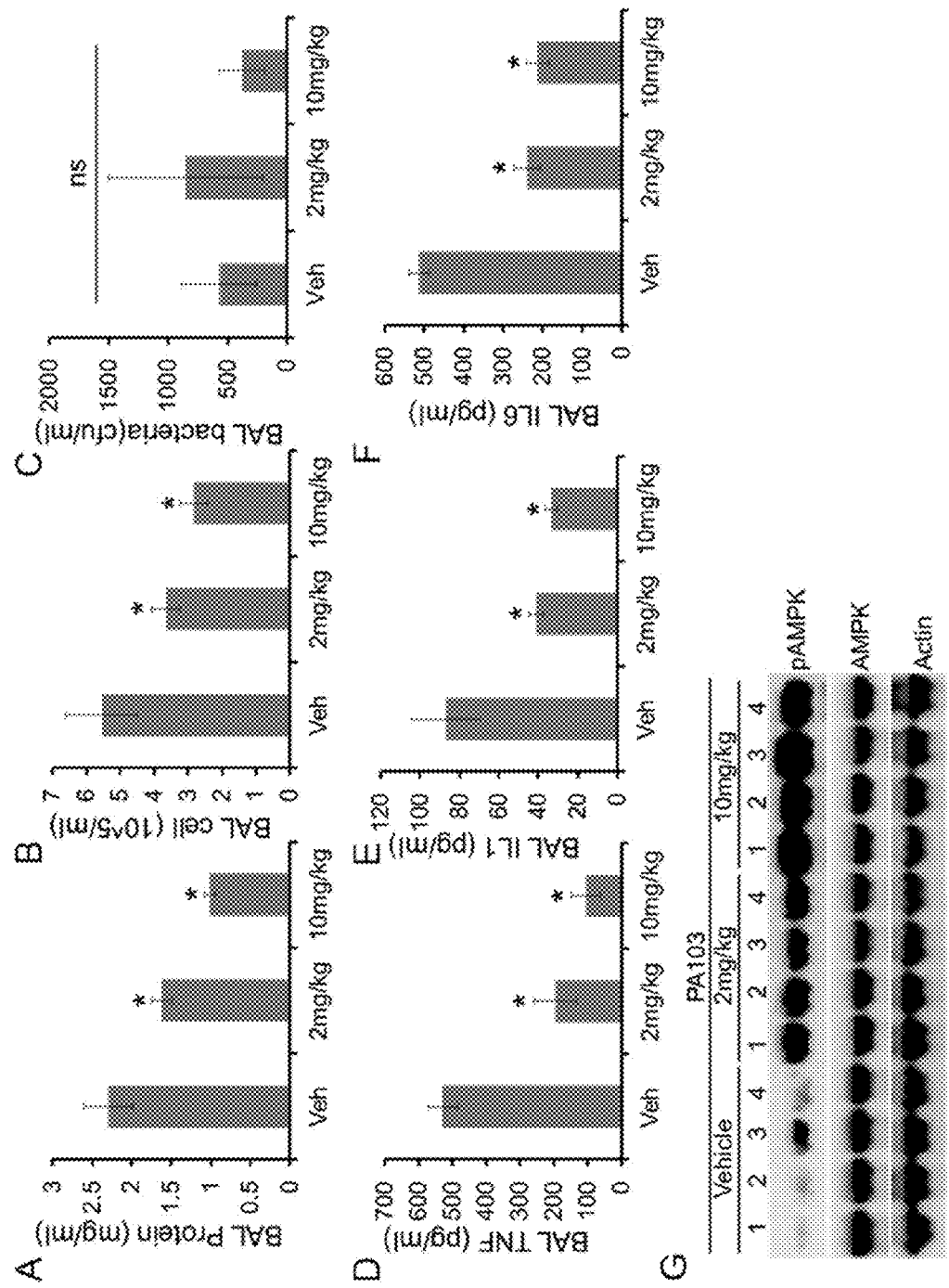
FIG. 5. C57BL6 mice were administered i.p. vehicle, 0.04, 0.2, 1 or 5 mg/kg of Compound 12. After 10 min, mice were given LPS (E. coli, 3 mg/kg) through an i.p. injection and, after 2 h, mice were euthanized and blood was collected for IL1-β, IL-6 and TNFα measurements. Shown in panels (D)-(F) is % inhibition of cytokine levels as a function of drug dose. The data represent n=3 mice/group at each dose. Protein (A), cell counts (B), bacterial count (C), and presence of AMPK and pAMPK (G) were also determined.

In a sepsis model, Compound 12 was administered to mice at various doses through an i.p. injection, and, after 10 min, the mice were given LPS (*E. coli;* 3 mg/kg i.p.). Two hours later, the mice were euthanized, and blood was collected and assayed for IL-1β, IL-6 and TNFα cytokine levels. Compound 12 exhibited high potency in vivo (inhibitory dose [$ID_{50}$] IL-1β=0.1 mg/kg, $ID_{50}$ IL-6=0.4 mg/kg, and $ID_{50}$ TNF-α=0.4 mg/kg) (FIG. 5). These inhibitory concentrations are very low given that the predicted rodent oral $LD_{50}$ doses for Compound 12 are at ~20 g/kg; thus, Compound 12 exerts bioactivity well below a predicted toxic dose in vivo.

Example 6. Compound 12 (BC1609) in CLP-Induced Sepsis Model

Figure 6:
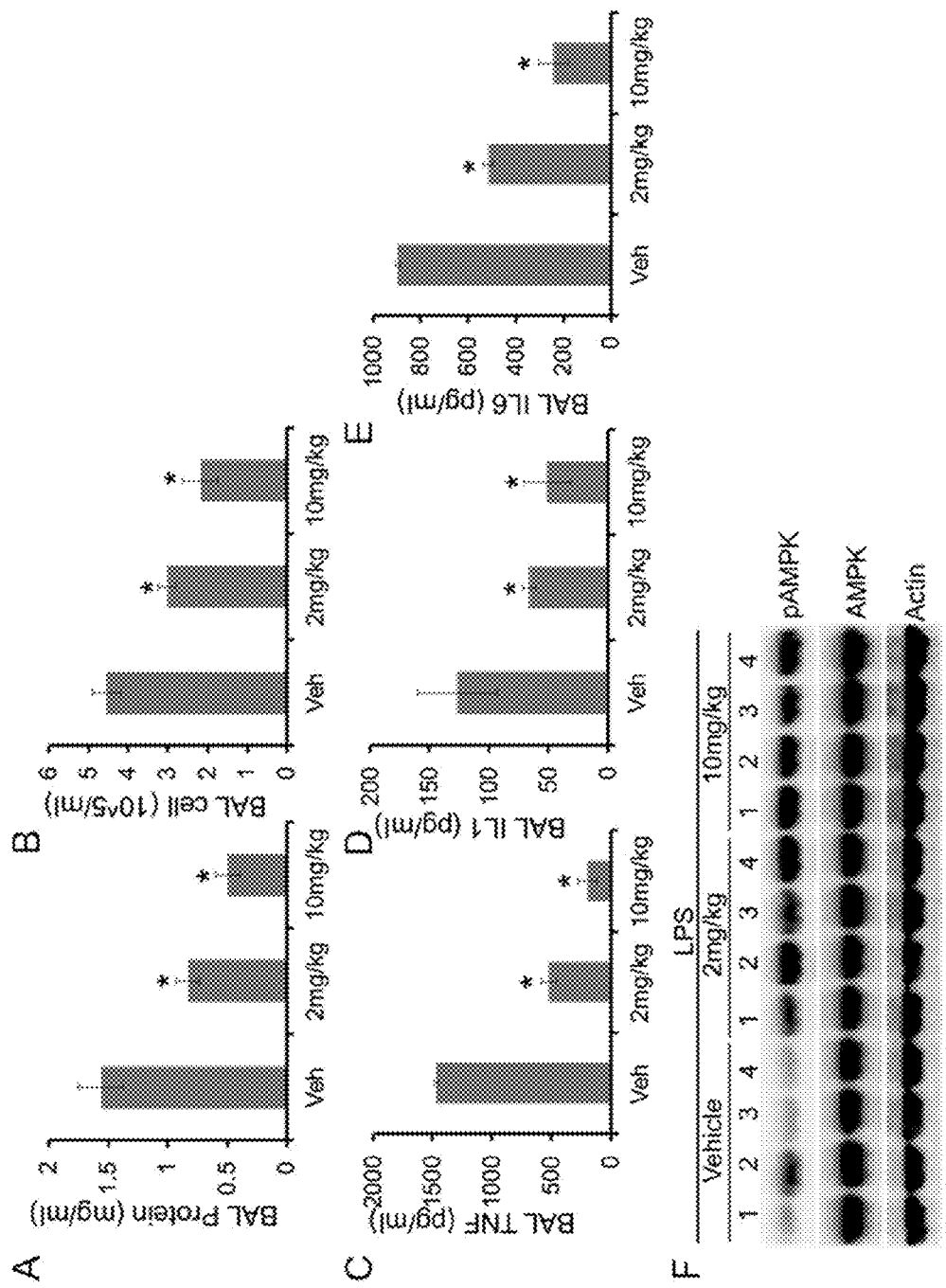
FIG. 6. Mice were anesthetized prior to the cecal ligation and puncture (CLP) procedure. Compound 12 (10 mg/kg) was then administered immediately afterwards through an intraperitoneal (i.p.) injection. After 24 h, mice were euthanized and blood was collected for assays of IL-6, TNF, and IL1-β levels. Peritoneal fluid was obtained for determination of bacterial counts after CLP in mice. The lungs were also lavaged with saline, harvested, and then homogenized. Lavage cytokine secretion (C-E), protein (A), cell counts (B) were measured. The data represent n=4-5 mice/group, *P<0.05 Compound 12 versus vehicle. Presence of AMPK and pAMPK was also determined (F).

Compound 12 was examined in a model of cecal ligation and puncture (CLP)-induced sepsis. Mice with CLP had significantly increased cytokine release. Compound 12 treatment significantly attenuated CLP-induced secretion of all three circulating proinflammatory cytokines in mice (FIGS. 6A-C) without affecting bacterial count in the CLP-induced sepsis model (FIG. 6D). Further, the CLP-induced sepsis model also caused lung injury at 24 h, as indicated by elevated BAL cytokines, protein and cell counts (FIGS. 6E-I). However, Compound 12 was able to effectively reduce severities of CLP-induced lung injury.

Example 7. Compound 12 (BC1609) in Animal Models of Pneumonia

Figure 7:
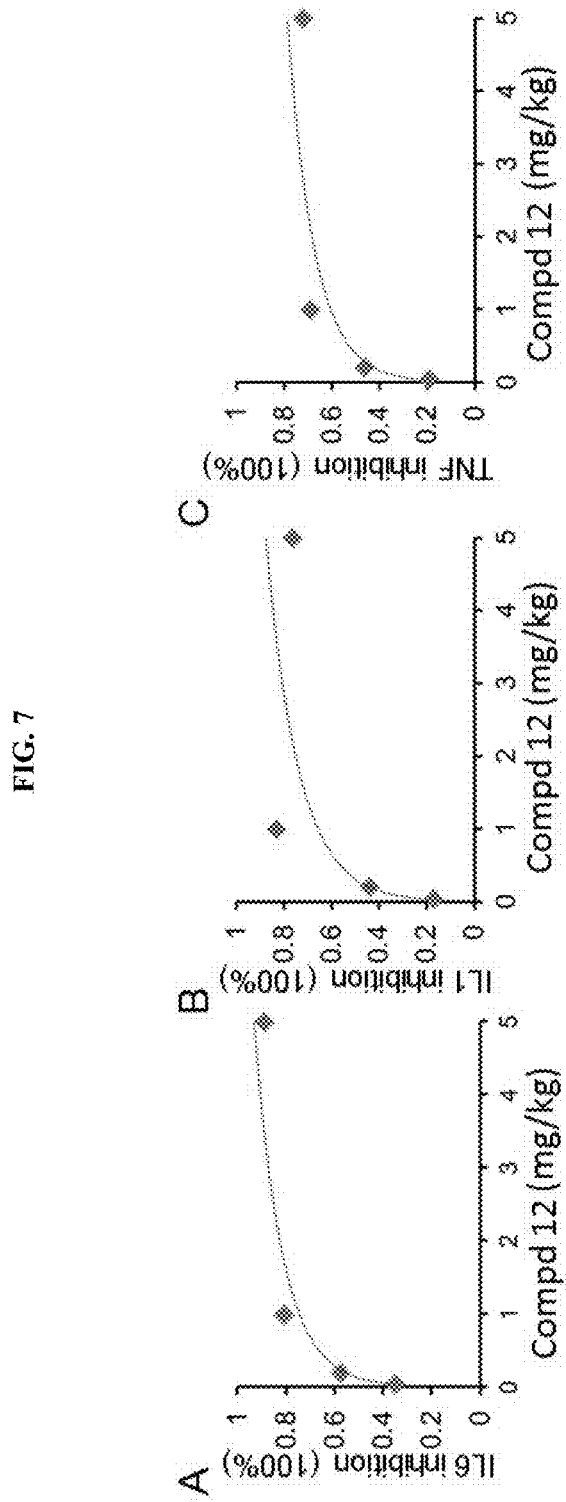
FIG. 7. Compound 12 (2 or 10 mg/kg) was administered to mice though an i.p. injection, and mice were immediately challenged with P. aeruginosa (strain PA103, $1.5*10^4$ cfu/mouse, i.t.) or without (control, CON) for an additional 18 h. Mice were then euthanized and lungs were lavaged with saline, harvested, and then homogenized. Lavage protein, cell counts, bacterial count and cytokine secretions (A-C) were measured. Lungs were homogenized before being assayed by immunoblotting. The data are representative of data from n=5-6 mice/group, *P<0.05 versus vehicle.
Figure 8:
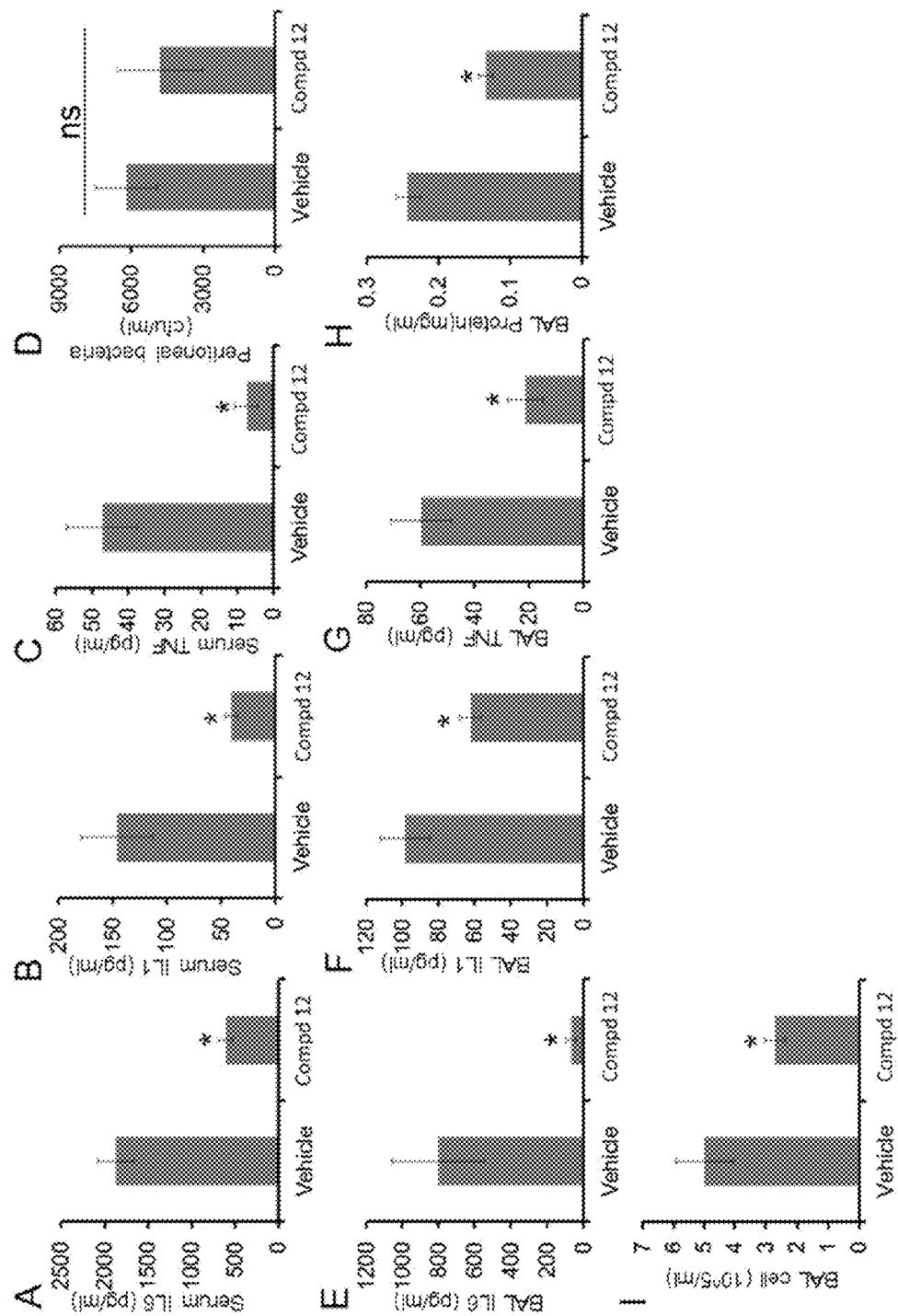
FIG. 8. Compound 12 (2 or 10 mg/kg) was administered to mice though an i.p. injection, and mice were immediately challenged with LPS (*E. coli,* 3 mg/kg, i.t.) or without (control, CON) for an additional 18 h. Mice were then euthanized and lungs were lavaged with saline, harvested, and then homogenized. Lavage protein (H), cell counts (I) and cytokine secretions (E-G) were measured. Lungs were homogenized before being assayed by immunoblotting. The data are representative of data from n=5-6 mice/group, *P<0.05 versus vehicle. Serum cytokines (A-C) and peritoneal bacteria (D) were also measured.

Compound 12 was tested in two pneumonia model using *Pseudomonas* or LPS endotoxin. First, Compound 12 substantially decreased lavage protein concentration, lavage cell counts without affecting lavage bacterial counts after PA103 infection (FIGS. 7A-C). Compound 12 also effectively reduces lavage proinflammatory cytokines in dose dependent manner (FIGS. 7D-F). These beneficial effects of the agent were associated with drastically increasing in pAMPK levels within the lung tissue (FIG. 7G). Similar effects of Compound 12 were observed in an LPS pneumonia model whereby Compound 12 significantly decreased lavage protein concentration, cell counts and cytokine release (FIGS. 8A-E). Compound 12 also effectively increased pAMPK levels within the lung tissue in this model (FIG. 8F).

Example 8. In Vitro Characterization of Compound 23 (BC1618)

Figure 9:
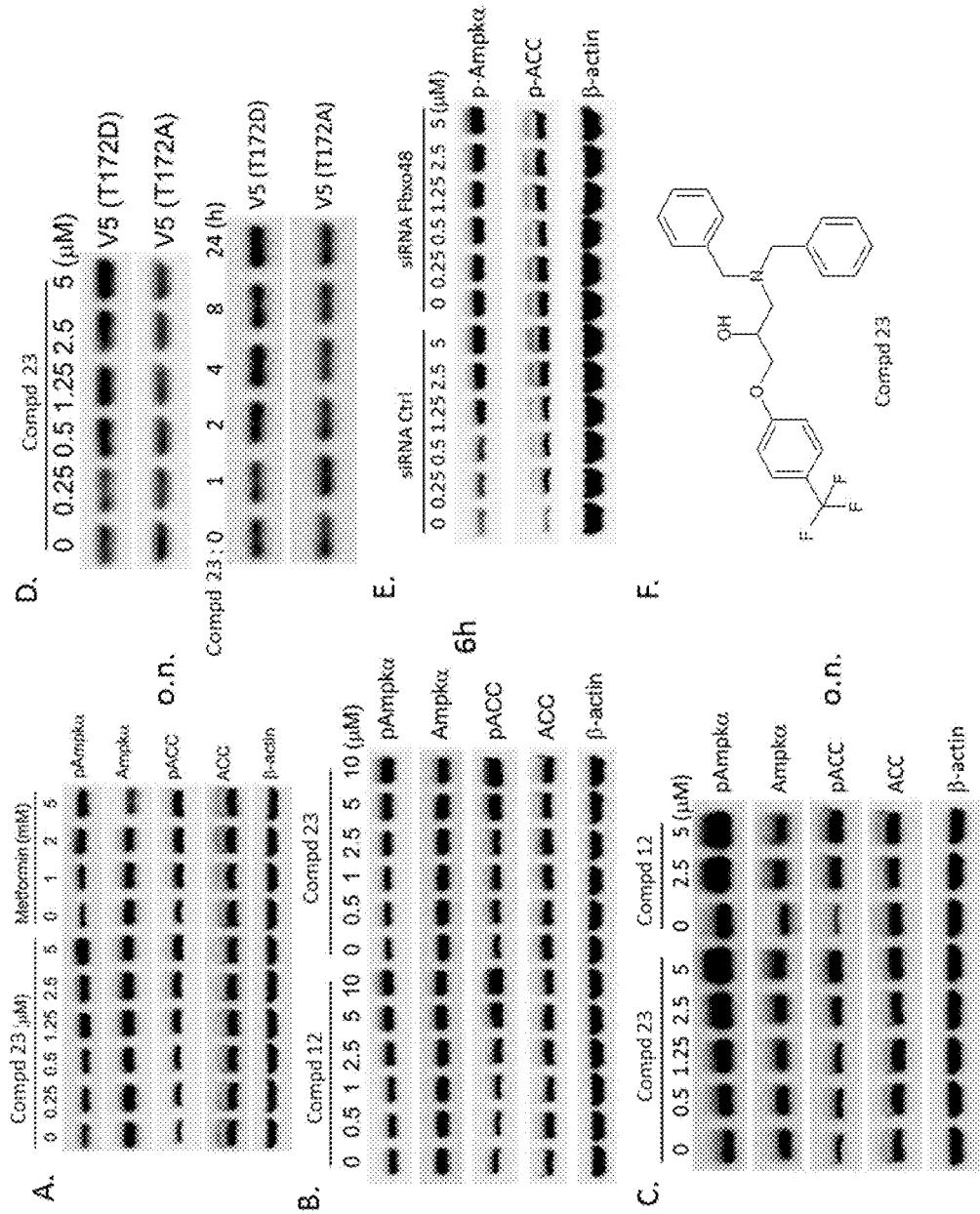
FIG. 9. (A) Beas2b cells were cultured in DMEM 2% media with glucose for 24 h before switching to glucose-free media. Cells were then exposed to Compound 23 or metformin in a dose dependent manner for 18 h before being collected for immunoblotting. (B) Beas2b cells were cultured in DMEM 2% media with glucose for 24 h before switching to glucose-free media and treated with Compound 12 or Compound 23 in a dose dependent manner. After 6 h, cells were then collected for immunoblotting. (C) Beas2b cells were cultured in DMEM 2% media with glucose for 24 h before switching to glucose-free media and treated with Compound 12 or Compound 23 in a dose dependent manner. After 18 h, cells were then collected for immunoblotting. (D) Beas2b cells were transfected with AMPK phospho mimic T172D or phospho dead T172A mutant for 24 h. Cells were then switched to glucose-free media and exposed to Compound 23 in a dose or time dependent manner before being collected for immunoblotting. (E) Beas2b cells were transfected with control siRNA or Fbxo48 siRNA for 48 h before switching to glucose-free media. Cells were then exposed to Compound 23 in a dose dependent manner before being collected for immunoblotting. (F) Compound 23 chemical structure.

Compound 23 was tested in in vitro studies using Beas2B cells and compared with metformin. Compound 23 drastically increases pAMPK phosphorylation and downstream substrate ACC phosphorylation at submicromolar concentration, whereas metformin achieves similar results with millimolar concentration (FIG. 9A). Similarly, Compound 23 also showed comparable or slightly improved activity compared to Compound 12 (FIGS. 9B and 9C). As a control experiment, Compound 23 was assessed for its ability to increase levels of AMPK phospho mimic T172D mutant and phospho dead mutant T172A. As shown in FIG. 9D, Compound 23 drastically increases T172D phospho mimic mutant, suggesting that Compound 23 blocks the pAMPK degradation. It was further confirmed that Compound 23 indeed targets Fbxo48/pAMPK pathway. siRNA was used to knockdown Fbxo48 and such cells were treated with Compound 23. As shown in FIG. 9E, Fbxo48 knockdown is sufficient to increase pAMPK and pACC levels; and Compound 23 is not able to further activate the pathway.

Figure 10:
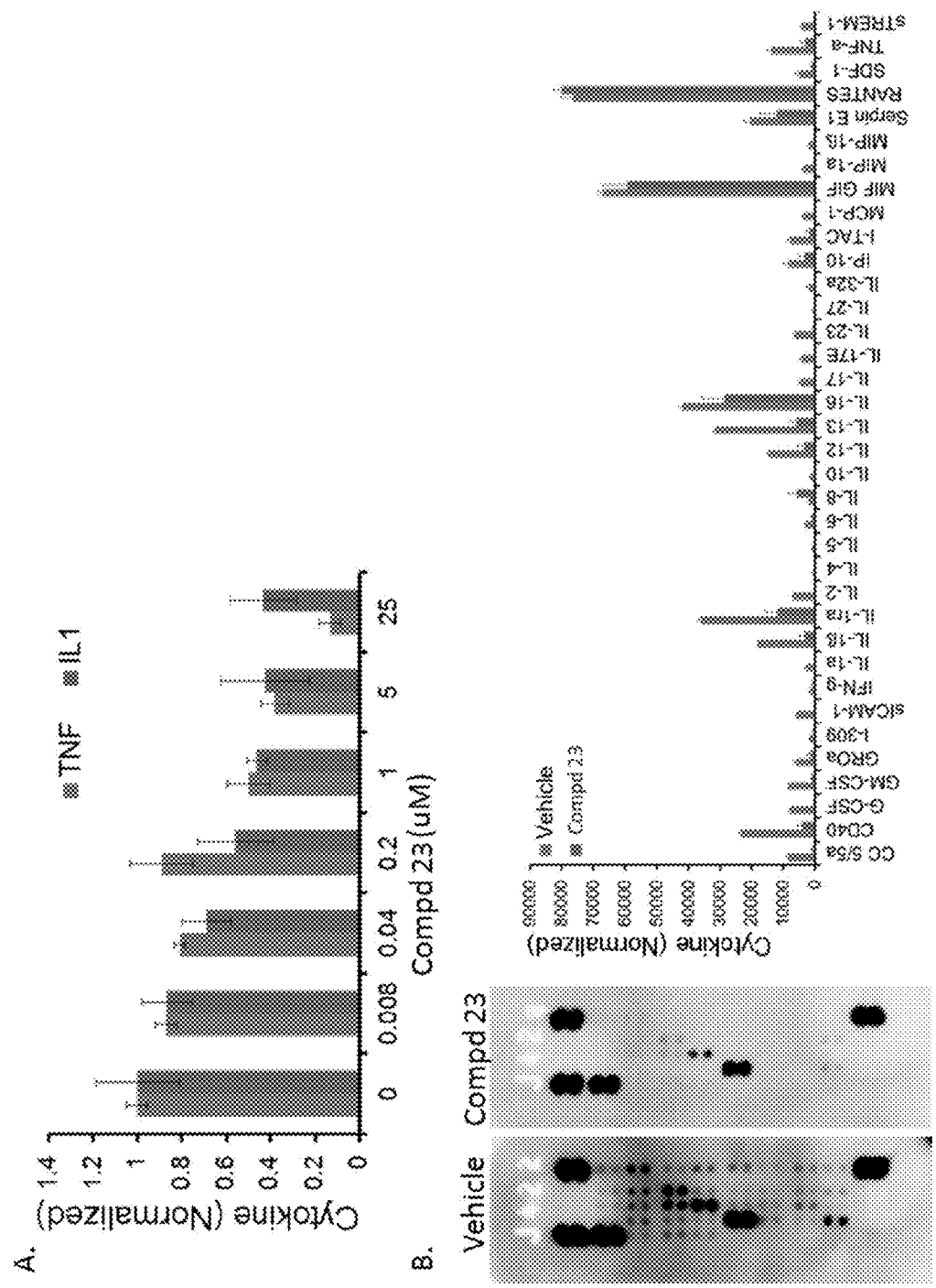
FIG. 10. (A) 50K PBMC cells were cultured in 96 well plates before being exposed to Compound 23 for 18 h. Cells were then treated with LPS (10 ng/ml) for additional 4 h. Media were then collected and TNF and IL-1b concentration were determined by ELISA. (B) PBMC cells (1 mL at $1.0 \times 10^6$/ml) were treated with Compound 23 (5 μM) for 18 h. Cells were then treated with 100 ng/ml LPS for 4 h. Cytokine release was monitored by the human cytokine array (R&D systems). The results from a cytokine array dot blot were quantitated and graphed.

Compound 23 was tested in in vitro inflammatory assays. 50K PBMC cells were cultured in 96 well plates before being exposed to Compound 23 for 18 h. Cells were then treated with LPS (10 ng/ml) for additional 4 h. Media were then collected and assayed for TNF and IL-1b. Compound 23 dose dependently decreased both TNF and IL-1b cytokines (FIG. 10A). Cytokine arrays were used to profile which cyotokine/chemokines were regulated by Compound 23. As shown in FIG. 10B, Compound 23 decreases CD40, GMCSF, IL-1b, IL-1ra, IL-2, IL-12, IL-13, ITAC and TNF.

Example 9. In Vivo Characterization of Compound 23 (BC1618)

Figure 11:
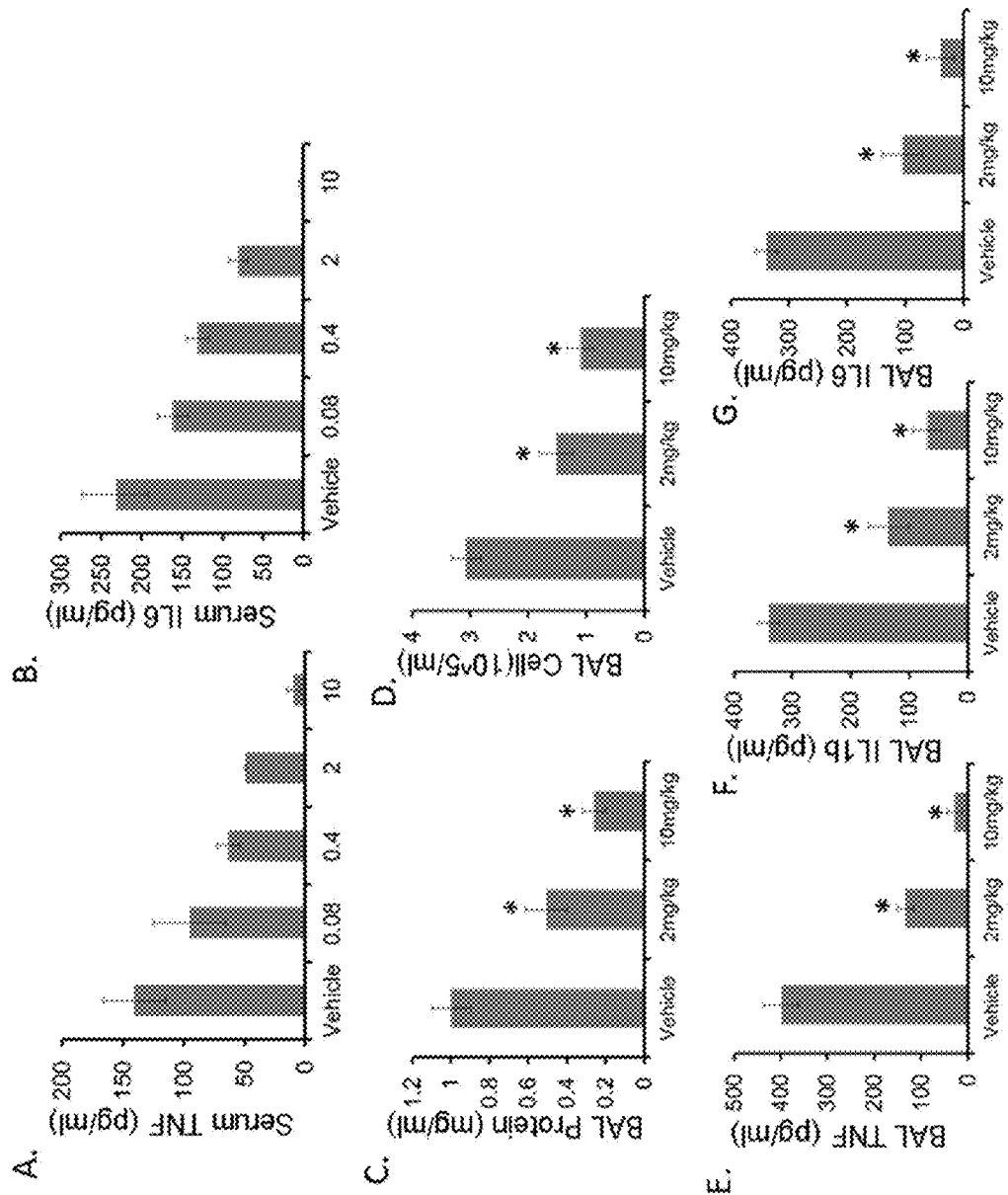
FIG. 11. (A-B.) C57BL6 mice were administered i.p. vehicle, 0.08, 0.4, 2 or 10 mg/kg of Compound 23. After 10 min, mice were given LPS (*E. coli,* 3 mg/kg) through an i.p. injection and, after 2 h, mice were euthanized and blood collected for IL-6 and TNFα measurements. Shown in panels (A-B.) are the cytokine levels as a function of drug dose. The data represent n=3 mice/group at each dose. (C-G) Compound 23 (2 or 10 mg/kg) was administered to mice though an i.p. injection, and mice were immediately challenged with LPS (*E. coli,* 3 mg/kg, i.t.) or without (control, CON) for an additional 18 h. Mice were then euthanized and lungs were lavaged with saline, harvested, and then homogenized. Lavage protein (C), cell counts (D) and cytokine secretions (E-G) were measured. The data are representative of data from n=5 mice/group, *P<0.05 versus vehicle.

Compound 23 was tested in a sepsis model. Compound 23 was administered to mice at various doses through an i.p. injection, and 10 min later, mice were given LPS (*E. coli;* 3 mg/kg i.p.). After 2 h, mice were euthanized and blood was collected and assayed for IL-6 and TNFα cytokine levels. Compound 23 exhibited high potency in vivo (inhibitory dose $ID_{50}$ IL-6=0.4 mg/kg, and $ID_{50}$ TNF-α=0.4 mg/kg) (FIGS. 11A and 11B). Finally, Compound 23 was tested in a pneumonia model using LPS endotoxin. First, Compound 23 substantially decreased lavage protein concentration and lavage cell counts (FIGS. 11C-D). Compound 23 also effectively reduces lavage proinflammatory cytokines in dose dependent manner (FIGS. 11E-G). Thus Compound 23 protects the lung against LPS induced lung injury.

Example 10. Preparation of Compound 11 (BC1601)

Aminodiphenylmethane (5 mmol) and 2-[(4-fluorophenoxy)methyl]oxirane (5 mmol) were combined ant stirred under $N_2$ at 70° C. overnight. The reaction mixture was cooled down to produce a yellow oil, which was then purified using column chromatography to obtain the final product as yellow crystals (1.2 g, 68% yield).

Example 11. Preparation of Compound 12 (BC1609)

Dibenzylamine (5 mmol) and 2-[(4-fluorophenoxy)methyl]oxirane (5 mmol) were combined and stirred under $N_2$ at 70° C. overnight. The reaction mixture was cooled down to produce a brown oil, which was then purified using column chromatography to obtain the final product as a yellow oil (1.4 g, 77% yield).

Example 12. Preparation of Compound 13 (BC15160)

Aminodiphenylmethane (5 mmol) and 2-(phenoxymethyl)oxirane (5 mmol) were combined and stirred under $N_2$ at 70° C. overnight. The reaction mixture was cooled down, and white crystals were formed. The product was then recrystallized in ethyl acetate (15 mL) to obtain the desired product as white powder (1.0 g, 58% yield).

Example 13. Preparation of Compound 14 (BC15161)

2,2-Diphenylethylamine (5 mmol) and 2-(phenoxymethyl)oxirane (5 mmol) were combined and stirred under $N_2$ at 70° C. overnight. The reaction mixture was cooled down to produce a yellow oil. The product was then purified using column chromatograph to obtain the final product yellow powder (0.8 g, 50% yield).

Example 14. Preparation of Compound 15 (BC1602)

9H-Xanthen-9-amine (4 mmol) and 2-(phenoxymethyl)oxirane (4 mmol) were dissolved in DMF (2 mL) and stirred under $N_2$ at 100° C. for 3 h. The reaction mixture was cooled down to produce a yellow oil. Brine (30 mL) was then added to the reaction mixture under stirring for 15 min to liberate the product. Product was then filtered, washed with water and dried under vacuum overnight to obtain product as yellow powder (1.29 g, 84% yield).

Example 15. Preparation of Compound 16 (BC1603)

Dibenzylamine (5 mmol) and 2-(phenoxymethyl)oxirane (5 mmol) were dissolved in isopropanol (20 mL) and heated to reflux for 4 h. Solvent was then removed under vacuum to obtain the final product as a yellow oil (1.6 g, 90% yield).

Example 16. Preparation of Compound 17 (BC1604)

2,2-Diphenylethylamine (5 mmol) and 2-[(4-methoxyphenoxy)methyl]-oxirane (5 mmol) were dissolved in isopropanol (20 mL) and heated to reflux overnight Solvent was then removed under vacuum to obtain the final product as yellow crystals (1.7 g, 90% yield).

Example 17. Preparation of Compound 18 (BC1606)

Epichlorohydrin (0.01 mol) and 4-cyclohexyl-phenol (0.01 mol) were added to water (30 mL) containing 30 mmol NaOH. The reaction mixture was refluxed for 1 h and cooled down. White precipitate was filtered, washed with water and dried under vacuum. The product was then recrystallized in ethanol to obtain 2-[(4-cyclohexylphenoxy)methyl]-oxirane (white crystals, 2.7 g, 100% yield). 2-[(4-Cyclohexylphenoxy)methyl]-Oxirane (4 mmol) and aminodiphenylmethane (4 mmol) were dissolved in ethanol and heated to reflux overnight under $N_2$. Solvent was then removed under vacuum to obtain the final product as yellow crystals (1.4 g, 0.84% yield).

Example 18. Preparation of Compound 19 (BC1607)

Epichlorohydrin (0.02 mmol) and dibenzylamine (0.02 mmol) were combined and stirred under $N_2$ at 90° C. overnight. The reaction mixture was cooled down to obtained the 1-[bis(phenylmethyl)amino]-3-chloro-2-propanol (yellow oil, 100% yield). 1-[Bis(phenylmethyl)amino]-3-chloro-2-propanol (3 mmol) and 4-cyclohexyl-Phenol (3 mmol) were added to water (20 mL) containing 10 mmol NaOH. The reaction mixture was heated to reflux for 1 h and cooled down. Ethyl acetate (2×20 mL) was used to extract the product. Solvent was then removed under vacuum to obtain the final product as yellow crystals (0.9 g, 0.66% yield).

Example 19. Preparation of Compound 20 (BC1608)

Epichlorohydrin (0.01 mol) and 4-cyclohexyl-phenol (0.01 mol) were added to water (30 mL) containing 30 mmol NaOH. The reaction mixture was heated to reflux for 1 h and cooled down. White precipitate was filtered, washed with water and dried under vacuum. The product was then recrystallized in ethanol to obtain 2-[(4-cyclohexylphenoxy)methyl]-oxirane (white crystals, 2.7 g, 100% yield). 2-[(4-Cyclohexylphenoxy)methyl]-oxirane (4 mmol) and 2,2-diphenylethylamine (4 mmol) were dissolved in ethanol and refluxed overnight under $N_2$. Solvent was then removed under vacuum to obtain the final product as yellow crystals (1.5 g, 0.87% yield).

Example 20. Preparation of Compound 21 (BC1610)

Epichlorohydrin (0.02 mmol) and dibenzylamine (0.02 mmol) were combined and stirred under $N_2$ at 90° C. overnight. The reaction mixture was cooled down to obtain 1-[bis(phenylmethyl)amino]-3-chloro-2-propanol (yellow oil, 100% yield). 1-[Bis(phenylmethyl)amino]-3-chloro-2-propanol (3 mmol) and (4-hydroxyphenyl)phenyl-methanone (3 mmol) were added to water (20 mL) containing 9 mmol NaOH. The reaction mixture was heated to reflux for 1 h and cooled down. Ethyl acetate (2×20 mL) was used to extract the product Solvent was then removed under vacuum to obtain the final product as a yellow oil (0.83 g, 58% yield).

Example 21. Preparation of Compound 22 (BC1611)

Epichlorohydrin (0.02 mmol) and dibenzylamine (0.02 mmol) were combined and stirred under $N_2$ at 90° C. overnight. The reaction mixture was cooled down to obtain 1-[bis(phenylmethyl)amino]-3-chloro-2-propanol (yellow oil, 100% yield). 1-[Bis(phenylmethyl)amino]-3-chloro-2-propanol (3 mmol) and 4-(2-pyridinyl)-phenol (3 mmol) were added to water (20 mL) containing 9 mmol NaOH. The reaction mixture was heated to reflux for 1 h and cooled down. Ethyl acetate (2×20 mL) was used to extract the product. Solvent was then removed under vacuum to obtain the final product as a yellow oil (0.75 g, 54% yield).

Example 22. Preparation of Compound 23 (BC1618)

Dibenzylamine (5 mmol) and 2-{[4-(trifluoromethyl)phenoxy]methyl}oxirane (5 mmol) were combined and stirred under $N_2$ at 70° C. for 24 h. The reaction mixture was cooled down to produce white crystals, which were then purified using column chromatography to obtain the final product as white powder (2.03 g, 86% yield).

Additional compounds in Table 1 were or can be prepared according to the above-described Examples. Data in Table 1 was obtained by the following method. Human bronchial epithelial cells (Beas2B) were seeded in 6-well plates for 18 h. Cells were then exposed to DMEM media without glucose and compounds at various concentrations for an additional 18 h before being collected for immunoblotting.

Example 23. Diet-Induced Obese Mice Study

Figure 12:
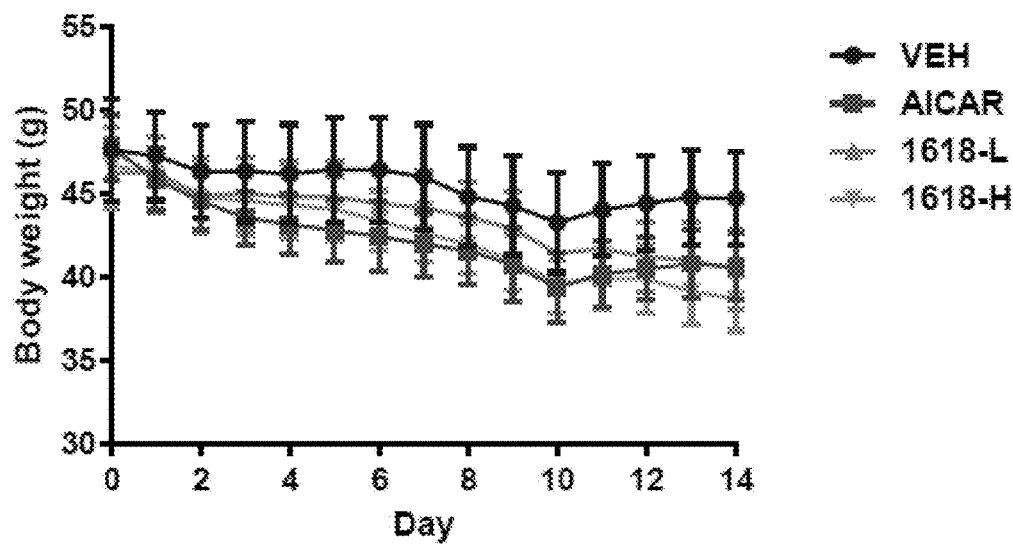
FIG. 12. Diet-induced obese mice were fed a high-fat diet for 19 weeks and then injected with vehicle or drug once daily for 14 days. Daily body weights (in grams) of the mice are shown.
Figure 13:
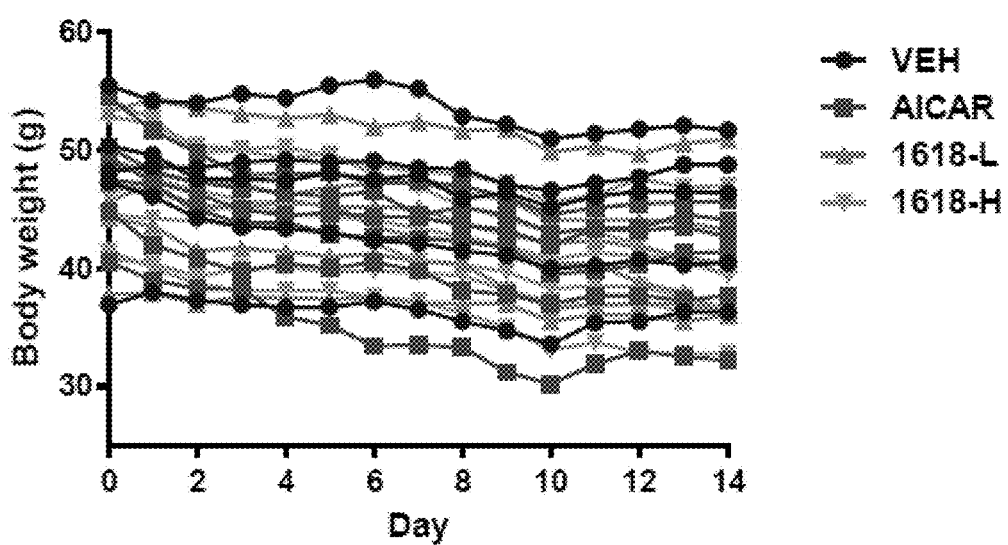
FIG. 13. Individual points for the data in FIG. 12 are shown.
Figure 14:
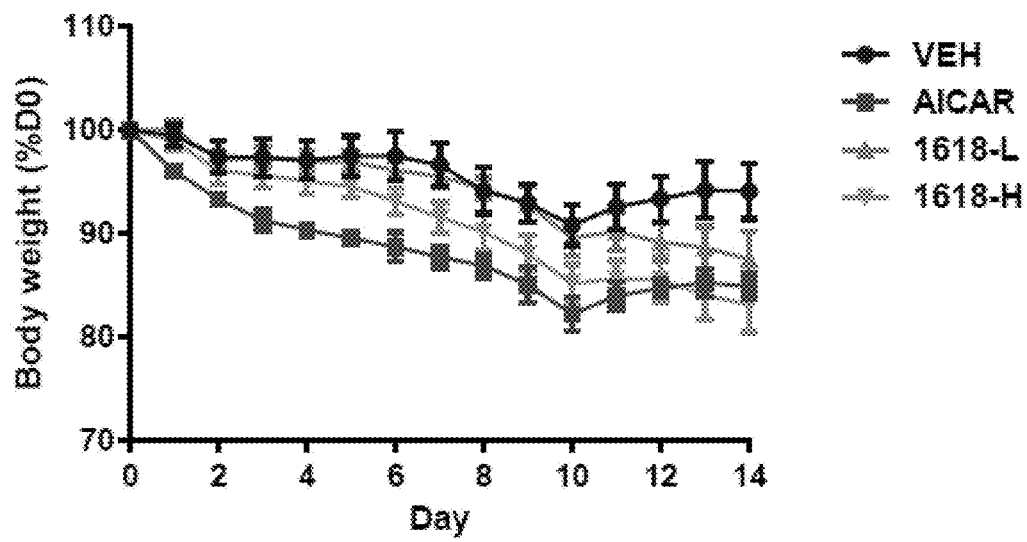
FIG. 14. From the same study as in FIG. 12, daily body weights are shown as a percentage of body weight on day 0.
Figure 15:
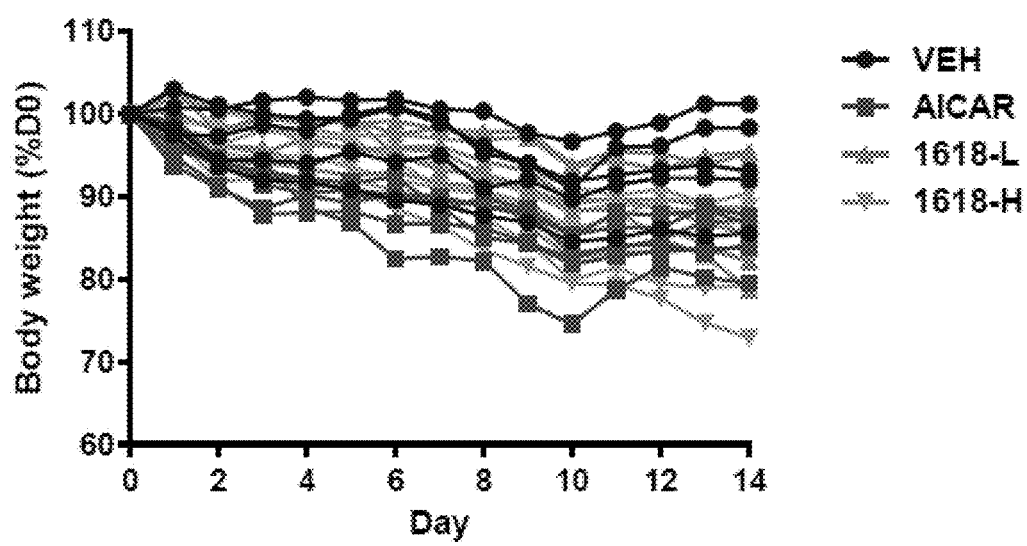
FIG. 15. Individual points for the data in FIG. 14 are shown.
Figure 16:
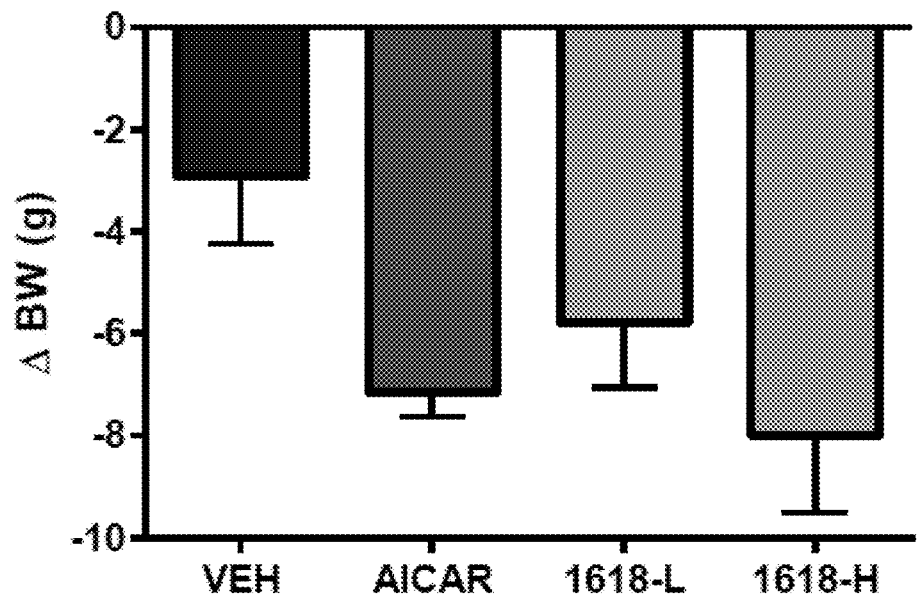
FIG. 16. From the same study as in FIG. 12, change in body weight (BW) from day 0 to day 14 are shown, expressed as change in grams.
Figure 17:
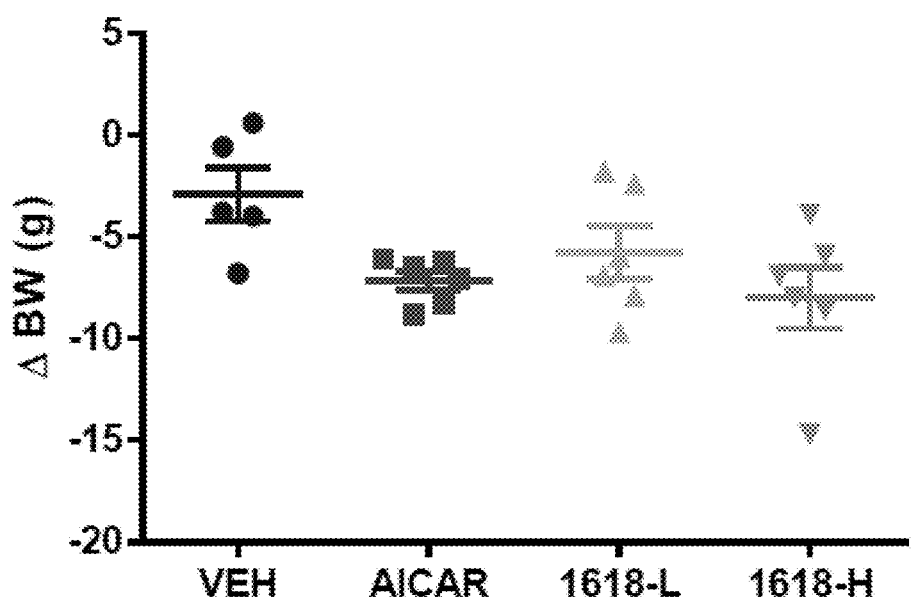
FIG. 17. Individual points for the data in FIG. 16 are shown.

Diet-induced obese mice arrived from Jackson Labs and recovered two weeks in satellite housing before study. Mice were 25 weeks old and fed a high-fat diet for 19 weeks at the time of study. Body weight, fat and lean mass were measured and mice were grouped in order to match body weights at ~46.5 g average per group prior to study. Following the acute dosing trial, mice were injected with vehicle or drug 1× daily between noon and 2 pm for 14 days (BC1618-L (low dose)=8 mg/kg/d, BC1618-H (high dose)=40 mg/kg/d). Body weight was recorded daily (FIGS. 12-15). FIG. 12 and FIG. 13 show body weight in grams and FIG. 14 and FIG. 15 show body weight as a percentage of body weight on day 0 (DO). All groups lost weight, but there appears to be both an effect of AICAR and BC1618 on body weight loss.

Figure 18:
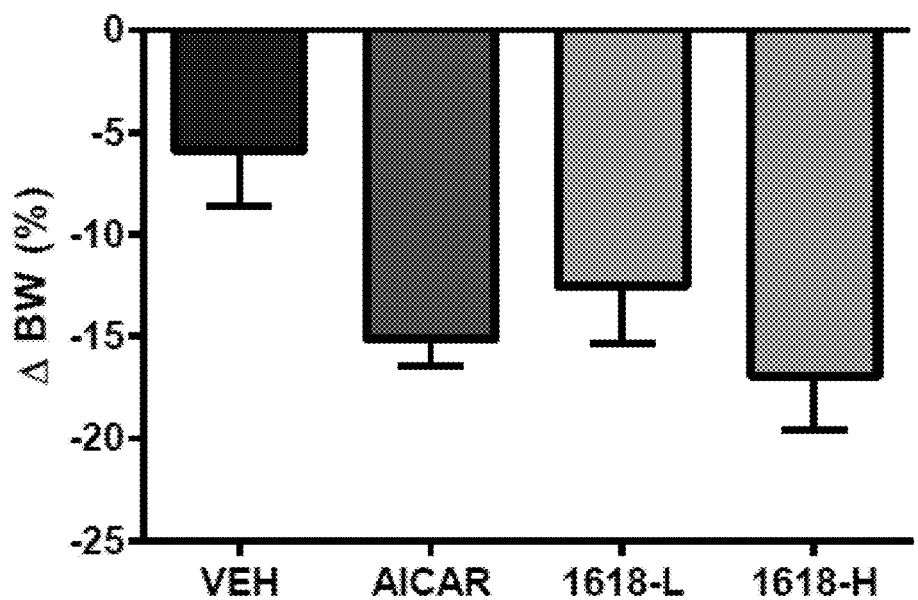
FIG. 18. From the same study as in FIG. 12, change in body weight (BW) from day 0 to day 14 are shown, expressed as percent change from day 0.
Figure 19:
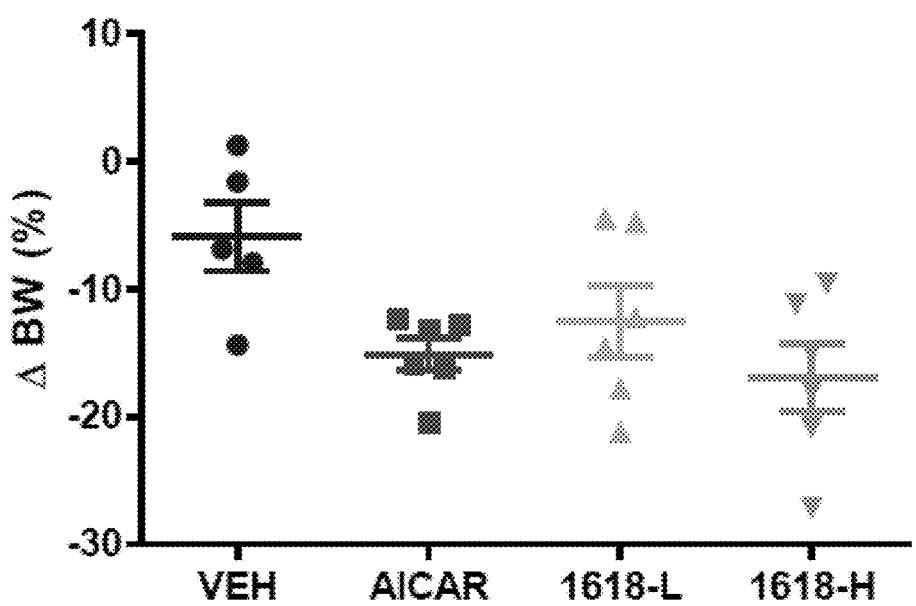
FIG. 19. Individual points for the data in FIG. 18 are shown.
Figure 20:
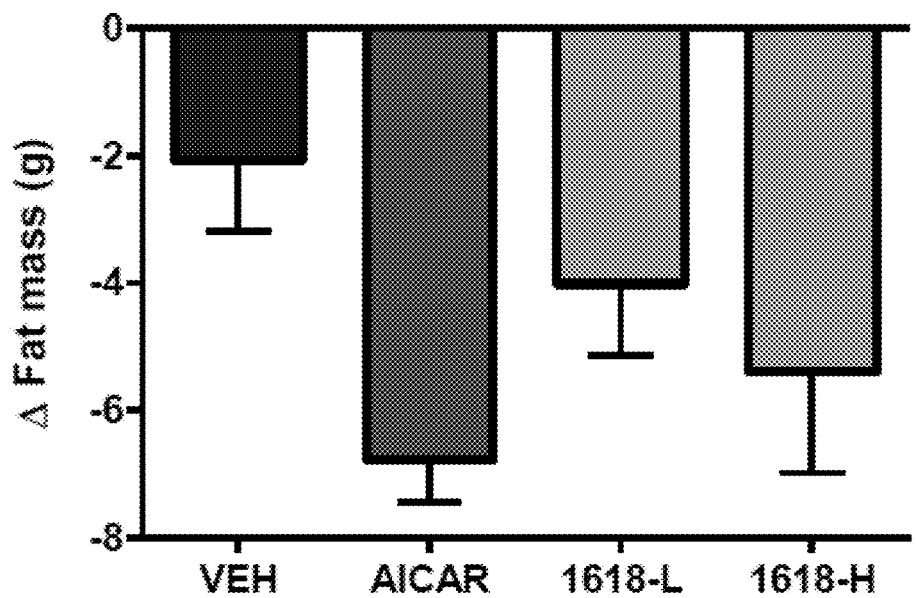
FIG. 20. From the same study as in FIG. 12, change in fat mass from day 0 to day 14 is shown, expressed in grams.
Figure 21:
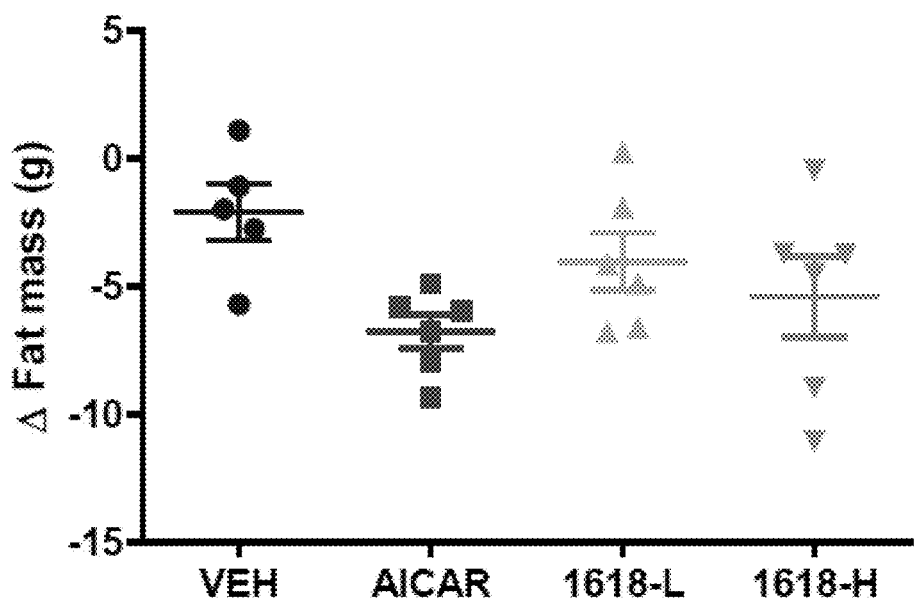
FIG. 21. Individual points for the data in FIG. 20 are shown.

FIGS. 16-19 show the change (Δ) in body weight (BW) from day 0 to day 14 expressed as change in grams (FIG. 16 and FIG. 17) or as percent change from day 0 (FIG. 18 and FIG. 19). Again, there appears to be an effect due to AICAR or BC1618.

Figure 22:
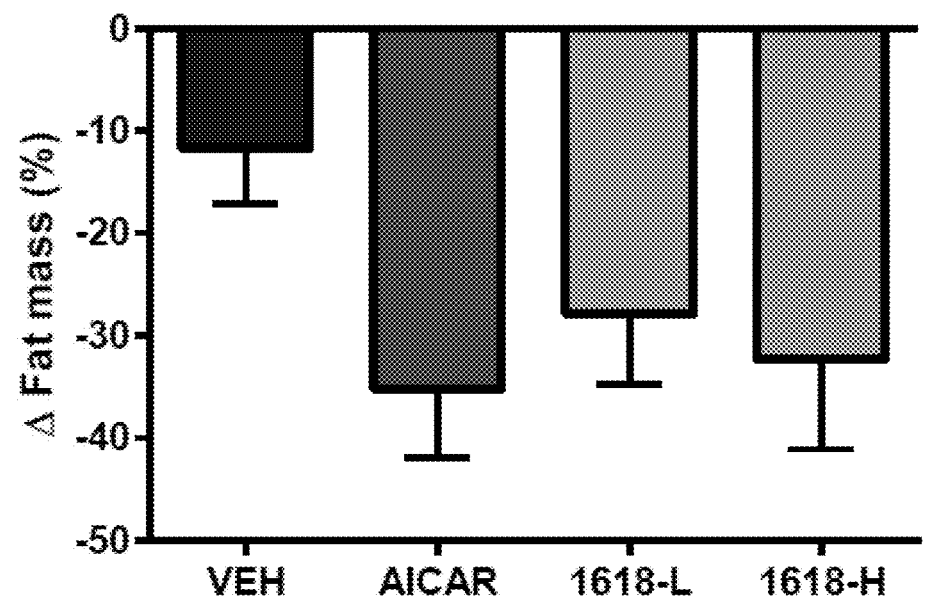
FIG. 22. From the same study as in FIG. 12, change in fat mass from day 0 to day 14 is shown, expressed as percent change.
Figure 23:
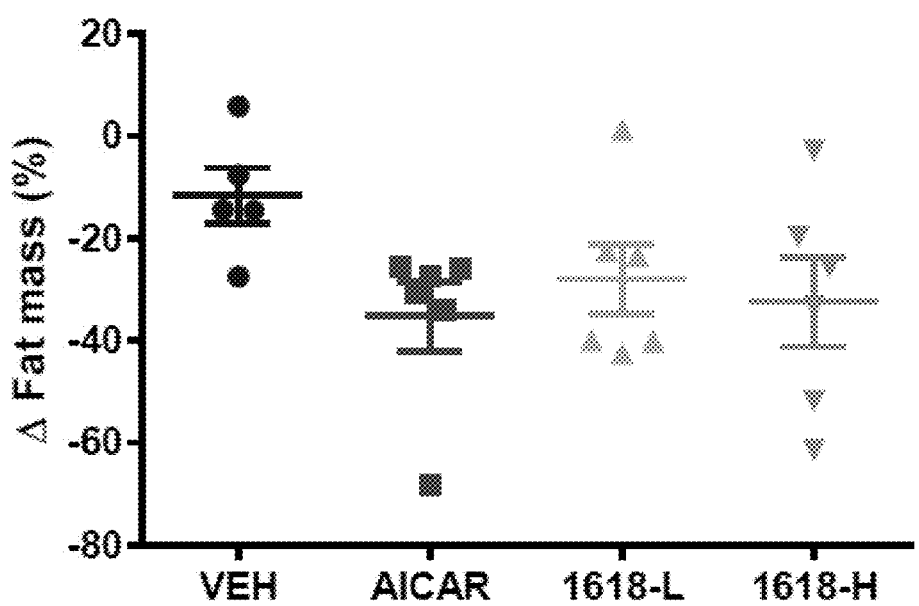
FIG. 23. Individual points for the data in FIG. 22 are shown.
Figure 24:
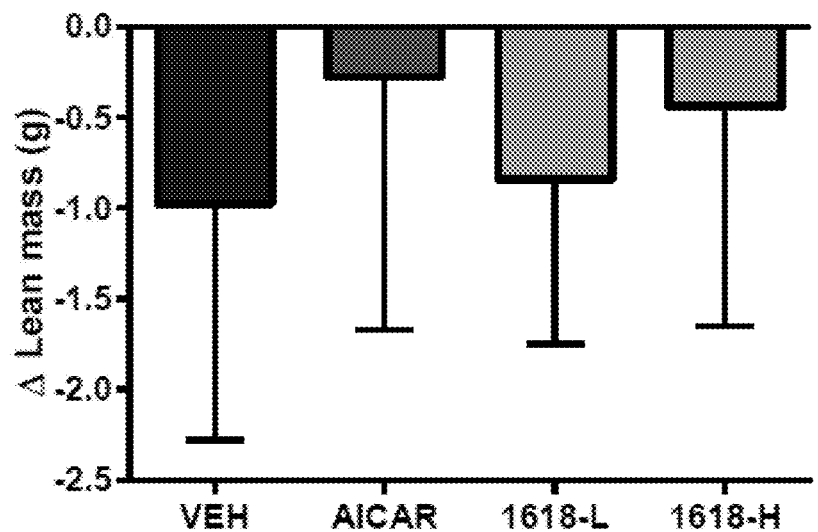
FIG. 24. From the same study as in FIG. 12, change in lean mass from day 0 to day 14 is shown, expressed in grams.
Figure 25:
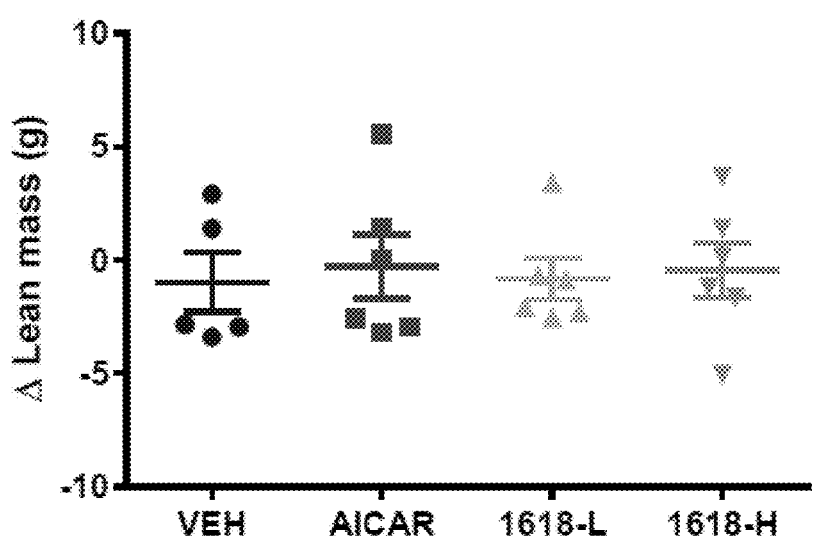
FIG. 25. Individual points for the data in FIG. 24 are shown.

Body composition was measured at DO in the body weight matched animals and again at day 14 (D14). Data in FIGS. 20-23 represent the change in fat mass from DO to D14 expressed as grams (FIG. 20 and FIG. 21) or as percent change (FIG. 22 and FIG. 23). Data largely mirror the effects observed for body weight where there is an effect of vehicle alone and an apparent additive effect of AICAR and BC1618.

Figure 26:
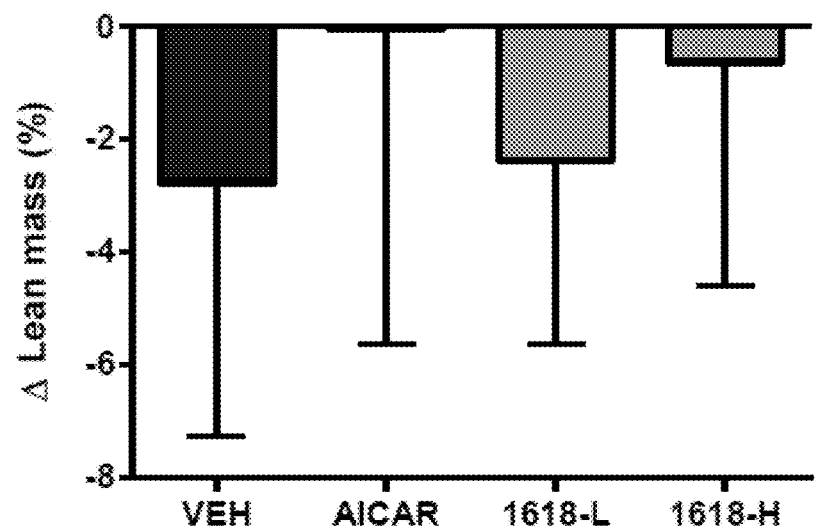
FIG. 26. From the same study as in FIG. 12, change in lean mass from day 0 to day 14 is shown, expressed as percent change.
Figure 27:
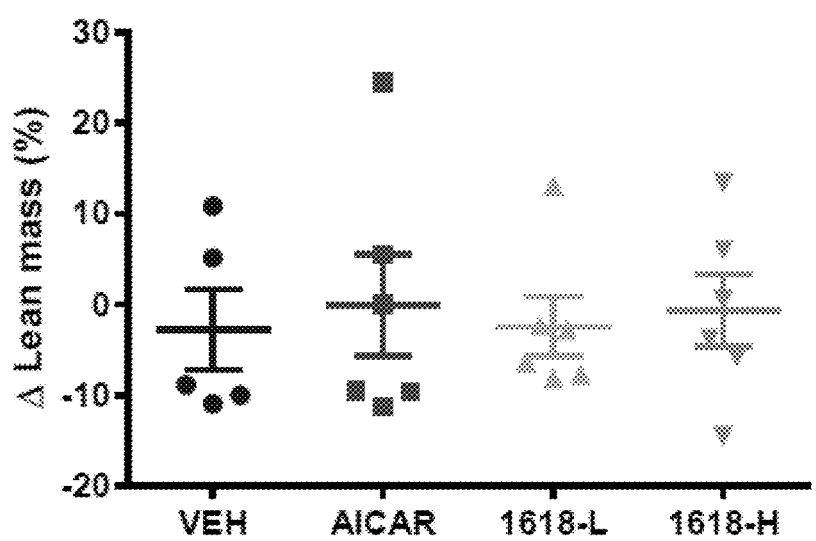
FIG. 27. Individual points for the data in FIG. 26 are shown.

Data in FIGS. 24-27 represent the change in lean mass from DO to D14 expressed as grams (FIG. 24 and FIG. 25) and as percent change (FIG. 26 and FIG. 27). Overall there appears to be a modest effect of vehicle and drug to reduce lean mass over 14 days, but no differences between groups. Changes in BW over 14 days therefore reflect changes in fat mass and not lean mass.

Example 24. Acute Oral Dosing Studies in Mice

Figure 28:
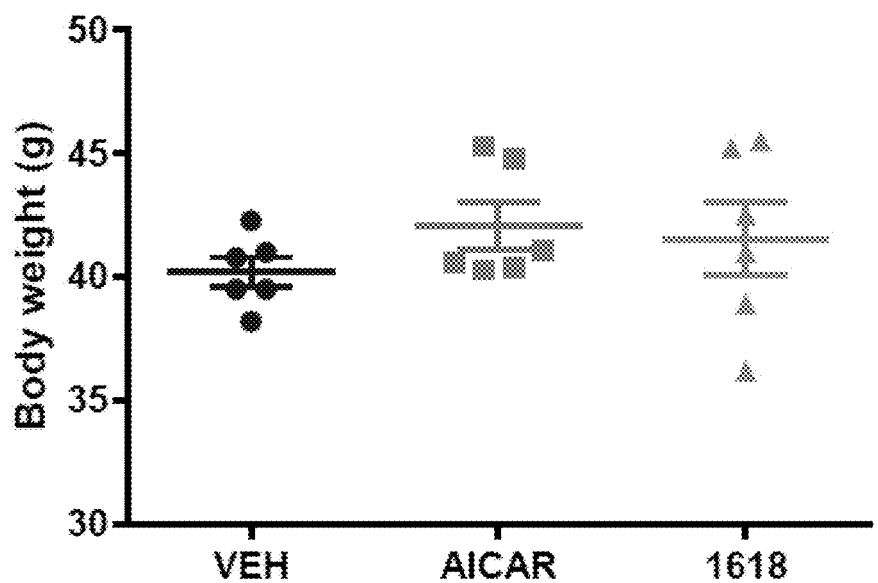
FIG. 28. High-fat diet fed (20 weeks) C57BL6J mice were fasted overnight beginning at 4 pm. Mice were given one oral dose of vehicle or drug (AICAR at 200 mg/kg, BC1618 at 20 mg/kg) at 5 pm and an additional dose the following morning at 7 am. Body weight measurements are shown.
Figure 29:
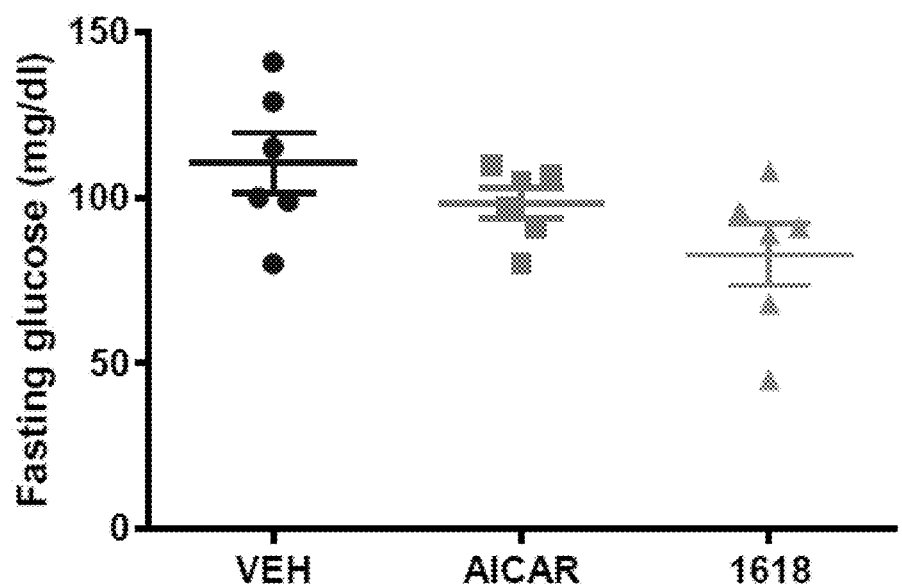
FIG. 29. From the same study as in FIG. 28, fasting plasma glucose was measured 2 h after the additional dose. Fasting plasma glucose measurements are shown.

High-fat diet fed (20 weeks) $C_{57}BL6J$ mice were fasted overnight beginning at 4 pm. Mice were given one oral dose of vehicle or drug (AICAR at 200 mg/kg, BC1618 at 20 mg/kg) at 5 pm and an additional dose the following morning at 7 am. Fasting plasma glucose was measured 2 h later at 9 am, followed by an intraperitoneal glucose tolerance test (1 g/kg body weight glucose). There were no differences in body weight at the time of study (FIG. 28). Fasting plasma glucose was reduced 10% and 25% in the AICAR and BC1618 treated groups, respectively, compared to vehicle (P=0.08, one-way ANOVA; FIG. 29). There was no difference in glucose tolerance between groups (data not shown).

Example 25. Hyperinsulinemic Euglycemic Clamp Studies

Figure 30:
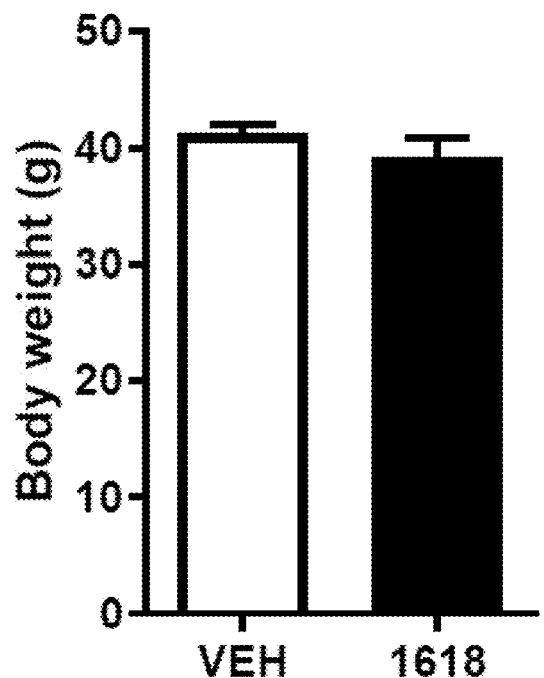
FIG. 30. Diet-induced obese mice were dosed 1× with vehicle or BC1618 (20 mg/kg) prior to overnight fast, followed by a 1× (20 mg/kg) morning dose prior to hyperinsulinemic euglycemic clamp. Body weight measurements are shown.
Figure 31:
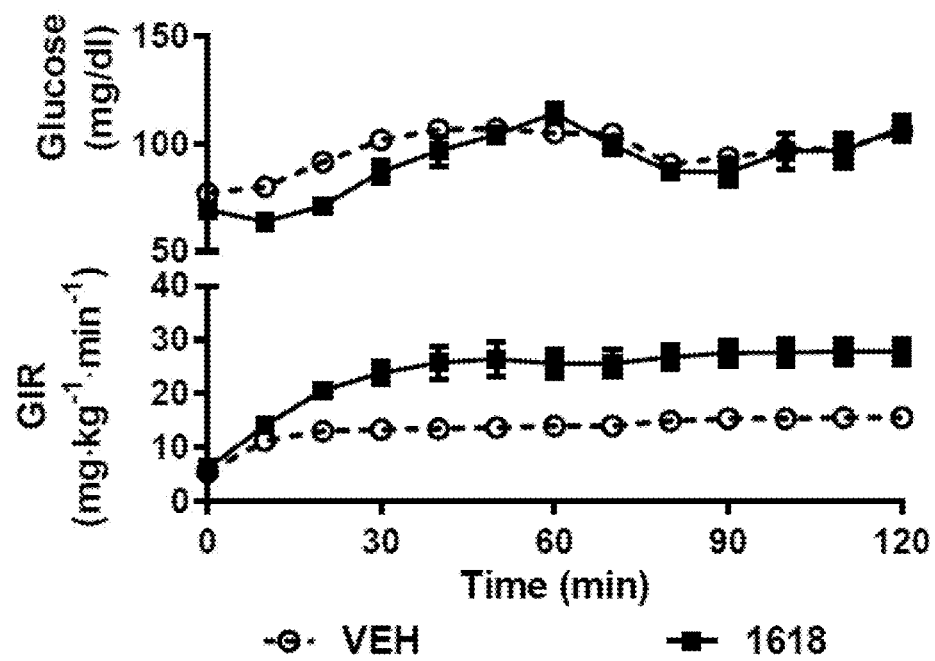
FIG. 31. From the same study as in FIG. 30, fasting plasma glucose and glucose infusion rate values are shown.
Figure 32:
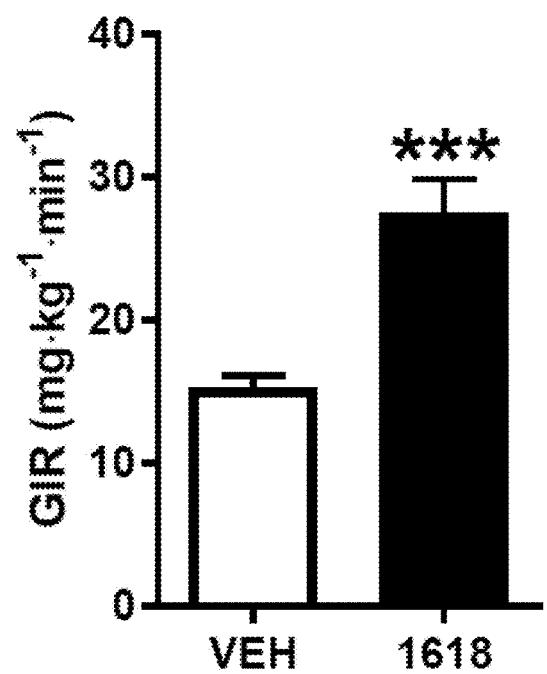
FIG. 32. From the same study as in FIG. 30, glucose infusion rate values are shown.

Diet-induced obese mice were dosed 1× with vehicle or BC1618 (20 mg/kg) prior to overnight fast, followed by a 1× (20 mg/kg) morning dose prior to hyperinsulinemic euglycemic clamp. There was no difference in body weight between groups prior to clamp (FIG. 30). Fasting plasma glucose was modestly reduced in BC1618 treated mice (111±3 vs 100±6 mg/dl; P=0.12). Plasma glucose levels were matched during the clamp (FIG. 31, upper portion). The glucose infusion rate (GIR) required to maintain euglycemia in the 1618 treated mice was approximately 2-fold greater than VEH treated mice (FIG. 31, lower portion and average over last 40 min in FIG. 32, P<0.001), indicating improved whole-body insulin sensitivity.

The above examples are given to illustrate the present inventions. It should be understood, however, that the spirit and scope of the inventions is not to be limited to the specific conditions or details described in these examples. All publicly available documents referenced herein, including but not limited to U.S. patents, are specifically incorporated by reference.

It will be apparent to those skilled in the art that various modifications and variations can be made in the methods and compositions of the present inventions without departing from the spirit or scope of the inventions. Thus, it is intended that the present inventions cover the modifications and variations of these inventions provided they come within the scope of the appended claims and their equivalents.

Para. A. A compound of Formula I:

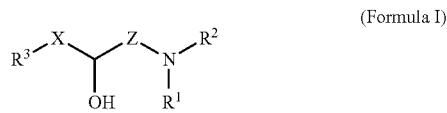

(Formula I)

wherein:
X is $C_{0-3}$ alkyl, —$(CH_2)_2$—NH—$(CH_2)_2$—, —NH—$CH_2$—, —O—$CH_2$—, —O—$(CH_2)_2$—, —$(CH_2)_2$—O—$(CH_2)_2$—, or —$(CH_2)$—C$(NH_2)$—$(CH_2)_a$—;
Z is $C_{1-2}$ alkyl, —$(CH_2)$—NH—$(CH_2)$—, —$(CH_2)$—O—$(CH_2)$—, or —$(CH_2)_a$—C$(NH_2)$—$(CH_2)$—;
a is 0 or 1;
at least one of $R^1$ and $R^2$ is —$(CHR^4)_b$—Y, wherein each $R^4$ is independently H, or a substituted or unsubstituted aryl; and b is 0 or an integer of 1-3;
the remaining one of $R^1$ and $R^2$ is —$(CH_2)_c$—Y or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and
each Y is independently a substituted or unsubstituted aryl; or
$R^1$ and $R^2$, together with the nitrogen to which they are attached, form a substituted or unsubstituted heterocyclic ring;

$R^3$ is an alkyl, carbocyclyl, aryl, or heteroaryl group, wherein each alkyl, carbocyclyl, aryl, or heteroaryl group is optionally substituted by one or more

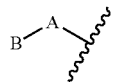

wherein

A is C=O, SO, $SO_2$, or $-(C(R^B)_2)_d-$, wherein each $R^B$ is independently selected from H, D, halogen, OH, substituted or unsubstituted alkyl, and substituted or unsubstituted alkoxy;

d is 0 or an integer of 1-3; and

B is selected from the group consisting of substituted or unsubstituted alkyl, substituted or unsubstituted alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof.

Para. B. The compound of Para. A, or a stereoisomer thereof, or a pharmaceutically acceptable salt or ester thereof, wherein $R^3$ is an alkyl group optionally substituted by one or more

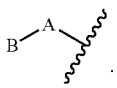

Para. C. The compound of Para. A, or a stereoisomer thereof, or a pharmaceutically acceptable salt or ester thereof, wherein $R^3$ is an carbocyclyl group optionally substituted by one or more

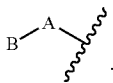

Para. D. The compound of Para. A, or a stereoisomer thereof, or a pharmaceutically acceptable salt or ester thereof, wherein $R^3$ is an aryl group optionally substituted by one or more

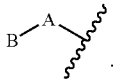

Para. E. The compound of Para. A, or a stereoisomer thereof, or a pharmaceutically acceptable salt or ester thereof, wherein $R^3$ is an heteroaryl group optionally substituted by one or more

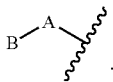

Para. F. A compound of Formula II:

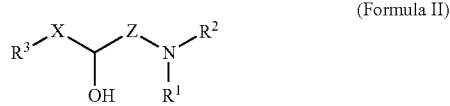

(Formula II)

wherein:

X is $C_{0-3}$ alkyl, $-(CH_2)_2-NH-(CH_2)_2-$, $-NH-CH_2-$, $-O-CH_2-$, $-O-(CH_2)_2-$, $-(CH_2)_2-O-(CH_2)_2-$, or $-(CH_2)-C(NH_2)-(CH_2)_a-$;

Z is $C_{1-2}$ alkyl, $-(CH_2)-NH-(CH_2)-$, $-(CH_2)-O-(CH_2)-$, or $-(CH_2)_a-C(NH_2)-(CH_2)-$;

a is 0 or 1;

at least one of $R^1$ and $R^2$ is $-(CHR^A)_b-Y$, wherein each $R^A$ is independently H, or a substituted or unsubstituted aryl; and b is 0 or an integer of 1-3;

the remaining one of $R^1$ and $R^2$ is $-(CH_2)_c-Y$ or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl; or $R^1$ and $R^2$, together with the nitrogen to which they are attached, form a substituted or unsubstituted heterocyclic ring;

$R^3$ is an aryl or heteroaryl group optionally substituted by one or more

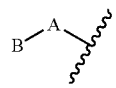

wherein

A is C=O, SO, $SO_2$, or $-(C(R^B)_2)_d-$, wherein each $R^B$ is independently selected from H, D, halogen, OH, substituted or unsubstituted alkyl, and substituted or unsubstituted alkoxy;

d is 0 or an integer of 1-3; and

B is selected from the group consisting of $C_{1-6}$ alkyl, haloalkyl, $C_{1-6}$ alkoxy, substituted or unsubstituted aryl, substituted or unsubstituted carbocyclyl, substituted or unsubstituted heterocyclyl, and substituted or unsubstituted heteroaryl;

or a stereoisomer thereof, or a pharmaceutically acceptable salt or ester thereof.

Para. G. The compound of Para. F, or a stereoisomer thereof, or a pharmaceutically acceptable salt or ester thereof, wherein $R^3$ is unsubstituted phenyl, unsubstituted naphthyl, or phenyl substituted with one or two

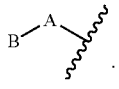

Para. H. The compound of Para. G, or a stereoisomer thereof, or a pharmaceutically acceptable salt or ester thereof, wherein $R^3$ is unsubstituted phenyl or phenyl substituted with one

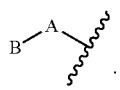

Para. I. The compound of Para. H, or a stereoisomer thereof, or a pharmaceutically acceptable salt or ester thereof, wherein $R^3$ is phenyl substituted with one

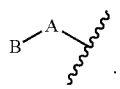

Para. J. The compound of any one of Paras. A-I, or a stereoisomer thereof, or a pharmaceutically acceptable salt or ester thereof, wherein A is $-(C(R^B)_2)_d-$.

Para. K. The compound of Para. J, or a stereoisomer thereof, or a pharmaceutically acceptable salt or ester thereof, wherein $R^B$ is H, or substituted or unsubstituted alkyl.

Para. L. The compound of Para. J, or a stereoisomer thereof, or a pharmaceutically acceptable salt or ester thereof, wherein d is 0.

Para. M. The compound of Para. J or Para. K, or a stereoisomer thereof, or a pharmaceutically acceptable salt or ester thereof, wherein d is an integer of 1-3.

Para. N. The compound of any one of Paras. A-I, or a stereoisomer thereof, or a pharmaceutically acceptable salt or ester thereof, wherein A is C=O.

Para. O. The compound of any one of Paras. A-I, or a stereoisomer thereof, or a pharmaceutically acceptable salt or ester thereof, wherein A is SO or $SO_2$.

Para. P. The compound of any one of Paras. A-O, or a stereoisomer thereof, or a pharmaceutically acceptable salt or ester thereof, wherein B is selected from the group consisting of $C_{2-6}$ alkyl, haloalkyl, $C_{2-6}$ alkoxy, substituted or unsubstituted aryl, substituted or unsubstituted carbocyclyl, substituted or unsubstituted heterocyclyl, and substituted or unsubstituted heteroaryl.

Para. Q. The compound of Para. P, or a stereoisomer thereof, or a pharmaceutically acceptable salt or ester thereof, wherein B is selected from the group consisting of $C_{2-6}$ alkyl, haloalkyl, $C_{2-6}$ alkoxy, substituted or unsubstituted phenyl, substituted or unsubstituted $C_{3-8}$ carbocyclyl, and substituted or unsubstituted six-membered heteroaryl.

Para. R. The compound of Para. Q, or a stereoisomer thereof, or a pharmaceutically acceptable salt or ester thereof, wherein B is selected from the group consisting of haloalkyl, $C_{2-6}$ alkoxy, substituted or unsubstituted phenyl, $C_{3-8}$ carbocyclyl, and substituted or unsubstituted six-membered heteroaryl.

Para. S. The compound of Para. Q or Para. R, or a stereoisomer thereof, or a pharmaceutically acceptable salt or ester thereof, wherein the substituted or unsubstituted six-membered heteroaryl is a substituted or unsubstituted pyridine.

Para. T. The compound of Para. H, or a stereoisomer thereof, or a pharmaceutically acceptable salt or ester thereof, wherein $R^3$ is unsubstituted phenyl.

Para. U. The compound of any one of Paras. A-T, or a stereoisomer thereof, or a pharmaceutically acceptable salt or ester thereof, wherein X is $C_{0-3}$ alkyl, $-NH-CH_2-$, or $-O-CH_2-$.

Para. V. The compound of any one of Paras. A-U, or a stereoisomer thereof, or a pharmaceutically acceptable salt or ester thereof, wherein X is $C_{0-3}$ alkyl.

Para. W. The compound of Para. V, or a stereoisomer thereof, or a pharmaceutically acceptable salt or ester thereof, wherein X is $C_0$ alkyl.

Para. X. The compound of Para. V, or a stereoisomer thereof, or a pharmaceutically acceptable salt or ester thereof, wherein X is $C_{1-3}$ alkyl.

Para. Y. The compound of Para. X, or a stereoisomer thereof, or a pharmaceutically acceptable salt or ester thereof, wherein X is $C_2$ alkyl.

Para. Z. The compound of Para. Y, or a stereoisomer thereof, or a pharmaceutically acceptable salt or ester thereof, wherein X is $CH_2CH_2$.

Para. AA. The compound of any one of Paras. A-U, or a stereoisomer thereof, or a pharmaceutically acceptable salt or ester thereof, wherein X is $-NH-CH_2-$.

Para. AB. The compound of any one of Paras. A-U, or a stereoisomer thereof, or a pharmaceutically acceptable salt or ester thereof, wherein X is $-O-CH_2-$.

Para. AC. The compound of any one of Paras. A-AB, or a stereoisomer thereof, or a pharmaceutically acceptable salt or ester thereof, wherein Z is $C_{1-2}$ alkyl.

Para. AD. The compound of Para. AC, or a stereoisomer thereof, or a pharmaceutically acceptable salt or ester thereof, wherein Z is $C_1$ alkyl.

Para. AE. The compound of Para. AB or Para. AC, or a stereoisomer thereof, or a pharmaceutically acceptable salt or ester thereof, wherein Z is $CH_2$.

Para. AF. The compound of any one of Paras. A-AE, or a stereoisomer thereof, or a pharmaceutically acceptable salt or ester thereof, wherein at least one of $R^1$ and $R^2$ is $-(CHR^A)_b-Y$, wherein each $R^A$ is independently H, or a substituted or unsubstituted aryl; and b is 0 or an integer of 1-3; the remaining one of $R^1$ and $R^2$ is $-(CH_2)_c-Y$ or selected from the group consisting of H, substituted or unsubstituted alkyl, substituted or unsubstituted aryl, substituted or unsubstituted carbocyclyl, and substituted or unsubstituted heterocyclyl; and c is 0 or an integer of 1-3; and each Y is independently a substituted or unsubstituted aryl.

Para. AG. The compound of any one of Paras. A-AF, or a stereoisomer thereof, or a pharmaceutically acceptable salt or ester thereof, wherein the remaining one of $R^1$ and $R^2$ is $-(CH_2)_c-Y$ or selected from the group consisting of H, substituted or unsubstituted alkyl, substituted or unsubstituted aryl, and substituted or unsubstituted carbocyclyl; and c is 0 or an integer of 1-3.

Para. AH. The compound of any one of Paras. A-AG, or a stereoisomer thereof, or a pharmaceutically acceptable salt or ester thereof, wherein the remaining one of $R^1$ and $R^2$ is $-(CH_2)_c-Y$ or H; and c is 0 or an integer of 1-3.

Para. AI. The compound of any one of Paras. A-AH, or a stereoisomer thereof, or a pharmaceutically acceptable salt or ester thereof, wherein b is 0 or 1; and the remaining one of $R^1$ and $R^2$ is $-(CH_2)-Y$ or H.

Para. AJ. The compound of any one of Paras. A-AI, or a stereoisomer thereof, or a pharmaceutically acceptable salt or ester thereof, wherein each $R^A$ is independently H, or a substituted or unsubstituted phenyl; b is 0 or 1; the remaining one of $R^1$ and $R^2$ is $-(CH_2)-Y$ or H; and each Y is a substituted or unsubstituted phenyl.

Para. AK. The compound of any one of Paras. A-AJ, or a stereoisomer thereof, or a pharmaceutically acceptable salt or ester thereof, wherein $R^A$ is H.

Para. AL. The compound of any one of Paras. A-AJ, or a stereoisomer thereof, or a pharmaceutically acceptable salt or ester thereof, wherein $R^4$ is phenyl.

Para. AM. The compound of any one of Paras. A-AL, or a stereoisomer thereof, or a pharmaceutically acceptable salt or ester thereof, wherein b is 1.

Para. AN. The compound of any one of Paras. A-AL, or a stereoisomer thereof, or a pharmaceutically acceptable salt or ester thereof, wherein b is 0.

Para. AO. The compound of any one of Paras. A-AN, or a stereoisomer thereof, or a pharmaceutically acceptable salt or ester thereof, wherein the remaining one of $R^1$ and $R^2$ is —$(CH_2)$—Y.

Para. AP. The compound of any one of Paras. A-AN, or a stereoisomer thereof, or a pharmaceutically acceptable salt or ester thereof, wherein the remaining one of $R^1$ and $R^2$ is H.

Para. AQ. The compound of any one of Paras. A-AE, or a stereoisomer thereof, or a pharmaceutically acceptable salt or ester thereof, wherein $R^1$ and $R^2$, together with the nitrogen to which they are attached, form a substituted or unsubstituted heterocyclic ring.

Para. AR. The compound of Para. AQ, or a stereoisomer thereof, or a pharmaceutically acceptable salt or ester thereof, wherein $R^1$ and $R^2$, together with the nitrogen to which they are attached, form a substituted or unsubstituted tetrahydroisoquinoline.

Para. AS. A compound selected from the group consisting of

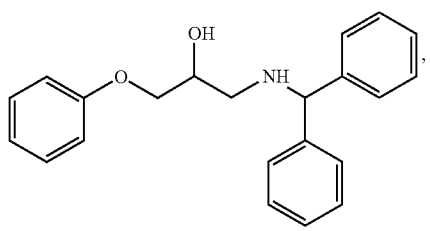,

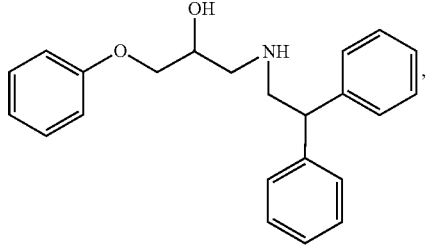,

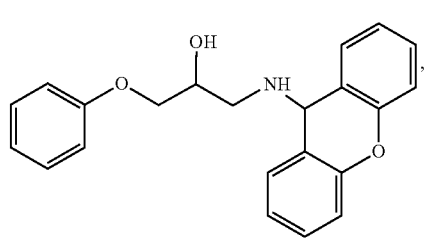,

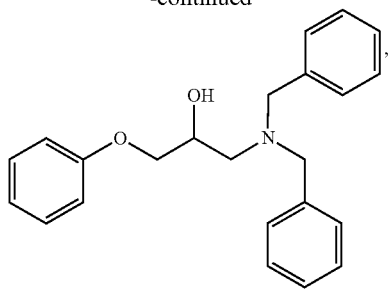,

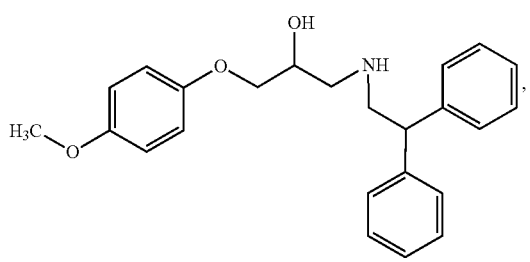,

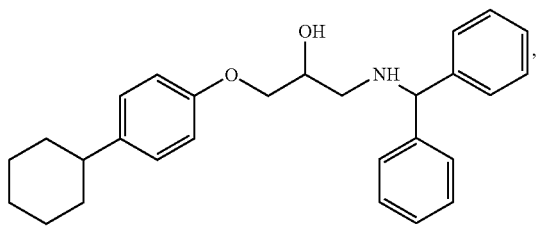,

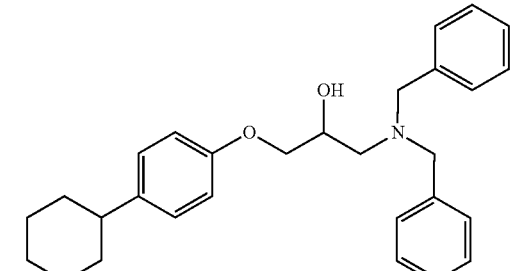,

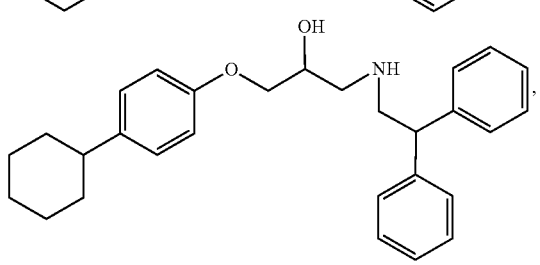,

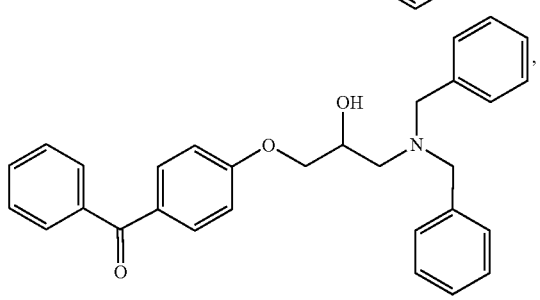,

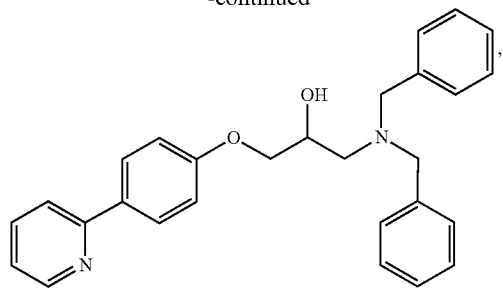
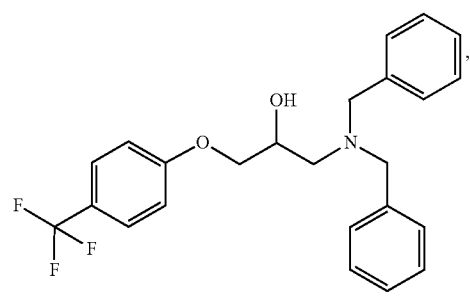
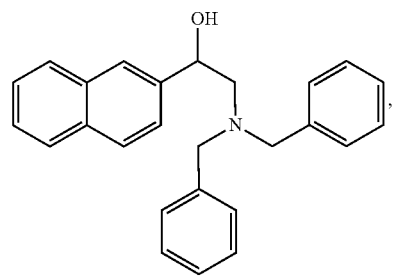
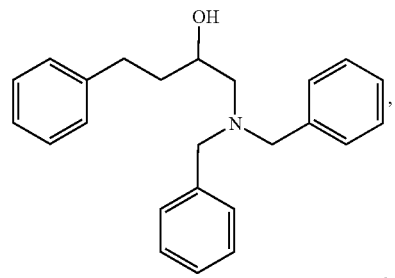
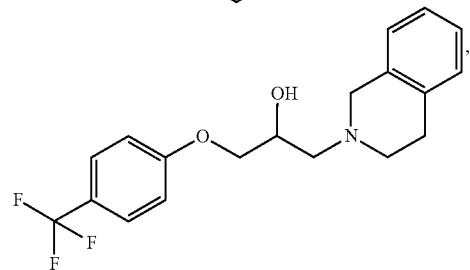
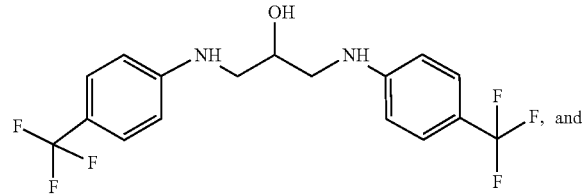
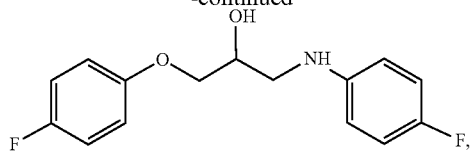
or a stereoisomer thereof, or a pharmaceutically acceptable salt or ester thereof.
Para. AT. A compound selected from the group consisting of
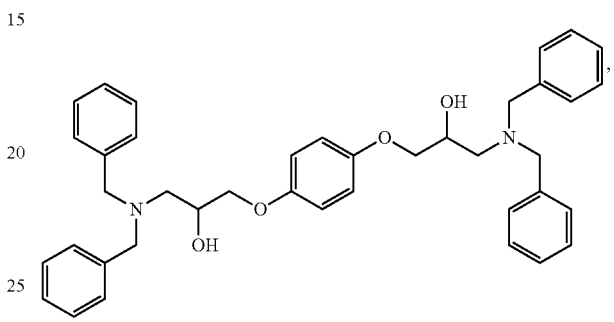
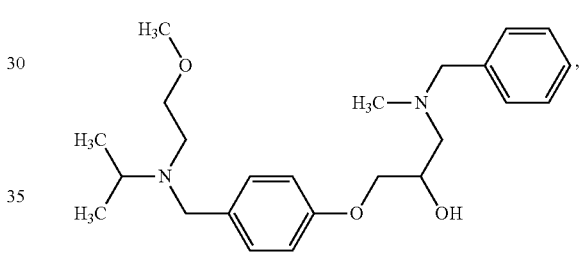
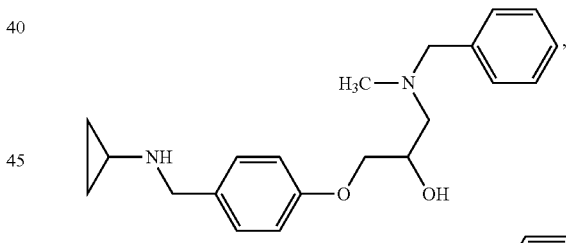
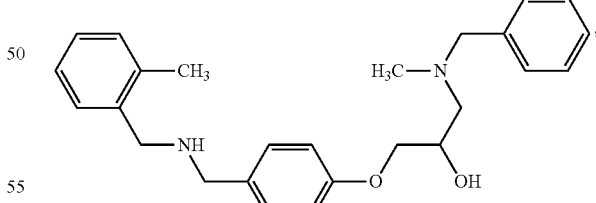
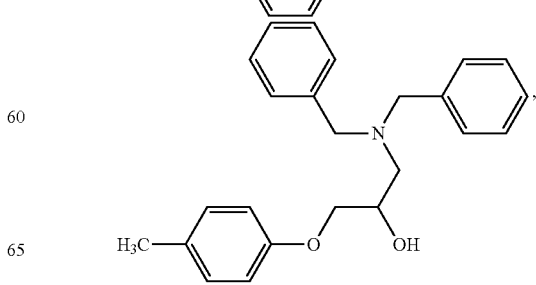

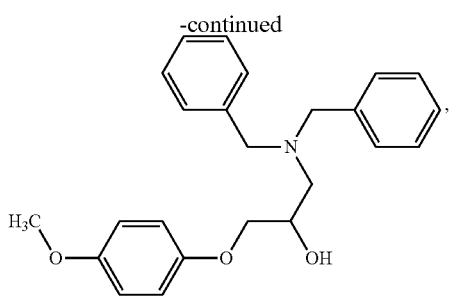

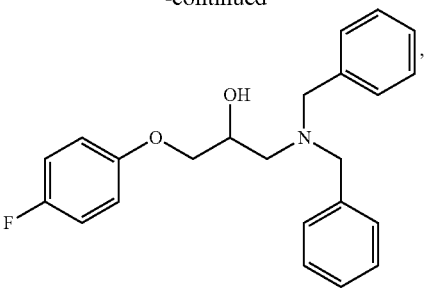

or a stereoisomer thereof, or a pharmaceutically acceptable salt or ester thereof.

Para. AU. A method to bind a ubiquitin E3 ligase, the method comprising contacting the ubiquitin E3 ligase with a compound, or a stereoisomer thereof, or a pharmaceutically acceptable salt or ester thereof, of any one of Paras. A-AT.

Para. AV. A method to treat inflammation in a subject in need thereof, the method comprising administering to the subject a therapeutically effective amount of a compound, or a stereoisomer thereof, or a pharmaceutically acceptable salt or ester thereof, of any one of Paras. A-AT.

Para. AW. A method to treat cytokine-driven inflammation in a subject in need thereof, the method comprising administering to the subject a therapeutically effective amount of a compound, or a stereoisomer thereof, or a pharmaceutically acceptable salt or ester thereof, of any one of Paras. A-AT.

Para. AX. A method to treat sepsis in a subject in need thereof, the method comprising administering to the subject a therapeutically effective amount of a compound, or a stereoisomer thereof, or a pharmaceutically acceptable salt or ester thereof, of any one of Paras. A-AT.

Para. AY. A method to treat acute lung injury in a subject in need thereof, the method comprising administering to the subject a therapeutically effective amount of a compound, or a stereoisomer thereof, or a pharmaceutically acceptable salt or ester thereof, of any one of Paras. A-AT.

Para. AZ. A method to increase the level of phosphorylated-AMPK in a subject in need thereof, the method comprising administering to the subject a therapeutically effective amount of a compound, or a stereoisomer thereof, or a pharmaceutically acceptable salt or ester thereof, of any one of Paras. A-AT.

Para. BA. A method to disrupt interaction between Fbxo48 and phosphorylated-AMPK in a cell, the method comprising contacting the cell with a compound, or a stereoisomer thereof, or a pharmaceutically acceptable salt or ester thereof, of any one of Paras. A-AT.

Para. BB. A method to disrupt interaction between Fbxo48 and phosphorylated-AMPK in a subject in need thereof, the method comprising administering to the subject a therapeutically effective amount of a compound, or a stereoisomer thereof, or a pharmaceutically acceptable salt or ester thereof, of any one of Paras. A-AT.

Para. BC. A method to treat metabolic syndrome in a subject in need thereof, the method comprising administering to the subject a therapeutically effective amount of a compound, or a stereoisomer thereof, or a pharmaceutically acceptable salt or ester thereof, of any one of Paras. A-AT.

TABLE 1

| Compound # | Structure | pAMPK IC$_{50}$ |
|---|---|---|
| 1 (BC1583) | (structure) | ++ |
| 2 (BC15150) | (structure) | + |
| 3 (BC15151) | (structure) | + |
| 4 (BC15152) | (structure) | + |
| 5 (BC15153) | (structure) | ++ |

TABLE 1-continued

| Compound # | Structure | pAMPK IC$_{50}$ |
|---|---|---|
| 6 (BC15154) | 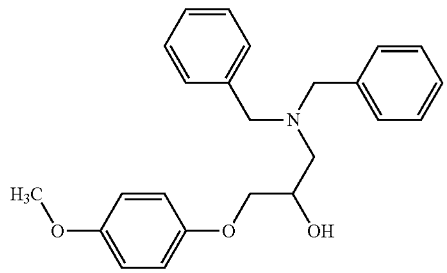 [SMILES: COc1ccc(OCC(O)CN(Cc2ccccc2)Cc2ccccc2)cc1] | ++ |
| 7 (BC15155) | 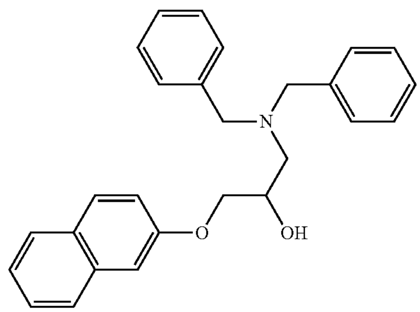 [SMILES: OC(COc1ccc2ccccc2c1)CN(Cc1ccccc1)Cc1ccccc1] | ++ |
| 8 (BC15156) | 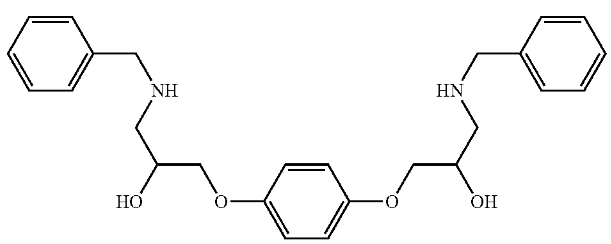 [SMILES: OC(CNCc1ccccc1)COc1ccc(OCC(O)CNCc2ccccc2)cc1] | + |
| 9 (BC15157) | 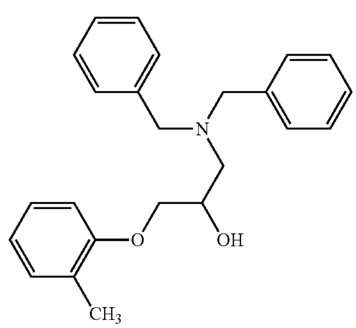 [SMILES: Cc1ccccc1OCC(O)CN(Cc1ccccc1)Cc1ccccc1] | ++ |
| 10 (BC15158) | 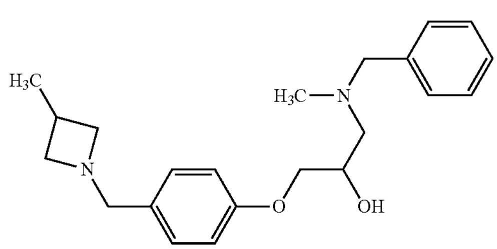 [SMILES: CC1CN(Cc2ccc(OCC(O)CN(C)Cc3ccccc3)cc2)C1] | + |

TABLE 1-continued

| Compound # | Structure | pAMPK IC$_{50}$ |
|---|---|---|
| 11 (BC1601) | 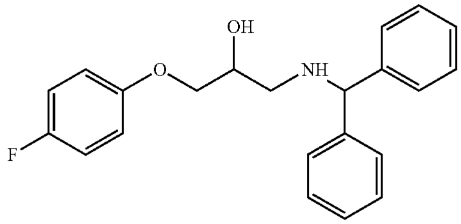 [SMILES: OC(CNC(c1ccccc1)c1ccccc1)COc1ccc(F)cc1] | ++ |
| 12 (BC1609) | 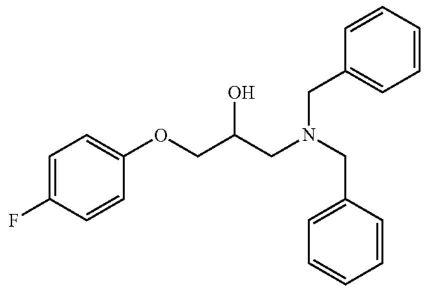 [SMILES: OC(COc1ccc(F)cc1)CN(Cc1ccccc1)Cc1ccccc1] | +++ |
| 13 (BC15160) | 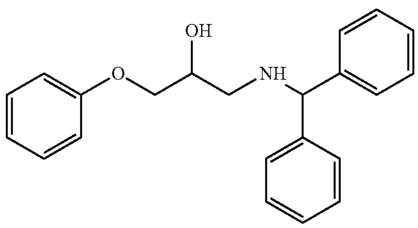 [SMILES: OC(CNC(c1ccccc1)c1ccccc1)COc1ccccc1] | ++ |
| 14 (BC15161) | 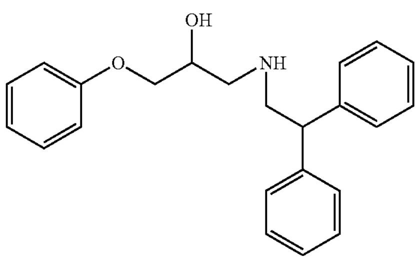 [SMILES: OC(CNCC(c1ccccc1)c1ccccc1)COc1ccccc1] | ++ |
| 15 (BC1602) | 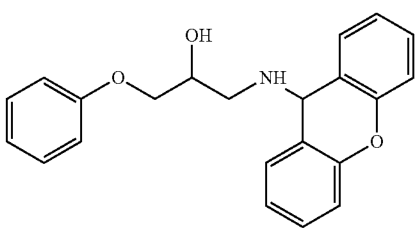 [SMILES: OC(CNC1c2ccccc2Oc2ccccc21)COc1ccccc1] | + |
| 16 (BC1603) | 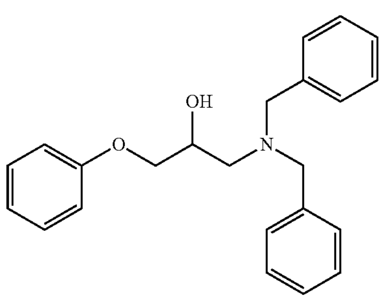 [SMILES: OC(COc1ccccc1)CN(Cc1ccccc1)Cc1ccccc1] | ++ |

TABLE 1-continued

| Compound # | Structure | pAMPK IC$_{50}$ |
|---|---|---|
| 17 (BC1604) | 4-methoxyphenoxy-CH$_2$-CH(OH)-CH$_2$-NH-CH$_2$-CH(Ph)$_2$ | ++ |
| 18 (BC1606) | 4-cyclohexylphenoxy-CH$_2$-CH(OH)-CH$_2$-NH-CH(Ph)$_2$ | ++ |
| 19 (BC1607) | 4-cyclohexylphenoxy-CH$_2$-CH(OH)-CH$_2$-N(CH$_2$Ph)$_2$ | ++ |
| 20 (BC1608) | 4-cyclohexylphenoxy-CH$_2$-CH(OH)-CH$_2$-NH-CH$_2$-CH(Ph)$_2$ | + |
| 21 (BC1610) | 4-benzoylphenoxy-CH$_2$-CH(OH)-CH$_2$-N(CH$_2$Ph)$_2$ | + |

TABLE 1-continued

| Compound # | Structure | pAMPK IC$_{50}$ |
|---|---|---|
| 22 (BC1611) | 2-pyridyl-phenyl-O-CH$_2$-CH(OH)-CH$_2$-N(CH$_2$Ph)$_2$ | + |
| 23 (BC1618) | 4-(CF$_3$)-C$_6$H$_4$-O-CH$_2$-CH(OH)-CH$_2$-N(CH$_2$Ph)$_2$ | +++ |
| 24 | 2-naphthyl-CH(OH)-CH$_2$-N(CH$_2$Ph)$_2$ | ++ |
| 25 | Ph-CH$_2$-CH$_2$-CH(OH)-CH$_2$-N(CH$_2$Ph)$_2$ | + |
| 26 | 4-(CF$_3$)-C$_6$H$_4$-O-CH$_2$-CH(OH)-CH$_2$-N(1,2,3,4-tetrahydroisoquinolin-2-yl) | + |

TABLE 1-continued

| Compound # | Structure | pAMPK IC$_{50}$ |
|---|---|---|
| 27 | ![structure] | + |
| 28 | ![structure] | + |

"+" represents IC$_{50}$ value of >10 μg/mL;
"++" represents IC$_{50}$ value of 1 to 10 μg/mL;
"+++" represents IC$_{50}$ value of <1 μg/mL While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound of Formula II:

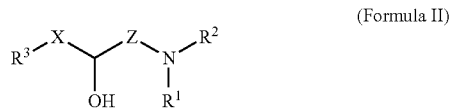
(Formula II)

wherein:

X is —O—CH$_2$—;

Z is CH$_2$;

at least one of R$^1$ and R$^2$ is -(CHR$^4$)$_b$—Y, wherein each R$^4$ is independently H; and b is 1;

the remaining one of R$^1$ and R$^2$ is (CH$_2$)–Y; and each Y is independently phenyl or substituted phenyl;

$R^3$ is phenyl substituted by one

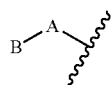

wherein

A is $-(C(R^B)_2)_d-$, wherein each $R^B$ is independently selected from H, D, halogen, OH, substituted or unsubstituted alkyl, and substituted or unsubstituted alkoxy; d is 0; and B is selected from the group consisting of haloalkyl, unsubstituted aryl, substituted or unsubstituted carbocyclyl, unsubstituted heterocyclyl, and unsubstituted heteroaryl;

or a stereoisomer thereof, or a pharmaceutically acceptable salt or ester thereof.

2. The compound of claim 1, wherein B is haloalkyl.

3. The compound of claim 1, wherein B is unsubstituted aryl.

4. The compound of claim 1, wherein B is substituted carbocyclyl.

5. The compound of claim 1, wherein B is unsubstituted carbocyclyl.

6. The compound of claim 1, wherein B is unsubstituted heterocyclyl.

7. The compound of claim 1, wherein B is unsubstituted heteroaryl.

8. A pharmaceutical composition comprising a compound of claim 2, or a pharmaceutically acceptable salt thereof.

9. A method of treating inflammation in a subject in need thereof, the method comprising administering to the subject a therapeutically effective amount of a compound, or a stereoisomer thereof, or a pharmaceutically acceptable salt thereof, of claim 1.

10. A method of treating sepsis in a subject in need thereof, the method comprising administering to the subject a therapeutically effective amount of a compound, or a stereoisomer thereof, or a pharmaceutically acceptable salt thereof, of claim 1.

11. A method of treating metabolic syndrome in a subject in need thereof, the method comprising administering to the subject a therapeutically effective amount of a compound, or a stereoisomer thereof, or a pharmaceutically acceptable salt thereof, of claim 1.

12. A compound selected from the group consisting of:

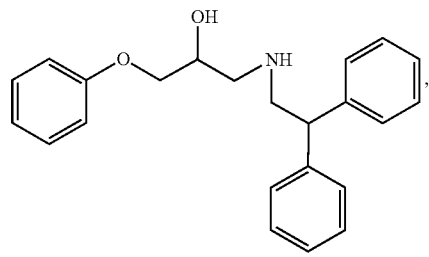

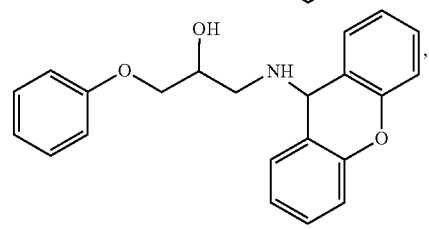

-continued

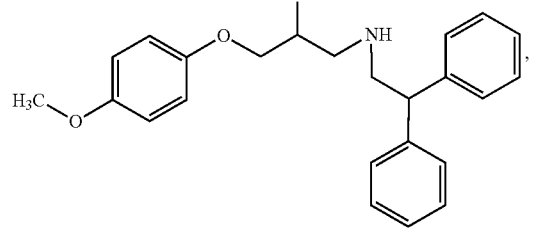

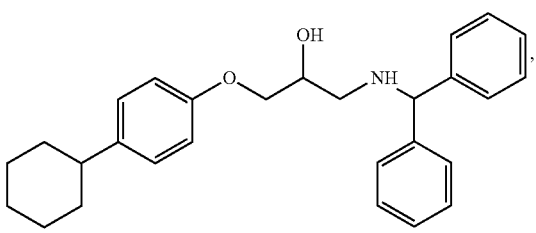

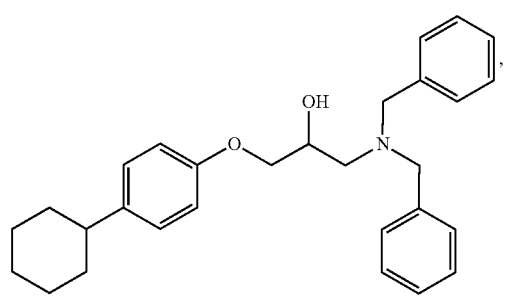

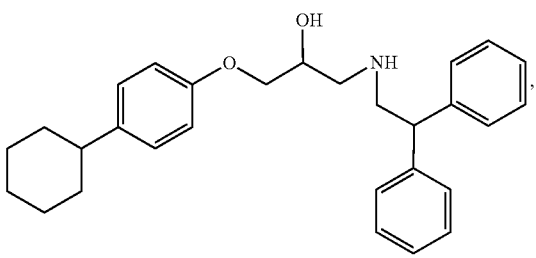

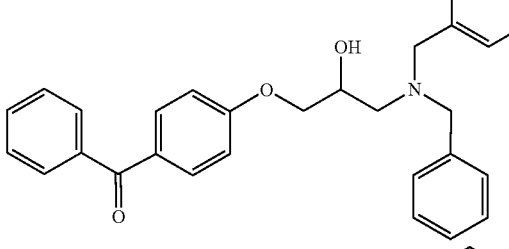

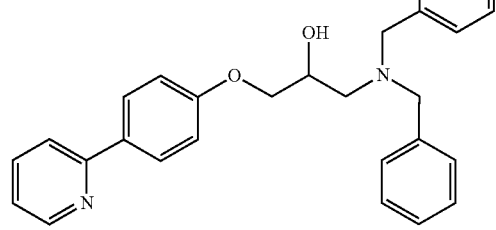

-continued

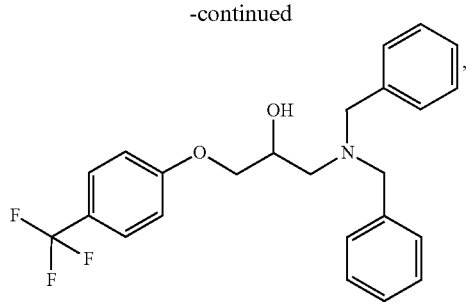

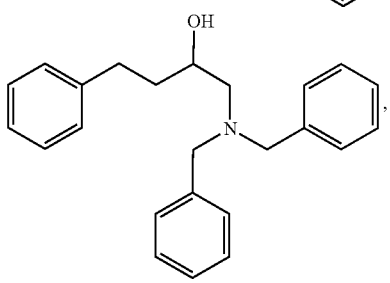

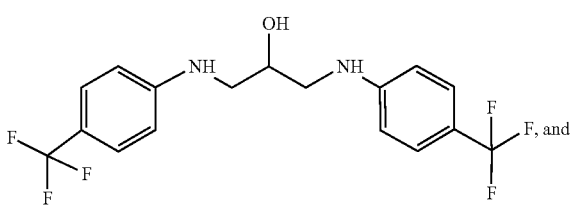

-continued

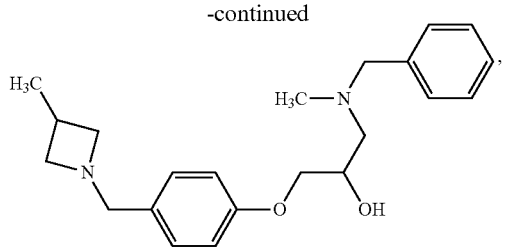

stereoisomer thereof, or a pharmaceutically acceptable salt thereof.

13. A pharmaceutical composition comprising a compound of claim 12, or a pharmaceutically acceptable salt thereof.

14. A method of treating inflammation in a subject in need thereof, the method comprising administering to the subject a therapeutically effective amount of a compound, or a stereoisomer thereof, or a pharmaceutically acceptable salt thereof, of claim 12.

15. A method of treating sepsis in a subject in need thereof, the method comprising administering to the subject a therapeutically effective amount of a compound, or a stereoisomer thereof, or a pharmaceutically acceptable salt thereof, of claim 12.

16. A method of treating metabolic syndrome in a subject in need thereof, the method comprising administering to the subject a therapeutically effective amount of a compound, or a stereoisomer thereof, or a pharmaceutically acceptable salt thereof, of claim 12.

* * * * *

UNITED STATES PATENT AND TRADEMARK OFFICE
CERTIFICATE OF CORRECTION

PATENT NO. : 11,673,853 B2
APPLICATION NO. : 17/313577
DATED : June 13, 2023
INVENTOR(S) : Beibei Chen, Rama K. Mallampalli and Yuan Liu It is certified that error appears in the above-identified patent and that said Letters Patent is hereby corrected as shown below:

In the Claims

Column 63, Line 30, Claim 8, please delete "claim 2" and insert therefor -- claim 1 --.

Signed and Sealed this
First Day of October, 2024

Katherine Kelly Vidal
*Director of the United States Patent and Trademark Office*